United States Patent [19]
Lee et al.

[11] Patent Number: 5,426,181
[45] Date of Patent: Jun. 20, 1995

[54] DNA ENCODING CYTOKINE-INDUCED PROTEIN, TSG-14

[75] Inventors: Tae H. Lee, Cambridge, Mass.; Gene W. Lee; Jan Vilcek, both of New York, N.Y.

[73] Assignee: New York University, New York, N.Y.

[21] Appl. No.: 929,580

[22] Filed: Aug. 14, 1992

Related U.S. Application Data

[63] Continuation of Ser. No. 640,492, Jan. 14, 1991, abandoned.

[51] Int. Cl.[6] .............. C07H 17/00; C12N 1/20; C12N 15/00; C12P 21/06
[52] U.S. Cl. .................. 536/23.5; 536/23.1; 435/252.3; 435/320.1; 435/69.1
[58] Field of Search ............ 435/69.1, 69.5, 240.1, 435/252.3, 243; 536/23.1, 23.5

[56] References Cited
PUBLICATIONS

Lee et al, *Mol. Cell Biol* 10(5) 1990, pp. 1982–1988.
Lee et al *J. Interferon Res* 9(Suppl 2) 1989, p. 5145.
Breviario et al *JBC* 267(31) 1992, pp. 22190–22197.

*Primary Examiner*—Garnette D. Draper
*Assistant Examiner*—Elizabeth C. Kemmerer
*Attorney, Agent, or Firm*—Browdy and Neimark

[57] ABSTRACT

Pleiotropic pro-inflammatory cytokines, such as TNF and IL-1, induce expression of a polypeptide molecule, termed TSG-14, in connective tissue cells. The TSG-14 polypeptide and functional derivatives thereof, DNA coding therefor, expression vehicles, such as a plasmids, and host cells transformed or transfected with the DNA molecule, and methods for producing the polypeptide and the DNA are provided. Antibodies specific for the TSG-14 polypeptide are disclosed, as is a method for detecting the presence of TSG-14 polypeptide in a biological sample, using the antibody or another molecule capable of binding to TSG-14 such as hyaluronic acid. A method for detecting the presence of nucleic acid encoding a normal or mutant TSG-14 polypeptide, a method for measuring induction of expression of TSG-14 in a cell using either nucleic acid hybridization or immunoassay, a method for identifying a compound capable of inducing the expression of TSG-14 in a cell, and a method for measuring the ability of a cell to respond to TNF are also provided.

8 Claims, 19 Drawing Sheets

TSG-1

TSG-6

TSG-8

TSG-12

TSG-14

TSG-21

TSG-27

TSG-37

FIG. 4(1)

```
1
AATTCGCGCTCAACTCAGCTCACTGAGAGTCTCCCGCCAGCTGTGGAAAGAACTTTGCGTCTCTCCACGAATGCATCTCCTTGCGATTCTG
                                                                        MetHisLeuLeuAlaIleLeu

94
TTTTGTGCTCTCTCGGTCTCGCAGTGTTGGCCGAGAACTCGGATGATTATGATCTCATGTATGTGAATTTGGACAACGAAATAGACAATGGACTC
PheCysAlaLeuTrpSerAlaValLeuAlaGluAlaAsnSerAspAspTyrAspLeuMetTyrValAsnLeuAspAsnGluIleAspGlyLeu

187
CATCCCACTGAGGACCCCACGCCGTGCGACTGCGGTCAGGAGCACTCGGAATGGCACAAGCTCTTCATCATGCTGGAGAACTCGCAGATGAGA
HisProThrGluAspProThrProCysAspCysGlyGlnGluHisSerGluTrpHisGlnLeuPheIleMetLeuGluAsnSerGlnMetArg

280
GAGGCATGCTGCTGCAAGCCACGACGACGTCCTGCGGGGACGACTGCAGAGGCTGCGAGTCGCAGAGGCTGGGCCGGCTCCGCGAAAGCCTGCG
GluArgMetLeuLeuGlnAlaThrThrSerAspValLeuArgGlyGluGluLeuArgLeuAlaArgLeuAlaGlyLeuAlaSerLeuAla

373
AGGCCGTGCGCGGCGGGGCTCCCGCAGAGGCCAGGCTGCTCTGGACCAGTGCTCTGCAGGCCACCCGCGACCCCGACGCGGGCCGCAGGCTG
ArgProCysAlaProGlyAlaProGlyAlaProAlaGluAlaArgLeuThrSerAlaLeuAspGluLeuLeuGlnAlaThrArgAspAlaThrArgAlaGlyArgArgLeu

466
GCGCGTATGGAGGGCGGAGGCGCAGGCGCCCAGAGAGGCGCCCTGGCCGGTGCTGAGGAGCTGCGGGCGACGCGAGCCGACCT
AlaArgMetGluGlyGlyAlaGluAlaGlnArgProGluGluAlaGlyArgAlaLeuAlaAlaValLeuArgSerCysGlyAspAlaSerArgPro

559
GCACGCGGTGCAGGGCTGGCCTGCCCGGAGCTGGCTGCCGGCACGTTGTGAAACAGCTATTTTATTCCCAATGCGTTCCAAGAAGATTTTGG
AlaArgGlyAlaGlyLeuGlyLysCysProGluLeuAlaAlaGlyArgLeuEnd

652
AAGCGTGCATCCAGTGAGACCTTTGAGGCTTTGAGTCTTTTAGTGCCTGCATTTGGGTCAAAGCCACAGATGTATTAAACAAAACCATCCTGTT

745
TTCCTATGGCACAAAGAGGAATCCATATGAAATCCAGCTACCAATCCATAGTGTTTGTGGTGGAGAGAGAACAAACT

838
GGTTGCTGAAGCCATGGTTTCCCTGGGAAGGTGACCCACCTGTGCGGGAATTCAGAGGAAGGGCTCACATCCTTGTGGGTAAATGG
```

FIG. 4(2)

```
931
TGAACTGGGCGGCTACCACTGTTGAGATGGCCACAGTCACATTGTTCCTGAGGGAGGAATCCTGCAGATTGGCCAAGAAAAGAATGGCTGCTG

1024
TGTGGGTGGTGGCTTTGATGAAACATTAGCCTTCTCTCTGGGAGACTCACAGGCTTCAATATCTGGGATAGTGTTCTTAGCAATGAAGAGATAAG

1117
AGAGACCGGAGGAGCAGAGTCTTGTCACATCCGGGGGAATATTGTTGGGTGGGGAGTCACAGAGATCCAGCCACATGGAGGAGCTCAGTATGT

1210
TTCATAAATGTGTGAAACTCCACTTGAAGCCAAAGAAAGAAACTCACACTTAAAACACATGCCAGTTGGGAAGGTCTGAAAACTCAGTGCAT

1303
AATAGGAACACTTGAGACTAATGAAAGAGAGTTGAGACCAATCTTTATTTGTACTGGCCAAATACTGAATAAACAGTTGAAGGAAAGACAT

1396
TGGAAAAAGCTTTTGAGGATAAATGTTACTAGACTTTATGCCATGGTGCTTTCAGTTTAATGCTGTGTCTCTGTCAGATAAACTCTCAAATAAT

1489
TAAAAGGACTGTATTGTTGAACAGAGGGACAATGTTTTACTTTTCTTTGGTTAATTTTGTTTTGGCCAGAGATGAATTTTACATTGGAAGA

1582
ATAACAAATAAGATTTGTTGTCCATTGTTCATTGTTATTGGTATGTACCTTATTACAAAAAAAATGATGAAAACATATTTATACTACAAGGT

1675
GACTTAACAACTATAAATGTAGTTTATGTTTATAATCGAATGTCACGTTTTTGAGAAGATAGTCATATAAGTTATATATTGCAAAAGGGATTTG

1768
TATTAATTTAAGACTATTTTGTAAAGCTCTACTGTAAATAAAATATTTATAAACTAAACGGAATTC  1837
```

```
 -73                                                  GAATTCGCGCTCA                -61
 -60  ACTCAGCTCACTGAGAGTCTCTCCGCCAGCTGTGGAAAGAACTTTGCGTCTCTCCAGCA                   -1
   1  ATGCATCT CCTTGCGATTCTGTT T TGTGCTCTCTGGT CTGCAGTGTTGGCCGAGAACTCG              60
   1  Met His Leu Leu Ala Ile Leu Phe Cys Ala Leu Phe Cys Ala Leu Trp Ser Ala Val Leu Ala Glu Asn Ser   20

61  GATGATTAT GATCTCATGTAT GTG AATTTGGACAACGAAATAGACAATG GACTCCATCCC             120
  21  Asp Asp Tyr Asp Leu Met Tyr Val Asn Leu Asp Asn Glu Ile Asp Asn Gly Leu His Pro    40

121  ACTGAGGACCCCACGCCCGTGCGACTGCGGTCAGGAGCACTCGGAATGGACAAGCTCTTC                 180
  41  Thr Glu Asp Pro Thr Pro Cys Asp Cys Gly Gln Glu His Ser Glu Trp Asp Lys Leu Phe   60

181  ATCATGCTGGAGAACTCGCAGAGATGAGAGAGCGCATGCTGCTGCAAGCCACGGACGACGTC               240
  61  Ile Met Leu Glu Asn Ser Gln Met Arg Glu Arg Met Leu Gln Ala Thr Asp Asp Val    80

241  CTGCGGGGCGAGCTGCAGAGGCTGCAGAGGCTGCGGGAGGAGCTGGGGCCGAAAGCCTGGCG               300
  81  Leu Arg Gly Glu Leu Gln Arg Leu Arg Glu Glu Leu Gly Arg Leu Ala Glu Ser Leu Ala  100

301  AGGCCGTGCGCGCCCACGCCTCCCGCAGAGGCTCTGACCAGTGTGCTCTGGACGAGCTG                  360
 101  Arg Pro Cys Ala Pro Gly Ala Pro Ala Glu Ala Arg Leu Thr Ser Ala Leu Asp Glu Leu 120

361  CTGCAGGCGACCCGCGACGCAGGCTGGGCCGCGTATGGAGGCGCGGAGGCGCAG                       420
 121  Leu Gln Ala Thr Arg Asp Ala Gly Arg Arg Leu Ala Arg Met Glu Gly Ala Glu Ala Gln 140

421  CGCCCAGAGGAGGCGCGCCCTGGCCCTGTCTAGAGGAGCTGCGGGCCAGACGCGA                      480
 141  Arg Pro Glu Glu Ala Arg Ala Leu Ala Ala Ala Val Leu Glu Glu Leu Arg Gln Thr Arg 160

481  GCCGACCTGCAC GCGGTGCAGGGCTGCAGGGCTGGGCTGCCCGGAGCTGCCGGCAGGT TGTGAA           540
 161  Ala Asp Leu His Ala Val Gln Gly Trp Ala Ala Arg Ser Trp Leu Pro Ala Gly Cys Glu 180

541  ACAGCTATT TTA TTC CCAATG CGTTCCAAGAAG ATT TTT GGAAGCGTGCATCCAGTGAGA          600
 181  Thr Ala Ile Leu Phe Pro Met Arg Ser Lys Lys Ile Phe Gly Ser Val His Pro Val Arg 200
```

FIG. 9A(1)

| | | |
|---|---|---|
| 601 | CCTTTGAGGCTT GAG TCT TTT AGTGCCTGC ATT TGGGTC AAAGCCACAGATGTA TTAAAC | 660 |
| 201 | Pro Leu Arg Leu Glu Ser Phe Ser Ala Cys Ile Trp Val Lys Ala Thr Asp Val Leu <u>Asn</u> | 220 |
| 661 | AAAACC ATCCTG TTT TCC TATGGC ACAAAGAGG AATCCA TAT GAAATCCAGCTGTATCTC | 720 |
| 221 | <u>Lys Thr</u> Ile Leu Phe Ser Tyr Gly Thr Lys Arg Asn Pro Tyr Glu Ile Gln Leu Tyr Leu | 240 |
| 721 | AGCTAC CAATCC ATAGTG TTT GTG GTGGGTGGAGAGGAGAAC AAACTGGTTGCTGAAGCC | 780 |
| 241 | Ser Tyr Gln Ser Ile Val Phe Val Val Gly Gly Glu Glu Asn Lys Leu Val Ala Glu Ala | 260 |
| 781 | ATG GTT TCCCTGGGAAGGTGGACCCAC CTGTGC GGCACCTGG AATTCAGAGGAAGGGCTC | 840 |
| 261 | Met Val Ser Leu Gly Arg Trp Thr His <u>Leu Cys Gly Thr Trp Asn Ser</u> Glu Glu Gly Leu | 280 |
| 841 | ACATCC TTG TGGGTA AATGGTGAACTG GCGGCT ACC ACTGTTGAGATGGCCACAGGTCAC | 900 |
| 281 | Thr Ser Leu Trp Val Asn Gly Glu Leu Ala Ala Thr Thr Val Glu Met Ala Thr Gly His | 300 |
| 901 | ATT GTT CCT GAGGGAGGAATCCTGCAGATTGGC CAAGAAAAG AATGGCTGCTGTGTGGGT | 960 |
| 301 | Ile Val Pro Glu Gly Gly Ile Leu Gln Ile Gly Gln Glu Lys Asn Gly Cys Cys Val Gly | 320 |
| 961 | GGTGGC TTT GAT GAAACATTAGCC TTCTCTGGGAGACTCACAGGC TTC AATATCTGGGAT | 1020 |
| 321 | Gly Gly Phe Asp Glu Thr Leu Ala Phe Ser Gly Arg Leu Thr Gly Phe Asn Ile Trp Asp | 340 |
| 1021 | AGT GTT CTTAGC AATGAAGAGATAAGAGAGACCGGAGGAGCAGAGTCTTGTCACATCCGG | 1080 |
| 341 | Ser Val Leu Ser Asn Glu Glu Ile Arg Glu Thr Gly Gly Ala Glu Ser Cys His Ile Arg | 360 |
| 1081 | GGGAAT ATT GTT GGGTGGGGAGTCACAGAGATCCAGCCACATGGAGGAGCTCAGTATGTT | 1140 |
| 361 | Gly Asn Ile Val Gly Trp Gly Val Thr Glu Ile Gln Pro His Gly Gly Ala Gln Tyr Val | 380 |
| 1141 | TCA TAAATGTTG TGAAACTCC ACT TGAAGCCAAAGAAAAGAAACTCACA CTTAAAACACAT | 1200 |
| 381 | Ser End | 400 |

FIG. 9A(2)

```
1201  GCC AGTTGGGAA GGTCTGAAA ACTCAGTGC ATAATAGGAACA CTTGAGACTAATGAAAGA   1260
1261  GAG AGTTGAGAC CAA TCTTTA TTTGTACTG GCCAAATACTGA ATAAACAGTTGAAGGAAA  1320
1321  GAC ATTGGAAAA AGC TTTTGA GGATAATGT TACTAGACTTTATGC CATGGTGCT TTCAGT 1380
1381  TTA ATGCTGTGT CTC TGTCAG ATAAACTCT CAAATAATTAAAAAGGAC TGTATT GTTGAA 1440
1441  CAGAGGGACAAT TGT TTTACT TTTCTTTGG TTA ATT TTGTTTTGGCCAGAGATG AATTTT 1500
1501  ACA TTGGAAGAA TAA CAAAAT AAGATTTGT TGT CCATTGTTCATT GTT ATTGGTATGTAC 1560
1561  CTT ATTACAAAA AAA ATGATG AAAACATAT TTA TACTACAAGGTGACTTAACAA CTATAA  1620
1621  ATG TAG TTTATG TGT TATAAT CGAATGTCA CGT TTTTGAGAAGATAGTCATATA AGTTAT 1680
1681  ATT GCAAAAGGG ATTTGT ATT AAT TTAAGA CTA TTTTTG TAAAGCTCTACTGTAAATAAA 1740
1741  ATA TTT TATAAA ACTAAACGG AATTC   1766
```

FIG. 9A(3)

```
TSG-14   180 E T A I L F P M R S K K I F G S V H P V R P L - - R L E S F S A 209
Hu CRP    25 R K A F V F P K E S D T S Y V S L K A P L T K - - P L K A F T V 53
Hu SA-P   24 L S G K V F V F P R E S V T D H V N L I T P L E K P L Q N F T L 54

TSG-14       C I - W V K A T D V L N K T I L F S Y G T K R N P Y E I Q L Y L 240
Hu CRP       C L H F Y T E L S S T R G Y S I F S Y A T K R Q D N E I L I F W 85
Hu SA-P      C F - R A - Y S D L S R A Y S L F S Y N T Q G R D N E L L V Y K 84

TSG-14       S Y Q I S I V F V V G G E E N K L V A E A M V S L G R W T H L C 271
Hu CRP       S K D I G Y S F T V G G S E I I L F E V P E V T V A P - V H I C 116
Hu SA-P      E - R - V G E Y S L Y I G R H K V T P K V I E K F P A P V H I C 115

TSG-14       G T W N S E E G L T S L W V N G E L A A T T V E M A T G H I V P 303
Hu CRP       T S W E S A S G I V E F W V D G K - P R V R K S L K K G Y T V G 147
Hu SA-P      V S W E S S S G I A E F W I N G T - P L V K K G L R G G Y F V E 146

TSG-14       E G G I L Q I G Q E K N G C C V G G F D E T L A F S G R L T G 335
Hu CRP       A E A S I L G Q E Q D S - - F G G N F E G S Q S L V G D I G N 177
Hu SA-P      A Q P K I V L G Q E Q D S Y - - G G K F D R S Q S F V G E I G D 176

TSG-14       F N I W D S V L S N E E I R E T G G A E S C H I R G N I V G W G 367
Hu CRP       V N M W D F V L S P D E I N T I Y L G G P - - F S P N V L N W R 207
Hu SA-P      L Y M W D S V L P P E N I - - L S A Y Q G T P L P A N I L D W Q 206

TSG-14       V T E I Q P H G G A Q Y V S 381
Hu CRP       A L K Y E V Q G E V F T K P Q L W P 225
Hu SA-P      A L N Y E I R G Y V I I K P L V W V 224
```

FIG. 10

DNA ENCODING CYTOKINE-INDUCED PROTEIN, TSG-14

This application is a continuation of U.S. application Ser. No. 07/640,492, filed Jan. 14, 1991, now abandoned, the contents of which are herein entirely incorporated by reference,

BACKGROUND OF THE INVENTION

1. Field of the Invention

The invention relates to a protein, TSG-14, inducible in connective tissue cells by tumor necrosis factor or interleukin-1, DNA and mRNA encoding the TSG-14 protein, functional derivatives of the protein, antibodies specific to the protein, methods of producing the protein and DNA, and uses of the protein, DNA, mRNA, peptides and antibodies.

2. Description of the Background Art

Tumor necrosis factor (TNF) is a powerful pleiotropic cytokine important in host defenses against tumors and infectious agents. TNF has also been implicated in the pathology of some neoplastic diseases, infections and autoimmune disorders. Most biological actions of TNF can be attributed to the triggering of complex genetic programs in the target cells. Several genes activated by TNF have been identified but many more require characterization.

General Properties of TNF

TNF (also termed TNF-α and cachectin) is a protein produced by activated monocytes/macrophages which was originally detected in the serum of animals injected sequentially with a bacterial vaccine (bacillus Calmette-Guerin, BCG) and endotoxin (Carswell, E. A. et al., *Proc. Natl. Acad. Sci. USA* 72:3666 (1975)). TNF is structurally and functionally related to a cytokine produced by activated T lymphocytes which was originally termed lymphotoxin (LT) and is also known as TNF-β (Aggarwal, B. B. et al., *J. Biol. Chem.* 260:2334 (1985); Williams, T. W. et al., *Nature* 219:1076 (1968); Ruddle, N. H. et al., *J. Exp. Med.* 128:1267 (1968); Spies, T. et al., *Proc. Natl. Acad. Sci. USA* 83:8699 (1986); Gray, P. W. et al., *Nature* 312:721 (1984); Pennica, D. W. et al., *Nature* 312:724 (1984)). The genes encoding TNF and LT are linked, and are near the HLA-DR locus on the short arm of human chromosome 6 (Spies, T. et al., supra). TNF and LT bind to common cell surface receptors (Aggarwal, B. B. et al., *Nature* 318:665 (1985)).

Natural human TNF is a 157 amino acid, non-glycosylated protein with a molecular weight of approximately 17 kDa under denaturing conditions. The mature molecule is derived from a precursor (pre-TNF) which contains 76 additional amino acids at the N-terminus (Pennica, D. W. et al., supra). The expression of the gene encoding TNF is not limited to cells of the monocyte/macrophage family. Several human non-monocytic tumor cell lines were shown to produce TNF (Rubin, B. Y. et al., *J. Exp. Med.* 164:1350 (1986); Spriggs, D. et al., *Proc. Natl. Acad. Sci. USA* 84:6563 (1987)). TNF is also produced by CD4+ and CD8+ peripheral blood T lymphocytes, and by various cultured T and B cell lines (Cuturi, M. C., et al., *J. Exp. Med* 165:1581 (1987); Sung, S.-S. J. et al., *J. Exp. Med.* 168:1539 (1988)).

Accumulating evidence indicates that TNF is a regulatory cytokine with pleiotropic biological activities. These activities include: inhibition of lipoprotein lipase synthesis ("cachectin" activity) (Beutler, B. et al., *Nature* 316:552 (1985)), activation of polymorphonuclear leukocytes (Klebanoff, S. J. et al., *J. Immunol.* 136:4220 (1986); Perussia, B., et al., *J. Immunol.* 138:765 (1987)), inhibition of cell growth or stimulation of cell growth (Vilcek, J. et al., *J. Exp. Med.* 163:632 (1986); Sugarman, B. J. et al., *Science* 230:943 (1985); Lachman, L. B. et al., *J. Immunol.* 138:2913 (1987)), cytotoxic action on certain transformed cell types (Lachman, L. B. et al., supra; Darzynkiewicz, Z. et al., *Canc. Res.* 44:83 (1984)), antiviral activity (Kohase, M. et al., *Cell* 45:659 (1986); Wong, G. H. W. et al., *Nature* 323:819 (1986)), stimulation of bone resorption (Bertolini, D. R. et al., *Nature* 319:516 (1986); Saklatvala, J., *Nature* 922:547 (1986)), stimulation of collagenase and prostaglandin E2 production (Dayer, J.-M. et al., *J. Exp. Med.* 16.2:2163 (1985)), and other actions. For reviews of TNF, see Beutler, B. et al., *Nature* 230:584 (1986); Old, L. J., *Science* 230:630 (1986); and Le, J. et al., *Lab. Invest,* 56:234 (1987).

TNF also has immunoregulatory actions, including activation of T cells (Yokota, S. et al., *J. Immunol.* 140:531 (1988)), B cells (Kehrl, J. H. et al., *J. Exp. Med.* 166:786 (1987)), monocytes (Philip, R. et al., *Nature,* 323: 86 (1986)), thymocytes (Ranges, G. E. et al., *J. Exp. Med.* 167:1472 (1988)), and stimulation of the cell-surface expression of major histocompatibility complex (MHC) class I and class II molecules (Collins, T. et al.,*Proc. Natl. Acad. USA* 83:446 (1986); Pujol-Borrell, R. et al., *Nature* 326:304 (1987)).

TNF also has various pro-inflammatory actions which result in tissue injury, such as induction of procoagulant activity on vascular endothelial cells (Pober, J. S. et al., *J. Immunol.* 136, 1680, 1986)), increased adherence of neutrophils and lymphocytes (Pober, J. S. et al., *J. Immunol.* 138:3319 (1987)), and stimulation of the release of platelet activating factor (PAF) from macrophages, neutrophils and vascular endothelial cells (Camussi, G. et al., *J. Exp. Med.* 166:1390 (1987)). Recent evidence implicates TNF in the pathogenesis of many infections (Cerami, A. et al., *Immunol. Today* 9:28 (1988)), immune disorders (Piguet, P.-F. et al. *J. Exp. Med.* 166:1280 (1987)), and in cachexia accompanying some malignancies (Oliff, A. et al., *Cell* 50:555 (1987)). Michie, H. R. et al., *Br. J. Surg.* 76:670–671 (1989), reviewed evidence that TNF is the principal mediator associated with the pathological changes of severe sepsis.

TNF also has activity associated with growth and differentiation of hemopoietic precursor cells (Murphy, M. et al., *J. Exp. Med.* 164:263 (1986); Broxmeyer, H. E. et al., *J. Immunol.* 136:4487 (1986)); some of these actions may be indirect, and are thought to be mediated through the stimulation of production of granulocyte-macrophage colony stimulating factor (GM-CSF) (Munker, R. et al., *Nature* 323:79 (1986)) and other hemopoietic growth factors (Zucali, J. R. et al., *J. Immunol.* 140:840 (1988)).

Regulation of Gene Expression by TNF

It is, therefore, apparent that TNF is an extremely "versatile" and clinically significant cytokine. Most of its actions are likely to be mediated by the activation or inactivation of specific genes in the cells upon which it acts. One exception to this mode of action is the rapid cytotoxic effect of TNF on certain target cells; this effect is augmented by inhibitors of RNA or protein synthesis and does not appear to depend on the modulation of gene expression (Matthews, N., *Br. J. Cancer*

48:405 (1983)). Many specific gene products have been shown to be up-regulated in TNF-treated cells, some of which are discussed below.

Among the first examples of TNF-modulated gene expression was the demonstration that TNF treatment induced an increase in MHC class I mRNA levels and in surface expression of the MHC class I glycoproteins in human vascular endothelial cells (HUVEC) and normal skin fibroblasts (Collins, T. et al., supra). A partial list of other molecules (or genes) induced by TNF appears in Table 1, below. It is interesting to note that TNF is an autoregulatory cytokine, since exogenously added TNF increases TNF synthesis in monocytes and monocytic cell lines (Philip, R. et al., Nature 323:86 (1986); Schmid, J. et. al., *J. Immunol.* 139:250 (1987)).

TABLE 1

GENES AND PROTEINS INDUCED BY TUMOR NECROSIS FACTOR

| Protein or Gene | Cell Type | Ref |
|---|---|---|
| Leukocyte adhesion protein H4/18 | HUVEC | (1) |
| Platelet-derived growth factor (PDGF) | HUVEC and some tumor cell lines | (2) |
| IL-6 (IFN-$\beta$2 or BSF-2) | Human skin fibroblasts | (3) |
| HLA-DR | Human tumor cell lines | (4) |
| Collagenase | Synovial cells and skin fibroblasts | (5) |
| 2'-5' oligoadenylate synthetase | Tumor cell lines | (6) |
| c-yc and c-fos oncogenes | Human skin fibroblasts | (7) |
| Epidermal growth factor receptor | Human skin fibroblasts | (8) |
| Tissue factor | HUVEC | (9) |
| ICAM-1 and ELAM-1 | HUVEC | (10) |
| Plasminogen activator inhibitors 1 and 2 (PAI-1 and PAI-2) | HT1080 cell line | (11) |
| Synthesis of 36 kDa and 42 kDa (=PAI-2) proteins | Human skin fibroblasts | (12) |
| Superoxide Dismutase (MnSOD) gene | Human tumor cell lines | (13) |
| IL-1$\alpha$ and IL-1$\beta$ genes | Human skin fibroblasts | (14) |

REFERENCES:
1. Pober, J.S. et al., J. Immunol. 136, 1680, 1986.
2. Hajjar, K.A. et al., J. Exp. Med. 166, 235, 1987.
3. Kohase, M. et al., Cell 45:659 (1986).
4. Pfizenmaier, K. et al, J. Immunol. 138, 975, 1987.
5. Dayer, J.-M. et al, J. Exp. Med, 162:2163 (1985).
6. Wong, G.H.W. et al., Nature 323:819 (1986).
7. Lin, J.-X. et al., J. Biol. Chem. 262, 11908, 1987.
8. Palombella, V.J. et al., J. Biol. Chem. 262, 1950, 1987.
9. Edgington, T.S. et al., Abs. 2nd Internat. Conf. TNF, p. 4, 1989.
10. Bevilacqua, M.P. et al., Proc. Natl. Acad. Sci. USA 84, 9238, 1987.
11. Medcalfe, R.L. et al., J. Exp. Med, 168, 751, 1988.
12. Kirstein, M. et al., J. Biol. Chem. 261, 9565, 1986.
13. Wong, G.H. et al., Science 242, 941, 1988.
14. Le, J. et al. Lab. Invest. 56:234 (1987).

The inhibitory actions of TNF on gene expression are less well-characterized. TNF was shown to inhibit c-myc expression in cells whose growth it inhibited (Kronke, M. et al., *Proc. Natl. Acad. Sci, USA* 84:469 (1987)). Collagen synthesis was inhibited in human fibroblasts (Solis-Herruzo et al., *J. Biol, Chem.* 263:5841 (1988)), and thrombomodulin in HUVEC (Conway, E. M. et al., *Molec. Cell, Biol.* 8:5588 (1988)). All these inhibitory actions were expressed at the level of transcriptions but the precise mechanisms are still unclear.

The mechanisms of signal transduction and gene activation by TNF are the subject of great interest. In many cell types, TNF activates a phospholipase (most likely PLA2), resulting in the liberation of arachidonic acid from cellular pools (Suffys, P. et al., *Biochem. Biophys. Res. Comm.* 149:735 (1987)) and increased eicosanoid synthesis (Dayer, J.- M. et al., supra). In human fibroblasts, TNF stimulated GTPase activity (Imamura, K. et al. *J Biol. Chem.* 263:10247 (1989)), raised cAMP levels, enhanced cAMP-dependent protein kinase activity, and activated protein kinase C (PKC) (Zhang, Y. et al., *Proc. Nature Acad. Sci. USA* 85:6802 (1988); Brenner, D. A. et al., *Nature* 337:661 (1989)). TNF can also activate the transcription factor NF-kB, which appears to be the mechanism by which TNF induces the IL-2 receptor $\alpha$ chain (Lowenthal, J. W. et al., *Proc. Natl. Acad. Sci. USA* 86:2231 (1989)) or cause activation of latent human immunodeficiency virus, HIV-1 (Griffin, G. E. et al., *Nature* 339:70 (1989)).

Interactions of TNF with other Cytokines

When the individual actions of TNF-$\alpha$, TNF-$\beta$, IL-1$\alpha$, IL-1$\beta$, IFN-$\alpha$, IFN-$\beta$ or IFN-gamma are compared in various experimental systems, a great deal of apparent redundancy and ambiguity is noted. First, structurally related cytokines which utilize the same receptor (e.g., TNF-$\alpha$ and TNF-$\beta$; IL-1$\alpha$ and IL-1$\beta$; IFN-$\alpha$ and IFN-$\beta$) act similarly. More surprisingly, structurally unrelated cytokines which bind to different receptors also have similar physiological effects. For example, IL-1 and TNF have similar gene activating activities, and result in similar biological effects (Le, J. et al. *Lab. Invest.* 56:234 (1987)). IFNs and TNF also share biological activities (Kohase, M. et al., *Cell* 45:659 (1986); Wong, G. H. W. et. al., *Nature* 323:819 (1986); Williamson, B. D. et al., *Proc. Natl. Acad. Sci. USA* 80:5397 (1983); Stone-Wolff, D. S. et al., *J. Exp. Med.* 159:828 (1984)). For example, IFNs and TNF activate some of the same genes, including MHC class I and class II genes, 2'-5' oligoadenylate synthetase, IL-6, the transcription factor IRF-1, and the TNF gene itself (Vilcek, J., *Handbook of Experimental Pharmocology*, Vol. 95/II, p. 3, Springer-Verlag, Berlin (1990)).

Under natural conditions cells are rarely, if ever, exposed to a single cytokine. Rather, cytokine action in vivo is "contextual," as has been postulated for growth factors (Sporn, M. B. et al., *Nature* 332:217 (1988)). The biological effects produced by cytokines under natural conditions must therefore represent the sum of the synergistic and antagonistic interactions of all cytokines present simultaneously in a given microenvironment. In addition, cytokines appear to be arranged in "networks" and "cascades", such that the synthesis of one cytokine can be positively or negatively regulated by another. For these reasons, it is important to understand the molecular mechanisms of action of cytokines acting individually as well as in combination.

In contrast to the above, there are cases in which the actions of TNF and IFNs are antagonistic rather than similar or synergistic. For example, TNF is mitogenic for human diploid fibroblasts, whereas IFNs inhibit growth of these cells (Vilcek, J. et al., *J. Exp. Med.* 163:632 (1986)). The cellular response to a combination of TNF and an IFN can differ from the response to either one alone, both qualitatively and quantitatively (Leeuwenberg, J. F. M. et al., *J, Exp. Med.* 166:1180 (1987); Reis, L. F. L. et al., *J. Biol. Chem.* 264:16351 (1989); Feinman, R. et al., *J. Immunol.* 136:2441 (1986); Trinchieri, G. et al., *Abstr. 2nd Int'l Conf. TNF*, p. 7 (1989)). To make matters even more complicated, in some cells TNF can induce IFN-$\beta$ synthesis (Reis et al., supra); the activation of some genes (e.g., HLA class I) by TNF requires the presence of IFN-$\beta$ (Leeuwenberg et al., supra). Since IFNs and TNF-$\alpha$ and TNF-$\beta$ are often produced in the same microenvironment in response to a similar set of stimuli (Murphy, M. et al., supra; Stone-Wolff et al., supra; Billiau, A., *Immunol Today* 9:37 (1988)), it is clear that the interactions of TNF and IFNs are highly relevant to the outcome in vivo under either "normal" or pathophysiological conditions.

The association of cytokines, in particular TNF, with cancer and infectious diseases takes many forms often related to the host's catabolic state. One of the major and most characteristic problems seen in cancer patients is weight loss, usually associated with anorexia. The extensive wasting which results is known as "cachexia" (see, for review, Kern, K. A. et al. (*J. Parent. Enter. Nutr.* 12:286-298 (1988)). Cachexia includes progressive weight loss, anorexia, and persistent erosion of body mass in response to a malignant growth. The fundamental physiological derangement may be related to a decline in food intake relative to energy expenditure. The causes for this commonly observed and often life-limiting disturbance remain to be determined, even though many contributing factors have been identified (Braunwald, E. et al. (Eds.), Harrison's PRINCIPLES OF INTERNAL MEDICINE, 11th Ed., McGraw-Hill Book Co., New York, 1987, Chap. 78, pp. 421-431). The cachectic state is associated with significant morbidity and is responsible for the majority of cancer mortality. A number of studies have suggested that TNF is an important mediator of the cachexia in cancer, infectious disease, and in other catabolic states.

It has been known for some time that in bacterial infection, sepsis and critical illness, bacterial lipopolysaccharides (LPS), or endotoxins, are responsible for many of the pathophysiological manifestations, including fever, malaise, anorexia, and cachexia. More recently, it was observed that TNF can mimic many endotoxin effects, leading to the suggestion that TNF, and related cytokines derived from cells of the macrophage/monocyte family, in particular, In-1, are central mediators responsible for the clinical manifestations of the illness. Endotoxin is a potent monocyte/macrophage activator which stimulates production and secretion of TNF (Kornbluth, S. K. et al., *J. Immunol.* 137:2585-2591 (1986)) and other cytokines including IL-1 (Dinarello, C. A., *Rev. Infec. Dis.* 6:51-94 (1984)), interleukin-6 (IL6), and colony stimulating factor (CSF) (Apte, R. N. et al., *J. Cell. Physiol.* 89:313 (1976)). Some of these cytokines further stimulate T lymphocytes to produce additional cytokines, for example, interleukin-2 (In-2) (Robb, R. J., *Immunol. Today* 5:203-209 (1984)).

The monocyte-derived cytokines are thought to be important mediators of the metabolic and neurohormonal responses to endotoxin (Michie, H. R. et al., *N. Eng. J. Med.* 318:1481-1486 (1988)), and in cancer and other catabolic states (Norton, J. A. et al., *Nutrition* 5:131-135 (1989)). Interestingly, some changes induced by low-dose TNF closely resemble changes provoked by high dose IL2 (Remick, D. G. et al., *Lab, Invest.* 56:583-590 (1987)).

Endotoxin administration to human volunteers produced acute illness with flu-like symptoms including fever, tachycardia, increased metabolic rate and stress hormone release (Revhaug, A. et al., *Arch, Surg.* 123:162-170 (1988)). Treatment of cancer patients (having normal kidney and liver function) with escalating doses of TNF (4-636 μg/m²/24 hr) indicated that doses greater than 545 μg/m²/24hr caused alterations similar to those induced by injection of endotoxin (4 ng/kg) into healthy humans (Michie, H. R. et al., *Surgery* 104:280-286 (1988)), leading the authors to conclude that TNF is the principal host mediator of septic and endotoxemic responses. More recently, it was shown that five days of chronic intravenous TNF infusion into humans or rats was associated with anorexia, fluid retention, acute phase responses, and negative nitrogen balance (i.e., classic catabolic effects), leading to the conclusion that TNF may be responsible for many of the changes noted during critical illness (Michie, H. R. et al., *Ann. Surg.* 209:19-24 (1989)). Administration of rTNF to cancer patients also led to a rise in C-reactive protein (CRP) and a fall in serum zinc, a large increase in forearm efflux of total amino acids, and amino acid uptake by other tissues (Warren, R. S. et al., *Arch. Surg.* 122:1396-1400 (1987)), considered further evidence for a role of TNF in cancer cachexia.

The cytokine tumor necrosis factor-$\alpha$ (TNF)$_2$ was first described as a mediator of hemorrhagic necrosis of certain transplanted tumors in mice (Carswell et ales 1975 *Proc. Natl. Acad. Sci. USA,* 72:3666).

Citation of documents herein is not intended as an admission that any of the documents cited herein is pertinent prior art, or an admission that the cited documents is considered material to the patentabilty of the claims of the present application. All statements as to the date or representation as to the contents of these documents is based on the information available to the applicant and does not constitute any admission as to the correctness of the dates or contents of these documents.

SUMMARY OF THE INVENTION

Cytokines such as TNF and IL-1 play a major role in the mediation of inflammatory responses as well as in host responses to infections and cancer. The present inventors have discovered and studied a series of proteins and glycoproteins induced in connective tissue cells by such cytokines. The present inventors have conceived of the use of such cytokine-induced proteins or glycoproteins, termed TSG proteins or polypeptides, or functional derivatives derived therefrom, and antibodies specific for these TSG proteins/glycoproteins, for a number of diagnostic and therapeutic procedures. These proteins, the DNA coding therefor, and the functional derivatives thereof, are useful in the treatment, diagnosis or study of a number of pathologies or diseases associated with action of the above types of cytokines, including chronic inflammatory conditions, in particular rheumatoid arthritis, infections, sepsis and/or in cancer.

Specifically, the present invention provides a cytokine-induced polypeptide, protein or glycoprotein molecule, termed TSG-14, or a functional derivative thereof, wherein, when the protein molecule is one which naturally occurs, is provided in a form not found in nature. The full length protein molecule has an apparent molecular weight of about 40-42 kDa, including the probable signal sequence, the molecular weight of the mature protein is about 40 kDa. The TSG-14 protein has the amino acid sequence SEQ ID NO:4 (FIG. 9A), or comprises the the N-terminal amino acid sequence of amino acids 1-153 of SEQ ID NO:1(FIG. 4).

The present invention is further directed to a TSG-14 DNA or TSG-14 nucleic acid encoding a TSG-14 polypeptide, as a TSG-14, or a TSG-14 functional derivative, wherein when the DNA molecule occurs naturally, it is substantially free of other nucleotide sequences with which it is natively associated. The DNA molecule hybridizes to a complementary nucleotide sequence to a 10 to 1143 nucleotide DNA sequence corresponding to SEQ ID NO:4 or SEQ ID NO:1, and encodes a TSG-14 polypeptide having the biological activity of being induced by at least one known cytokine. A TSG-14 polypeptide may have a nucleotide sequence substantially corresponding to a nucleotide sequence of SEQ ID NO:1 or SEQ ID NO:4.

A TSG-14 nucleic acid or DNA of the present invention may be genomic DNA, RNA or cDNA, and it may be single stranded or double stranded.

The present invention provides a DNA or RNA molecule as an expression vehicle, such as a plasmid, and provides host cells transformed or transfected with the DNA molecule. Hosts may be bacteria or eukaryotic cells, including yeast and mammalian cells.

Also included in the present invention is a process for preparing the TSG-14 protein or glycoprotein molecule substantially free of other proteins or glycoproteins with which it is natively associated, or a functional derivative thereof, comprising: (a) culturing a host cell capable of expressing the protein under culturing conditions, (b) expressing the protein or functional derivative; and (c) recovering the protein or functional derivative from the culture.

The present invention is also directed to an antibody specific for the TSG-14 protein or an epitope thereof. A preferred antibody is a monoclonal antibody.

Also provided is a method for detecting the presence of TSG-14 protein in a biological sample, comprising: (a) contacting the biological sample that is suspected of containing TSG-14 protein with a molecule capable of binding to the protein; and (b) detecting any of this molecule bound to the protein, For this method, a preferred molecule is an antibody or antibody fragment, most preferably a monoclonal antibody, and the preferred detection method is an immunoassay.

The present invention further includes a method for detecting the presence of nucleic acid encoding a normal or mutant TSG-14 protein in a subject comprising: (a) contacting a cell obtained from the subject, an extract thereof, or a culture supernatant thereof, with an oligonucleotide probe encoding at least a portion of the normal or mutant TSG-14 under hybridizing conditions; and (b) measuring the hybridization of this probe to the nucleic acid of the cell, thereby detecting the presence of the nucleic acid. This method may additionally include, before step (a), selectively amplifying the amount of DNA of the cell encoding the TSG-14 protein.

The present invention is still further directed to a method for measuring induction of expression of TSG-14 in a cell, comprising: (a) contacting the cell with a substance capable of inducing expression of TSG-14; (b) measuring the amount of mRNA encoding TSG-14 in the cell by hybridization with an oligonucleotide probe encoding at least a portion of TSG-14, under hybridizing conditions; and (c) comparing the amount of TSG-14 mRNA in the cell with the amount of TSG-14 mRNA in the cell not contacted with the inducing substance, wherein an increase in the amount of the TSG-14 mRNA indicates that the induction has occurred.

An alternative method for measuring induction of expression of TSG-14, according to the present invention comprises: (a) contacting the cell with a substance capable of inducing expression of TSG-14; (b) measuring the amount of TSG-14 protein in an extract or supernatant of the cell using the method described above for measuring the TSG-14 protein, preferably, an immunoassay; and (c) comparing the amount of TSG-14 protein in the cell extract or supernatant with the amount of TSG-14 protein in the extract or supernatant of a cell not contacted with the inducing substance, wherein an increase in the amount of the TSG-14 protein indicates that the induction has occurred.

The present invention may also be used in a method for identifying a compound capable of inducing the expression of TSG-14 in a cell, comprising: (a) contacting the cell with the compound being tested; and (b) measuring the induction of TSG-14 mRNA according to one of the two methods described above, thereby identifying the compound.

The present invention also provides a method for measuring the ability of a cell to respond to TNF or to IL-1, comprising: (a) contacting the cell with an amount of TNF capable of inducing expression of the TSG-14 gene in FS-4 cells, and (b) determining the induction of expression of TSG-14 mRNA or protein using either of the methods described above, thereby measuring the ability of the cell to respond to TNF.

BRIEF DESCRIPTION OF THE DRAWINGS

FIG. 4 shows the cDNA and amino acid sequence of TSG-14 (SEQ ID NO:1). The hydrophobic signal sequence and the polyadenylation signals are underlined.

FIGS. 9A and 9B cDNA and deduced amino acid sequence of TSG-14 (SEQ ID NO:4). FIG. 9A; Nucleotide and amino acid residues are numbered from the first methionine of the major open reading frame. Both the putative signal peptide sequence and the N-glycosylation site are underlined. The 3' poly-adenylation signal and the pentaxin sequence motif are indicated by double underlines. The cDNA sequence has been submitted to the GenBank, EMBL, and DDBJ nucleotide sequence database under the accession number M31166. FIG. 9B; Hydropathic profile of the deduced amino acid sequence of TSG-14 using the algorithm of Kyte and Doolittle (1982, J. Mol. Biol. 157:105.).

FIG. 10. Alignment of the COOH-terminal half of the TSG-14 (SEQ ID NO:4) protein (residues 180–381 of SEQ ID NO:4) with human C-reactive protein (CRP) (SEQ ID NO:3) and human serum amyloid-P component (SAP) (SEQ ID NO:5). Conserved residues are boxed.

FIG. 11A: TSG-14 cDNA was cloned into the vector pGEM7zf(+) (Promega, Madison, Wis.) and linearized as shown in the figure. The linearized plasmids were transcribed/translated in vitro and the products analyzed by SDS-PAGE and autoradiography. FIG. 11B: Autoradiograph of in vitro translated products separated by SDS-PAGE. Lane 1, SacII deletion product; lane 2, NdeI deletion product; lane 3, BamHI deletion product made in rabbit reticulocyte lysate. To analyze translocation into microsomes and post-translational processing of the TSG-14 protein, the BamHI transcript was translated in vitro in the presence of canine pancreatic microsomes (lanes 4–7). Lane 4, the reaction mixture was treated with N-glycosidase F for 1 h at 37° C.; lane 5, untreated control; lane 6, reaction mixture was incubated with proteinase K; lane 7, reaction mixture was incubated with proteinase K and Triton X-100; lane 8, blank control in which no DNA was present in the initial in vitro transcription reaction.

DETAILED DESCRIPTION OF PREFERRED EMBODIMENTS

Figure 1A:
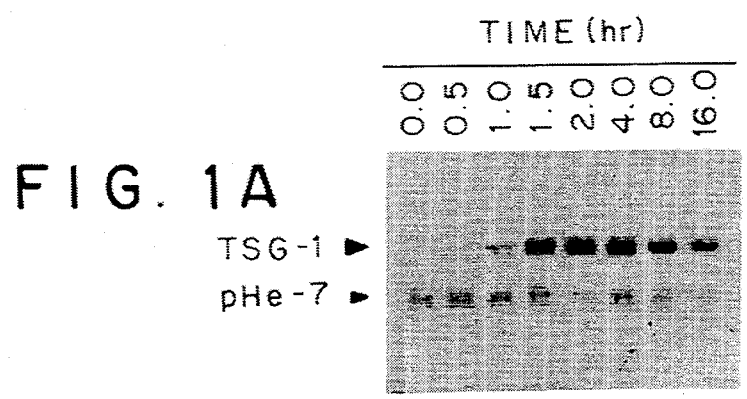
FIGS. 1A–1H depicts Northern blots showing induction of mRNAs corresponding to eight TSG cDNAs in FS-4 cells treated with TNF. Growth-arrested FS-4 cells were exposed to TNF (20 ng/ml) at 0 h. At different intervals thereafter, total cell RNA was isolated, fractionated on formaldehyde-agarose gels, transferred to Zeta-probe blotting membranes, and hybridized separately to each of the $^{32}$P-labeled TSG cDNA inserts. To ascertain whether equal amounts of RNA were loaded in each lane, most blots were also probed with a $^{32}$P-labeled pHe7 internal reference cDNA insert specific for an invariant mRNA species of about 1.0 kb.
Figure 1B:
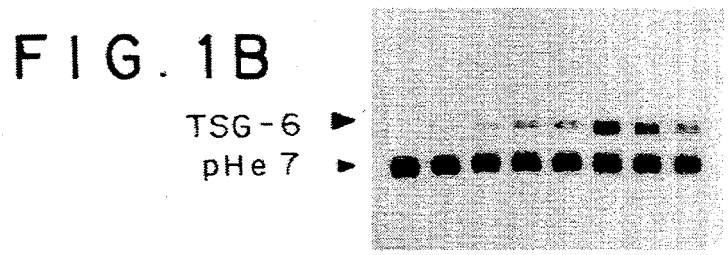
Figure 1C:
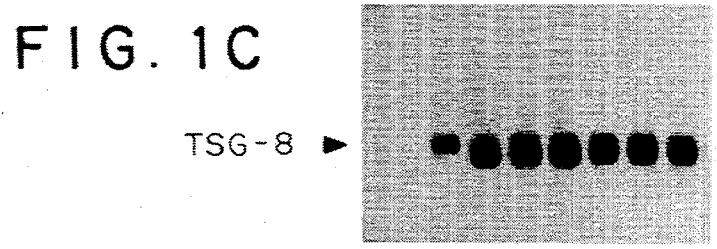
Figure 1D:
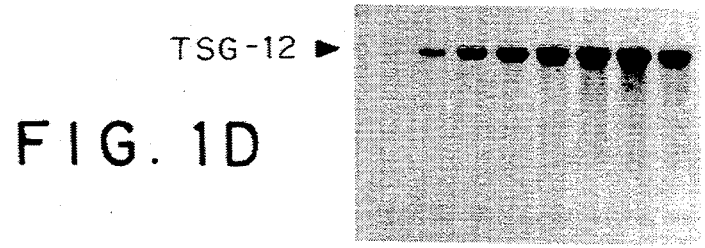
Figure 1E:
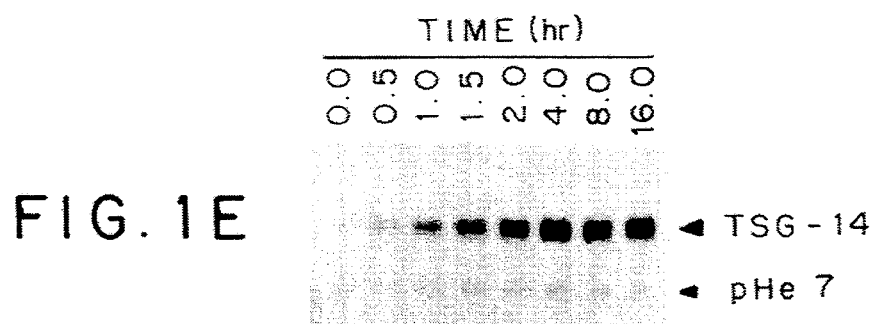
Figure 1F:
Figure 1G:
Figure 1H:
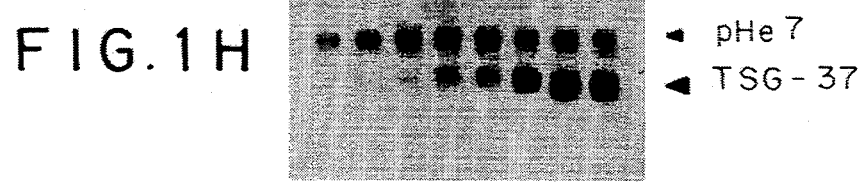
Figure 2A:
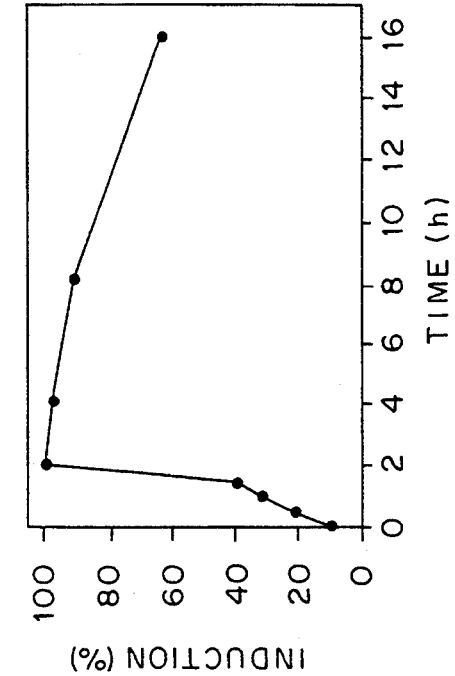
FIGS. 2A–2H is a series of graphs showing the kinetics of induction of eight TSG mRNAs by TNF. Autoradiograms of the Northern blots shown in FIG. 1 were scanned by laser densitometry. For each individual mRNA, the highest-density band was normalized to represent 100% induction.
Figure 2B:
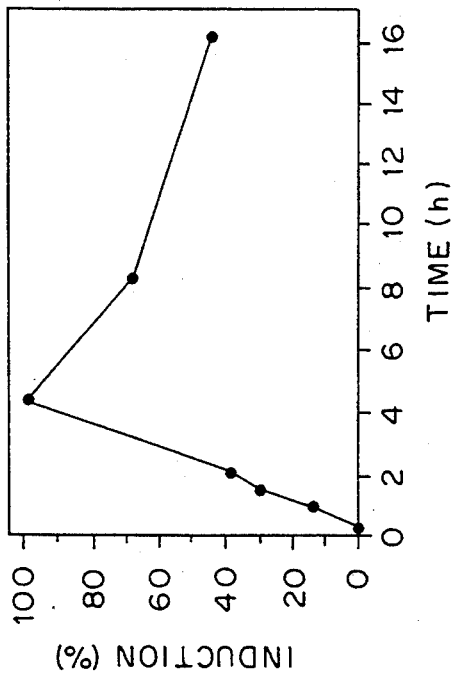
Figure 2C:
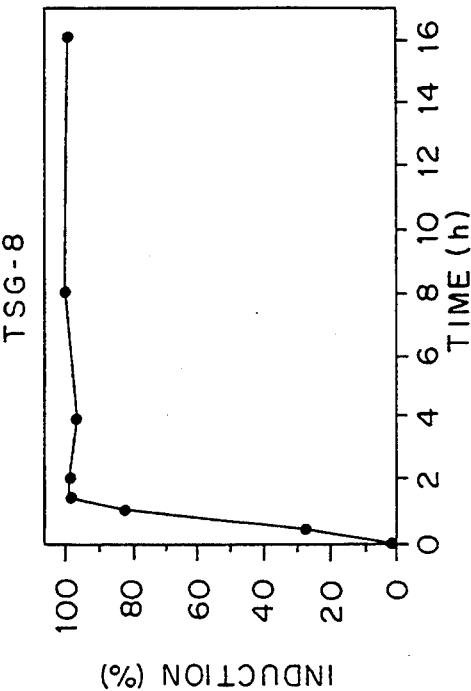
Figure 2D:
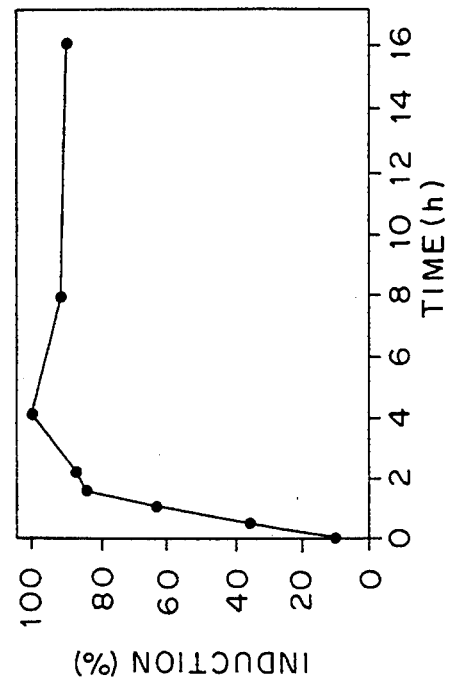
Figure 2E:
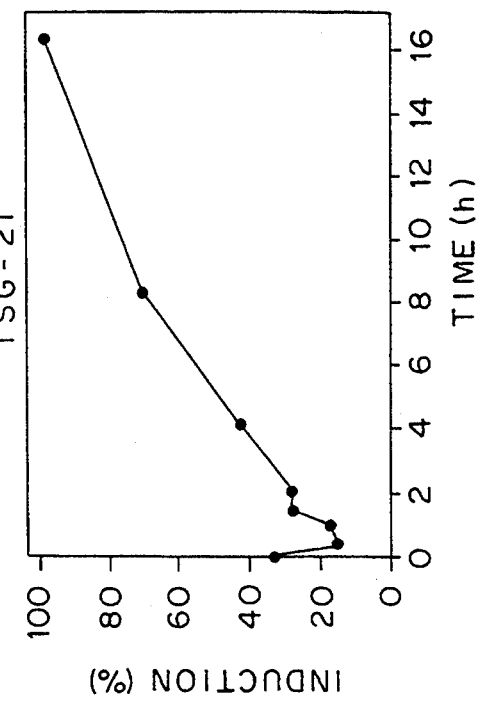
Figure 2F:
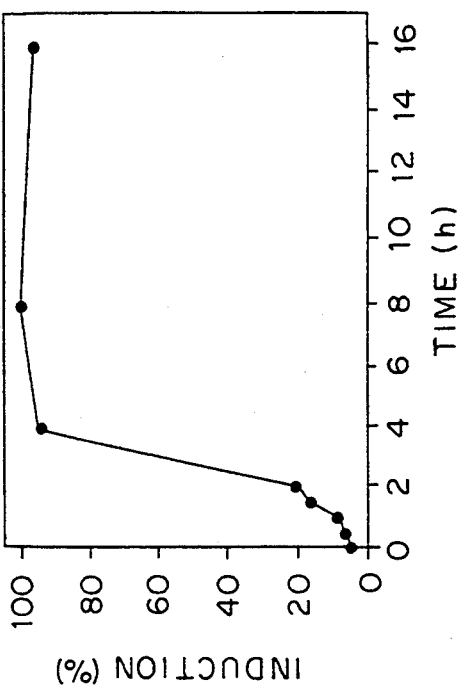
Figure 2G:
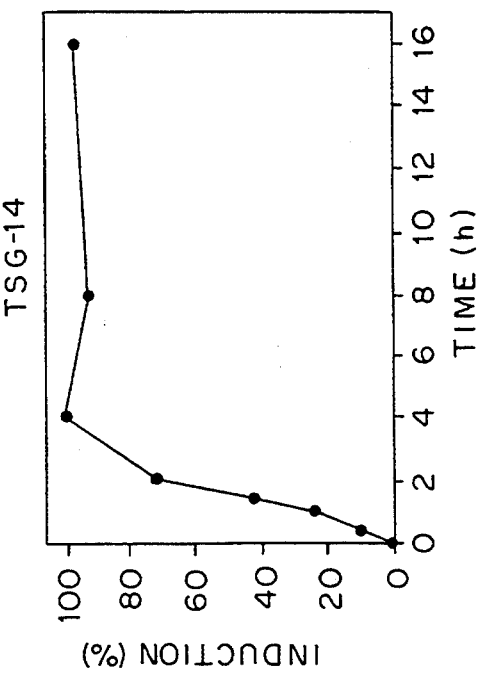
Figure 2H:
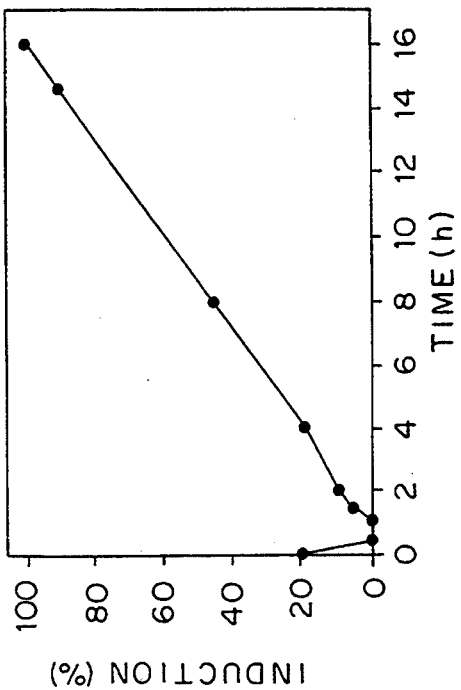

According to the present invention, the full-length TSG-14 cDNA had been isolated and sequenced. The largest open reading frame encodes a protein with a predicted molecular weight of approximately 40–42 kDa, including a cleavable signal peptide. Ability of TSG-14 cDNA to encode a protein was confirmed in a cell-free transcription/translation system; the translation product had the predicted molecular size, and its translocation into microsomes in vitro confirmed the prediction that TSG-14 is a secretory protein. The predicted sequence of TSG-14 protein (SEQ ID NO:4) shows partial homology with C reactive protein (CRP) (SEQ ID NO:5) and serum amyloid P component (SAP) (SEQ ID NO:5), members of the pentaxin family of acute phase proteins (Woo et al., 1985, J. Biol. Chem., 260:13384.; Oliveira et al., 1977, Proc. Natl. Acad. Sci. USA, 74:3148; Mantzouranis et al., 1985, J. Biol. Chem. 260:7752.). TSG-14 is a newly identified member of the pentaxin family of acute phase proteins is also supported by the characteristic pattern of induction of TSG-14 mRNA by treatments with TNF, IL-I, dexamethasone, and IL-6. Interestingly, TSG-14 protein is almost twice the size of CRP and SAP, and the N-terminal half of TSG-14 protein revealed no sequence homology to other known proteins.

This feature suggests that TSG-14 protein could have biological functions quite different from those of CRP and SAP. The latter two proteins are characteristically produced in response to a variety of infections or other injuries (Gordon and Koj, 1985, The acute-phase response to injury and infection. Elsevier Science Publishers B. V., The Netherlands.), and they are thought to play a protective role by interacting with the complement system (Kaplan and Volonakis, 1974, J. Immunol. 112:2135.; Jiang, et al., 1991, J. Immunol. 146:2324.), and by promoting clearance of foreign material from the circulation (Gordon and Koj, 1985, The acute-phase response to injury and infection. Elsevier Science Publishers B.V., The Netherlands.). Identification of TSG-14 opens the way to the elucidation of the functions of this novel acute phase protein.

The cytokine tumor necrosis factor-$\alpha$ (TNF)$_2$ was first described as a mediator of hemorrhagic necrosis of certain transplanted tumors in mice (Carswell et al., 1975 *Proc. Natl. Acad. Sci. USA*, 72:3666). It is now clear that TNF exerts a wide range of biological effects and is important as a mediator of host defenses against infectious agents and malignancies (reviewed in Beutler and Cerami, 1986 *Nature* (London), 337:661; Aggarwal and Vilcek (Eds.) 1992. Tumor necrosis factors: Structure, function, and mechanism of action. Marcel Dekker, Inc., New York.; and Beutler (Ed.) 1992. Tumor necrosis factors: The molecules and their emerging role in medicine. Raven Press, New York). Along with IL-1 and IL-6, TNF is an important mediator of the inflammatory and acute phase responses (Balkwill, 1989. Cytokines in cancer therapy. Oxford University Press, Oxford, UK.). Most of the actions of TNF and other cytokines can be attributed to the induction of specific genes in target cells (Vilcek and Lee, 1991, *J. Biol. Chem.*, 266:7313.). Earlier, we described several cDNAs corresponding to mRNAs upregulated by TNF; these cDNAs were isolated by differential screening from a cDNA library derived from normal human FS-4 fibroblasts that were treated with TNF (Lee et al., 1990, *Mol. Cell. Biol.*, 10:1982.). Three of the cDNAs isolated share no significant sequence homology with genes available from databanks, indicating that they represent hitherto unknown gene sequences. One of these novel genes, termed TSG-6 (TSG=TNF-stimulated gene), was recently shown to encode a secreted hyaluronate binding protein, structurally related to members of the cartilage link protein family (Lee et al., 1992, *J. Cell. Biol.*, 116:545.). Another novel cDNA identified from the same library, termed TSG-14, corresponds to an mRNA whose levels are undetectable in untreated FS-4 fibroblasts but rise dramatically upon stimulation with TNF (Lee et al., 1990, *Mol. Cell. Biol.*, 10:1982.). TSG-14 mRNA was also found to be inducible by IL-1, and to a lesser degree by cycloheximide, epidermal growth factor (EGF), platelet-derived growth factor (PDGF), double-stranded RNA, and the phorbol ester 12-O-tetradecanoyl phorbol 13-acetate, but not by interferons, transforming growth factor-$\beta$, and several other agents (Lee et al., 1990, *Mol. Cell. Biol.*, 10:1982.).

A number of genes activated in human FS-4 fibroblasts by tumor necrosis factor (TNF) were termed by the present inventors "TNF-stimulated genes" (abbreviated TSG). It should be appreciated that such genes, and the proteins and glycoproteins they encode, are induced by cytokines more generally, including TNF and IL-1. The proteins, functional derivatives, such as peptide fragments, and antibodies to the proteins are useful in a number of methods of importance to the diagnosis and treatment of diseases and conditions in which the activity, or inactivity, of such cytokines is associated with the pathophysiology. Such diseases include chronic inflammation, such as rheumatoid arthritis, cancer, and infections, in particular with gram-negative bacteria.

The present invention is directed to a TSG-14 polypeptide comprising an amino acid sequence substantially corresponding to a 10 to 1143 nucleotide coding sequence sequence of SEQ ID NO:4 (FIG. 9A), which first 153 amino acids correspond to SEQ ID NO:1. The amino acid sequence of these genes and its protein product, are both termed TSG-14 (SEQ ID NO:4). The present invention provides TSG-14 DNA, mRNA and protein in substantially pure form, functional derivatives of the protein such as peptide fragments, antibodies specific for the protein, methods of producing the DNA, mRNA and protein, methods of using these molecules.

"Substantially corresponding" refers to an amino acid or nucleic acid sequence having some biological activity corresponding to a cytokine induced protein. Alternatively, this term refers to an amino acid or nucleic acid sequence having at least 80% homology to a 1 to 301 amino acid sequence or 1 to 1143 nucleic acid sequence of SEQ ID NO:4 (FIG. 9A), such as 80, 81, 82, 83, 84, 85, 86, 87, 88, 89, 90, 91, 92, 93, 94, 95, 96, 97, 98, 99 or 100%.

By "substantially pure" is meant any protein or peptide of the present invention, or any DNA or mRNA sequence encoding any such protein or peptide, which is essentially free of other proteins, DNA sequences or mRNA sequences, respectively, or of other contaminants with which it might normally be found in natured and, as such, exists in a form not found in nature.

"Substantially free of other proteins" indicates that the protein has been purified away from at least 90 per cent (on a weight basis), and from even at least 99 per cent, if desired, of other proteins and glycoproteins with which it is natively associated, and is therefore substantially free of them. That can be achieved by subjecting the cells, tissue or fluids expressing or containing the TSG-14 protein to protein purification techniques such as immunoadsorbent columns bearing antibodies, such as monoclonal antibodies (mAb) reactive against the protein. Alternatively, the purification can be achieved by a combination of standard methods, such as ammonium sulfate precipitations molecular sieve chromatography, and ion exchange chromatography.

The methods of the present invention are used to identify normal or mutant TSG-14 genes or measure the presence or amount of TSG-14 protein associated with a cell or tissue, or secreted by a cell; such methods can serve as methods for identifying susceptibility to inflammatory conditions and to sepsis following gram-negative bacterial infections.

In one embodiments the invention is directed to a naturally occurring TSG-14 protein or glycoprotein substantially free from impurities of human origin with which it is natively associated. In another embodiment, the invention is directed to a recombinant TSG-14 encoded protein or glycoprotein.

It will be understood that the TSG-14 protein of the present invention can be purified biochemically or physicochemically from a variety of cell or tissue sources. For preparation of naturally occurring TSG-14 protein, connective tissue cells such as human fibroblasts are preferred. Alternatively, methods are well known for the synthesis of polypeptides of desired sequence on solid phase supports and their subsequent separation from the support.

Because the TSG-14 gene can be isolated or synthesized, the TSG-14 polypeptide, or a functional derivative thereof, can be synthesized substantially free of other proteins or glycoproteins of mammalian origin in a prokaryotic organism or in a non-mammalian eukaryotic organism, if desired. As intended by the present invention, a TSG-14, polypeptide, protein or glycoprotein molecule produced by chemical synthesis or by recombinant means in eukaryotic cells or organisms, such as transfected GM637 cells, for example, is either a naturally occurring protein sequence or a functional derivative thereof. Where a naturally occurring protein or glycoprotein is produced by recombinant means, it is provided is an isolated form not found in nature.

A preferred use of this invention as a TSG-14 polypeptide is the production by chemical synthesis or recombinant DNA technology of fragments of, or polypetides having at least 80% homology to, the TSG-14 molecule, which still retain biological activity such as binding to antibodies, and the like. Among the advantages of shorter peptides for some of the methods of the present invention are (1) greater stability and diffusibility, and (2) less immunogenicity. As discussed herein, the TSG-14 proteins or peptides of the present invention may be further modified for purposes of drug design, such as, for exampled to reduce immunogenicity, to promote solubility or enhance delivery, or to prevent clearance or degradation.

Also included within the scope of the resent invention are soluble forms of the TSG-14 protein, and functional derivatives of the TSG-14 protein having similar bioactivity for all the uses described herein. Also intended are all active forms of TSG-14 derived from the TSG-14 transcript, and all muteins with TSG-14 activity.

By "functional derivative", or "TSG-14 polypeptide", is meant a "fragment," "variant," "analog," or "chemical derivative" of the TSG-14 protein. A functional derivative retains at least a portion of the function of the TSG-14 protein which permits its utility in accordance with the present invention.

A "fragment" of the TSG-14 protein is any subset of the molecule, that is, a shorter peptide.

A "variant" of the TSG-14 refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., *DNA* 2:183 (1983)) of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

In general, site-directed mutagenesis in accordance herewith is performed by first obtaining a single-stranded vector that includes within its sequence a DNA sequence that encodes-the relevant peptide. An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence in the second strand bears the desired mutation. This heteroduplex vector is then used to transform appropriate cells and clones are selected that include recombinant vectors bearing the mutated sequence arrangement.

The mutated protein region may be removed and placed in an appropriate vector for protein production, generally an expression vector of the type that may be employed for transformation of an appropriate host.

Alternatively, the DNA encoding a normal or variant TSG-14 protein can be altered by homologous recombination, a technique developed within the past few years for targeting genes to induce or correct mutations in transcriptionally active genes (Kucherlapati, *Prog. in Nucl. Acid Res, and Mol. Biol.* 36:301 (1989)). The technique of homologous recombination was developed as a method for introduction of specific mutations into specific regions of the mammalian genome (Thomas et al., *Cell*, 44:419–428, 1986; Thomas and Capecchi, *Cell* 51:503–512 (1987); Doetschman et al., Proc. Natl. Acad. Sci. USA 85:8583–8587 (1988)) or to correct specific mutations within defective genes (Doetschman et al., *Nature* 330:576–578 (1987)). The above references to homologous recombination are hereby entirely incorporated by reference.

An example of a terminal insertion includes a fusion of a signal sequence, whether heterologous or homologous to the host cell, to the N-terminus of the peptide molecule to facilitate the secretion of mature peptide molecule from recombinant hosts.

Another group of variants are those in which at least one amino acid residue in the peptide molecule, and preferably, only one, has been removed and a different residue inserted in its place. Such substitutions preferably are made in accordance with the following list when it is desired to modulate finely the characteristics of a peptide molecule.

| Original Residue | Exemplary Substitutions | Original Residue | Exemplary Substitutions |
|---|---|---|---|
| Ala | Gly; | Ser Leu | Ile; Val |
| Arg | Lys | Lys | Arg; Gln; Glu |
| Asn | Gln; His | Met | Leu; Tyr; Ile |
| Asp | Glu | Phe | Met; Leu; Tyr |
| Cys | Ser | Ser | Thr |
| Gln | Asn | Thr | Ser |
| Glu | Asp | Trp | Tyr |
| Gly | Ala; Pro | Tyr | Trp; Phe |
| His | Asn; Gln | Val | Ile; Leu |
| Ile | Leu; Val | | |

Substantial changes in functional or immunological properties are made by selecting substitutions that are less conservative than those in the above list, that is, by selecting residues that differ more significantly in their effect on maintaining (a) the structure of the peptide backbone in the area of the substitution, for example, as a sheet or helical conformation, (b) the charge or hydrophobicity of the molecule at the target sited or (c) the bulk of the side chain. The substitutions that in general are expected to produce substantial changes are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the peptide molecule. However, when it is difficult to predict the exact effect of the substitution, deletion, or insertion in advance of doing so, one skilled in the art will appreciate that the effect will be evaluated by routine screening assays. For example, a TSG-14 variant typically is made by site-specific mutagenesis or homologous recombination of the TSG-14-encoding nucleic acid, expression of the variant nucleic acid in recombinant cell culture, and, optionally, purification from the cell culture, for example, by immunoaffinity adsorption on an antibody containing column.

An "analog" of the TSG-14 protein refers to a non-natural molecule substantially similar to either the entire molecule or a fragment thereof.

A "chemical derivative" of the TSG-14 protein contains additional chemical moieties not normally a part of the protein. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as 2-chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4- nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride, trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(-diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(-succin-imidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016, 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecule Properties, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980).

Standard reference works setting forth the general principles of, and current protocols for, recombinant DNA technology include Watson, J. D. et al., *Molecular Biology of the Gene*, Volumes I and II, The Benjamin/Cummings Publishing Company, Inc., publisher, Menlo Park, Calif. (1987); Darnell, J. E. et al., *Molecular Cell Biology*, Scientific American Books, Inc., publisher, New York, N.Y. (1986); Lewin, B. M., *Genes II*, John Wiley & Sons, publishers, New York, N.Y. (1985); Old, R. W., et al., *Principles of Gene Manipulation: An Introduction to Genetic Engineering*, 2d edition, University of California Press, publisher, Berkeley, Calif. (1981); and Sambrook, J. et at., *Molecular Cloning: A Laboratory Manual*, Cold Spring Harbor Laboratory, Cold Spring Harbor, N.Y. (1989); and Ausubel et al, *Current Protocols in Molecular Biology*, Greene Publications and Wiley Interscience, New York (1987, 1992) and Sambrook et al, *Molecular Cloning: A Laboratory Approach*, Second Edition, Cold Spring Harbor Laboratory Press (1989). These references are hereby entirely incorporated by reference.

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which together comprise the entire expressible genome of an organism. Such a cDNA library may be prepared by methods known to those of skill, and described, for example, in Sambrook et al., supra. Generally, RNA is first isolated from the cells of an organism from whose genome it is desired to clone a particular gene. Preferred for the purposes of the present invention are mammalian, most preferably, human, cell lines.

Oligonucleotides representing a portion of the TSG-14 sequence are useful for screening for the presence of homologous genes and for the cloning of such genes. Techniques for synthesizing such oligonucleotides are disclosed by, for example, Wu, R., et al., *Prog. Nucl. Acid. Res. Molec. Biol.* 21:101–141 (1978).

Because the genetic code is degenerate, more than one codon may be used to encode a particular amino acid (Watson, J. D., In: *Molecular Biology of the Gene*, 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding the TSG-14 sequences is identified.

Although occasionally an amino acid sequence may be encoded by only a single oligonucleotide, frequently the amino acid sequence may be encoded by any of a set of similar oligonucleotides. Importantly, whereas all of the members of this set contain oligonucleotides which are capable of encoding the TSG-14 peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding the TSG-14 fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the TSG-14 gene (Sambrook et al., supra).

A suitable oligonucleotide, or set of oligonucleotides, which is capable of encoding a fragment of the TSG-14 gene (or which is complementary to such an oligonucleotide, or set of oligonucleotides) is identified (using the above-described procedure), synthesized, and hybridized by means well known in the arts against a DNA or, more preferably, a cDNA preparation derived from cells which are capable of expressing the TSG-14 gene, such as TNF-treated FS-4 cells.

Single stranded oligonucleotide molecules complementary to the "most probable" TSG-14 protein coding sequences can be synthesized using procedures which are well known to those of ordinary skill in the art (Belagaje, R., et al., *J. Biol. Chem.* 254:5765–5780 (1979); Maniatis, T., et al., In: *Molecular Mechanisms in the Control of Gene Expression*, Nierlich, D. P., et al., Eds., Acad. Press, New York (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Sambrook et al. (supra), and by Haymes, B. D., et al. (In: *Nucliec Acid Hybridization, A Practical Approach*, IRL Press, Washington, D.C. (1985)), which references are herein entirely incorporated by reference. Techniques such ass or similar to, those described above have successfully enabled the cloning of genes for human aldehyde dehydrogenases (Hsu, L. C., et al., *Proc. Nature. Acad. Sci. USA* 82:3771–3775 (1985)), fibronectin (Suzuki, S., et al., *Eur. Mol. Biol. Organ. J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:8715–8719 (1985)).

In an alternative way of cloning the TSG-14 gene, a library of expression vectors is prepared by cloning DNA or, more preferably, cDNA (from a cell capable of expressing TSG-14, such as a TNF-treated FS-4 cell) into an expression vector. The library is then screened for members capable of expressing a protein which binds to anti-TSG-14 antibody, and which has a nucleotide sequence that is capable of encoding polypeptides that have the same amino acid sequence as TSG-14 proteins or peptides, or fragments thereof. In this embodiment, DNA, or more preferably cDNA, is extracted and purified from a cell which is capable of expressing TSG-14 protein. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

By "vector" is meant a DNA molecule, derived from a plasmid or bacteriophage, into which fragments of DNA may be inserted or cloned. A vector will contain one or more unique restriction sites, and my be capable of autonomous replication in a defined host or vehicle organism such that the cloned sequence is reproducible.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing TSG-14 in order to produce a prokaryotic genomic expression vector library. Procedures for preparing cDNA and for producing a genomic library are disclosed by Sambrook et al. (supra).

By "functional derivative" of a polynucleotide (DNA or RNA) molecule is meant a polynucleotide molecule encoding a "fragment" or "variant" of the TSG-14 protein. It can be a chemical derivative which retains its functions such as the ability to hybridize with a complementary polynucleotide molecule. Such a polynucleotide, or oligonucleotide, chemical derivative is useful as a molecular probe to detect TSG-14 sequences through nucleic acid hybridization assays.

A DNA sequence encoding the TSG-14 protein of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook, J. et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be "operably linked" it is not necessary that two sequences be immediately adjacent to one another.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e. transcribe) only one strand of the two strands of a duplex DNA template. The selection of which strand is transcribed is determined by the orientation of the promoter sequence. This selection determines the direction of transcription since RNA is only polymerized enzymatically by the addition of a nucleotide 5' phosphate to a 3' hydroxyl terminus. The promoter sequences of the present invention may be either prokaryotic, eukaryotic or viral. Suitable promoters are repressible, or, more preferably, constitutive. Strong promoters are preferred.

The present invention encompasses the expression of the TSG-14 protein (or a functional derivative thereof) in either prokaryotic or eukaryotic cells, although eukaryotic expression is preferred.

Preferred prokaryotic hosts include bacteria such as *E. coli*, Bacillus, Streptomyces, Pseudomonas, Salmonella, Serratia, etc. The most preferred prokaryotic host is *E. coli*. Other enterobacteria such as *Salmonella typhimurium* or *Serratia marcescens*, and various Pseudomonas species may also be utilized. Under such conditions, the protein may not be glycosylated. The procaryotic host must be compatible with the replicon and control sequences in the expression plasmid.

The TSG-14 protein can be expressed in a prokaryotic cell (such as, for example, *E. coli, B. subtilis*, Pseudomonas, Streptomyces, etc.), either by itself, or as part of a fusion protein. For expression as a fusion protein, it must be linked in the appropriate reading frame with a prokaryotic protein. Preferred fusion protein "partners" are the trpE protein of *E. coli* or a bacteriophage protein, such as that of the MS2 phage (see Examples, below). To express the TSG-14 protein (or a functional derivative thereof) in a prokaryotic host, it is necessary to operably link the TSG-14 encoding sequence to a functional prokaryotic promoter. Examples of constitutive promoters include the int promoter of bacteriophage lambda, the bla promoter of the $\beta$-lactamase gene of pBR322, and the CAT promoter of the chloramphenicol acetyl transferase gene of pBR325, etc. Examples of inducible prokaryotic promoters include the major right and left promoters of bacteriophage lambda ($P_L$ and $P_R$), the trp, recA, lacZ, lacI, and gal promoters of *E. coli*, the $\alpha$-amylase (Ulmanen, I., et al., *J. Bacteriol.* 162:176–182 (1985)) and the s-28-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli*, Academic Press, Inc., New York. (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (Biochimie 68:505–516 (1986)); and Gottesman, S. (*Ann. Rev. Genet.* 18:415–442 (1984)). For the present invention, a most preferred promoter is the PL promoter of lambda; alternatively, the protein can be expressed under control of a temperature-sensitive repressor of the lambda PL promoter.

Proper expression in a prokaryotic cell also requires the presence of a ribosome binding site upstream of the gene- encoding sequence. Such ribosome binding sites are disclosed, for example, by Gold, L., et al, (*Ann. Rev. Microbiol.* 35:365–404 (1981)).

Preferred hosts are eukaryotic hosts including yeast, insects, fungi, and mammalian cells either in Vivo, or in tissue culture. Mammalian cells provide post-translational modifications to protein molecules including correct folding or glycosylation at correct sites. Mammalian cells which may be useful as hosts include cells of fibroblast origin such as VERO or CHO, or cells of lymphoid origin, such as the hybridoma SP2/O-Ag14 or the murine myeloma P3-X63Ag8, and their derivatives. A most preferred host is one that does not express the TSG-14 gene upon treatment with TNF, such as GM-637, a SV40-transformed human fibroblast cell line.

For a mammalian cell host, many possible vector systems are available for the expression of TSG-14. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activations so that expression of the genes can be modulated. Of interest are regulatory signals which are temperature-sensitive so that by varying the temperature, expression can be repressed or initiated, or are subject to chemical regulation, e.g., metabolite.

A yeast cell host provides substantial advantages in that it can also carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

Any of a series of yeast gene expression systems incorporating promoter and termination elements from the actively expressed genes coding for glycolytic enzymes produced in large quantities when yeast are grown in mediums rich in glucose can be utilized. Known glycolytic genes can also provide very efficient transcriptional control signals. For example, the promoter and terminator signals of the phosphoglycerate kinase gene can be utilized.

Production of TSG-14 or functional derivatives thereof in insects can be achieved, for example, by infecting the insect host with a baculovirus engineered to express TSG-14 by methods known to those of skill. Thus, in one embodiment, sequences encoding TSG-14 may be operably linked to the regulatory regions of the viral polyhedrin protein (Jasny, *Science* 238:1653 (1987)). Infected with the recombinant baculovirus, cultured insect cells, or the live insects themselves, can produce the TSG-14 protein in amounts as great as 20 to 50% of total protein production. When live insects are to be used, caterpillars are presently preferred hosts for large scale TSG-14 production according to the invention.

As discussed above, expression of the TSG-14 protein in eukaryotic hosts requires the use of eukaryotic regulatory regions. Such regions will, in general, include a promoter region sufficient to direct the initiation of RNA synthesis. Preferred eukaryotic promoters include the SV40 early promoter (Benoist, C., et al., *Nature (London)* 290:304–310 (1981)); the RSV promoter associated with an MMTV LTR region; promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the yeast gal4 gene promoter (Johnston, S. A., et al., *Proc. Natl. Acad. Sci. (USA)* 7:6971–6975 (1982); Silver, P. A., et. al., *Proc. Natl. Acad. Sci. (USA)* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the TSG-14 protein (or a functional derivative thereof) does not contain any intervening codons which are capable of encoding a methionine (i.e., AUG). The presence of such codons results either in a formation of a fusion protein (if the AUG codon is in the same reading frame as TSG-14 encoding DNA sequence) or a frame-shift mutation (if the AUG codon is not in the same reading frame as the TSG-14 encoding sequence).

The TSG-14 encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the TSG-14 protein may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototropy to an auxotrophic hosts biocide resistance, e.g., antibiotics, or heavy metals, such as copper or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., *Mol. Cell. Biol.* 3:28 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, $\pi$VX. Such plasmids are, for example, disclosed by Sambrook et al, (supra). Bacillus plasmids include pC194, pC221, pT127, etc. Such plasmids are disclosed by Gryczan, T. (In: *The Molecular Biology of the Bacilli*, Academic Press, New York. (1982), pp. 307-329). Suitable Streptomyces plasmids include pIJ101 (Kendall, K. J., et al,, *J. Bacteriol.* 169:4177-4183 (1987)), and streptomyces bacteriophages such as $\phi$C31 (Chater, K. F., et al,, In: *Sixth International Symposium on Actinomycetales Biology*, Akademiai Kaido, Budapest, Hungary (1986), pp. 45-54). Pseudomonas plasmids are reviewed by John, J. F., et al. (*Rev. Infect. Dis.* 8:693-704 (1986)), and Izaki, K. (*Jpn. J. Bacteriol.* 33:729-742 (1978)).

Preferred eukaryotic plasmids include BPV, vaccinia, SV40, 2-micron circle, etc., or their derivatives. Such plasmids are well known in the art (Botstein, D., et al., *Miami Wntr. Symp.* 19:265-274 (1982); Broach, J. R., In: *The Molecular Biology of the Yeast Saccharomyces: Life Cycle and Inheritance*, Cold Spring Harbor Laboratory, Cold Spring Harbor, N.Y., p. 445-470 (1981); Broach, J. R., *Cell* 28:203-204 (1982); Bollon, D. P., et al., *J. Clin. Hematol Oncol.* 10:39-48 (1980); Maniatis, T., In: *Cell Biology: A Comprehensive Treatise, Vol. 3, Gene Expression*, Academic Press, New York, pp. 563-608 (1980)).

Once the vector or DNA sequence containing the construct(s) has been prepared for expression, the vector or DNA construct(s) may be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment (Johnston et al., *Science* 240:1538 (1988)), etc.

After the introduction of the vector, recipient cells are grown in a selective medium, which selects for the growth of vector-containing cells. Expression of the cloned gene sequence(s) results in the production of the TSG-14 protein, or in the production of a fragment of this protein. This can take place in the transformed cells as such, or following the induction of these cells to differentiate.

The expressed protein or fusion protein may be isolated and purified in accordance with conventional conditions, such as extraction, precipitation, chromatography, affinity chromatography, electrophoresis, or the like. For example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Alternatively, the TSG-14 or functional derivative thereof may be isolated by the use of anti-TSG-14 antibodies. Such antibodies may be obtained by well-known methods, some of which are mentioned below.

Genetic constructs encoding TSG-14 functional derivatives thereof such as those described above, can be used in gene therapy. An abnormal TSG-14 molecule which results in enhanced susceptibility to disease, may be replaced by infusion of cells of the desired lineage (such as fibroblasts, for example) transfected with DNA encoding normal or modified TSG-14 protein, under conditions where the infused cells will preferentially replace the endogenous cell population.

The present invention is also directed to a transgenic non-human eukaryotic animal (preferably a rodent, such as a mouse) the germ cells and somatic cells of which contain genomic DNA according to the present invention which encodes the TSG-14 protein or a functional derivative thereof. The TSG-14 DNA is introduced into the animal to be made transgenic, or an ancestor of the animals at an embryonic stage, preferably the one-cell, or fertilized oocyte, stage, and generally not later than about the 8-cell stage. The term "transgene," as used herein, means a gene which is incorporated into the genome of the animal and is expressed in the animal, resulting in the presence of protein in the transgenic animal.

There are several means by which such a gene can be introduced into the genome of the animal embryo so as to be chromosomally incorporated and expressed. One method is to transfect the embryo with the gene as it occurs naturally, and select transgenic animals in which the gene has integrated into the chromosome at a locus which results in expression. Other methods for ensuring expression involve modifying the gene or its control sequences prior to introduction into the embryo. One such method is to transfect the embryo with a vector (see above) containing an already modified gene. Other methods are to use a gene the transcription of which is under the control of a inducible or constitutively acting promoter, whether synthetic or of eukaryotic or viral origin, or to use a gene activated by one or more base pair substitutions, deletions, or additions (see above).

Introduction of the desired gene sequence at the fertilized oocyte stage ensures that the transgene is present in all of the germ cells and somatic cells of the transgenic animal and has the potential to be expressed in all such cells. The presence of the transgene in the germ cells of the transgenic "founder" animal in turn means that all its progeny will carry the transgene in all of their germ cells and somatic cells. Introduction of the transgene at a later embryonic stage in a founder animal may result in limited presence of the transgene in some somatic cell lineages of the founder; however, all the progeny of this founder animal that inherit the transgene conventionally, from the founder's germ cells, will carry the transgene in all of their germ cells and somatic cells.

Chimeric non-human mammals in which fewer than all of the somatic and germ cells contain the TSG-14 DNA of the present invention, such as animals produced when fewer than all of the cells of the morula are transfected in the process of producing the transgenic mammal, are also intended to be within the scope of the present invention.

The techniques described in Leder, U.S. Pat. No. 4,736,866 (hereby entirely incorporated by reference) for producing transgenic non-human mammals may be used for the production of the transgenic non-human mammal of the present invention. The various techniques described in Palmiter, R. et al., *Ann. Rev. Genet.* 20:465–99 (1986), the entire contents of which are hereby entirely incorporated by reference, may also be used.

The animals carrying the TSG-14 gene can be used to test compounds or other treatment modalities which may prevent, suppress or cure chronic inflammatory conditions mediated by TNF action on connective tissue cells. These tests can be extremely sensitive because of the ability to adjust the dose of an agent under test given to the transgenic animals of this invention. Such diseases include, but are not limited to rheumatoid arthritis, granulomatous diseases, and the like. Transgenic animals according to the present invention can also be used as a source of cells for cell culture.

This invention is also directed to an antibody specific for an epitope of TSG-14 protein. In additional embodiments, the antibodies of the present invention are used in methods to detect the presence of, or measure the quantity or concentration of, TSG-14 protein in a cell, or in a cell or tissue extract, or a biological fluid. The antibodies may also be used in methods for measuring induction of expression of TSG-14 in a cell or in methods for identifying a compound capable of inducing the expression of TSG-14 in a cell. The antibodies may also be used to disrupt the action of TSG-14, thereby preventing or treating diseases associated with overproduction, or inappropriate production or action of TSG-14, such as inflammatory disorders including rheumatoid arthritis, infections and sepsis, as well as conditions associated with TNF-stimulated leukocyte adhesion.

The term "antibody" is meant to include polyclonal antibodies, monoclonal antibodies (mAbs), chimeric antibodies, and anti-idiotypic (anti-Id) antibodies.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

In order to predict antigenic epitopes present in the protein, the amino acid sequence is inspected visually or analyzed by computer, for example, using the program of PEPTIDESTRUCTURE (Jameson et al., *CABIOS* 4:181–186 (1988)), or commercially available. Such programs allow determination of hydropathicity values which are then used to determine which peptide sequences within the overall protein sequence are likely to be most immunogenic based on their potential secondary structure. Such peptides may be synthesized chemically, or alternatively, and preferably, by recombinant DNA methods.

Figure 7:
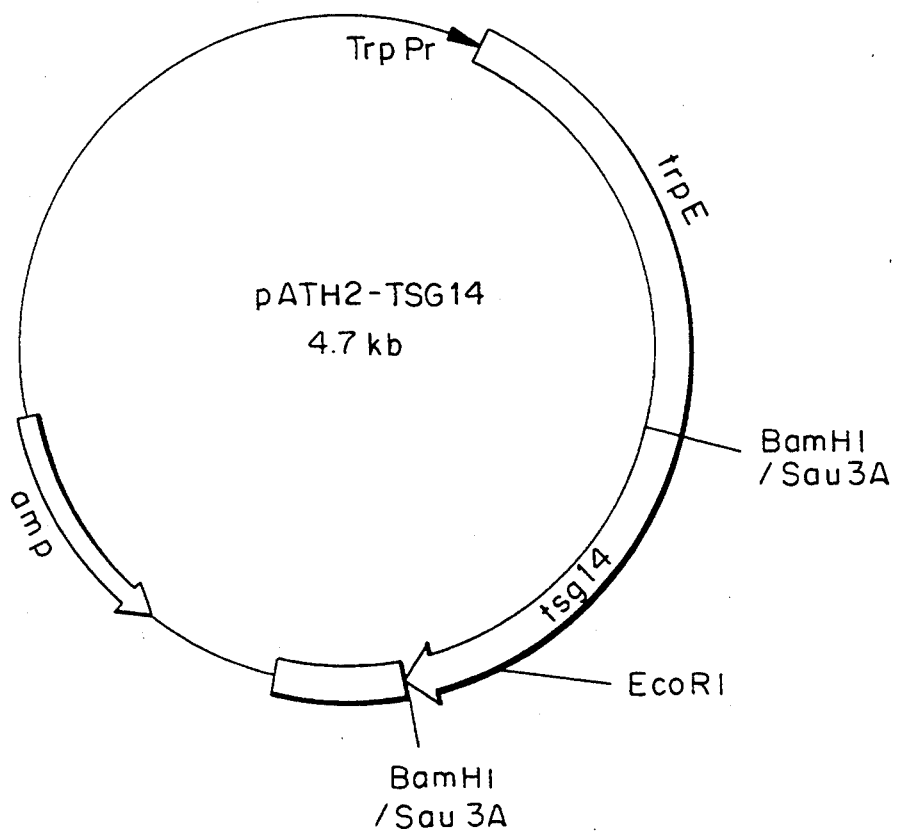
FIG. 7 depicts the pATH2-TSG-14 expression vector. The TSG-14 insert contains a Sau3A site at its 5' end. A Sau3A site at the 3' end of the insert was generated when an EcoRI fragment of TSG-14 was inserted into the pTZ19 vector system, and subsequently cut with the Sau3A enzyme. This insert was then ligated into a unique BamHI site within the coding region of the trpE protein of the pATH2 vector.

One of the pitfalls of generating antibodies to synthetic peptides is the possibility that an antibody so raised may fail to react with the native protein. For this reason, alternative approaches may be used. The TSG-14 protein may be prepared as a bacterially expressed fusion protein by using an expression plasmid, such as the pATH2-TSG-14 expression vector described in FIG. 7 and Example VII, below. Alternatively, the TSG-14 may be expressed as a fusion protein using an expression plasmid such as, for example, pDB169 (Lim, D. et al., supra)). The ArgR repressor protein is highly expressed in *E. coli* strain JM101 under the control of a strong tac promoter of this latter vector. The C-terminal portion of the ArgR coding region can be replaced by an N-terminally deleted TSG-14 coding sequence in the correct reading frame. This construct can then be transfected, for example, into JM101 cells, and the expression of the fusion protein is monitored by SDS-PAGE. Expression of the fusion protein is induced with IPTG, specific for the tac promoter, in a large culture system and purified by affinity chromatography using antibodies specific for the ArgR repressor.

The purified fusion protein is employed for the immunization of rabbits. Alternatively, such a fusion protein, or a functional derivative of the protein such as a synthetic peptide may be used to immunize a rodent for generation of a monoclonal antibody.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art. See, e.g., Sambrook, supra, and Ausubel, supra.

Chimeric antibodies are molecules different portions of which are derived from different animal species, such as those having a variable region derived from a murine mAb and a human immunoglobulin constant region. Chimeric antibodies and methods for their production are known in the art (Cabilly et al., *Proc. Natl. Acad. Sci. USA* 81:3273–3277 (1984); Morrison et al., *Proc. Natl. Acad. Sci. USA* 81:6851–6855 (1984); Boulianne et. al., *Nature* 312:643–646 (1984); Neuberger et al., *Nature* 314:268–270 (1985); Taniguchi et al., European Patent Application 171496 (published Feb. 19, 1985); Kudo et al., European Patent Application 184187 (published Jun. 11, 1986); Robinson et al., International Patent Publication #PCT/US86/02269 (published 7 May 1987); Sun et al., *Proc. Natl. Acad. Sci. USA* 84:214–218 (1987); Better et al., *Science* 240:1041–1043 (1988)). These references are hereby entirely incorporated by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "immunogen" to induce an immune response in yet another animal, producing a so-called anti-anti-Id antibody. The anti-anti-Id may bear structural similarity to the original mAb which induced the anti-Id. Thus, by using antibodies to the idiotypic determinants of a mAb, it is possible to identify other clones expressing antibodies of identical specificity.

Accordingly, mAbs generated against the TSG-14 protein of the present invention may be used to induce anti-Id antibodies in suitable animals, such as Balb/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional Balb/c mice. Sera from these mice will contain anti-anti-Id antibodies that have the binding properties of the original mAb specific for an TSG-14 protein epitope.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of TSG-14 protein according to the methods disclosed herein for intact antibody molecules. Such fragments are typically produced by proteolytic cleavage, using enzymes such as papain (to produce Fab fragments) or pepsin (to produce F(ab')$_2$ fragments).

The antibodies, or fragments of antibodies, of the present invention may be used to quantitatively or qualitatively detect the presence of cells which express the TSG-14 protein on their surface or intracellularly. This can be accomplished by immunofluorescence techniques employing a fluorescently labeled antibody (see below) coupled with light microscopic, flow cytometric, or fluorimetric detection.

The antibodies of the present invention may be employed histologically, as in immunofluorescence or immunoelectron microscopy, for in situ detection of TSG-14 protein. In situ detection may be accomplished by removing a histological (cell or tissue) specimen from a subject and providing the a labeled antibody of the present invention to such a specimen. The antibody (or fragment) is preferably provided by applying or by overlaying on the biological sample. Through the use of such a procedure, it is possible to determine not only the presence of the TSG-14 protein but also its distribution on the examined tissue. Using the present invention, those of ordinary skill will readily perceive that any of a wide variety of histological methods (such as staining procedures) can be modified in order to achieve such in situ detection.

Additionally, the antibody of the present invention can be used to detect the presence of soluble TSG-14 molecules in a biological sample. Used in this manner, the antibody can serve as a means to monitor the presence and quantity of TSG-14 proteins in a subject having a condition associated with TNF induction of TSG-14, such as an inflammatory condition, an infection or sepsis, and the like.

Such immunoassays for TSG-14 protein typically comprise incubating a biological sample, such as a biological fluid, a tissue extract, freshly harvested cells such as lymphocytes or leucocytes, or cells which have been incubated in tissue culture, in the presence of a detectably labeled antibody capable of identifying TSG-14 protein, and detecting the antibody by any of a number of techniques well-known in the art.

The biological sample may be treated with a solid phase support or carrier (which terms are used interchangeably herein) such as nitrocellulose, or other solid support which is capable of immobilizing cells, cell particles or soluble proteins. The support may then be washed with suitable buffers followed by treatment with the detectably labeled TSG-14-specific antibody. The solid phase support may then be washed with the buffer a second time to remove unbound antibody. The amount of bound label on said solid support may then be detected by conventional means.

By "solid phase support or carrier" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of anti-TSG-14 antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the TSG-14-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6- phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect TSG-14 protein through the use of a radioimmunoassay (RIA) (Chard, T., "An Introduction to Radioimmune Assay and Related Techniques" (In: Work, T. S., et al., *Laboratory Techniques in Biochemistry in Molecular Biology*, North Holland Publishing Company, New York (1978), entirely incorporated by reference herein). The radioactive isotope can be detected by such means as the use of a gamma counter or a liquid scintillation counter or by autoradiography. It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to "extract" the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

According to the present invention, it is possible to diagnose circulating antibodies in a subject which are specific for the TSG-14 protein. This is accomplished by means of an immunoassay, as described above, using the protein of the invention or a functional derivative thereof.

In cancer patients, circulating endotoxin levels are high (Harris, R. I. et al., *J. Clin. Path.* 37:467–470 (1984)), particularly in patients with tumor types known to be associated with an increased incidence of cachexia (Humberstone, D. A. et al., *Cancer* 62:1619–1624 (1988)). The presence of high endotoxin levels is probably not a direct result of the tumor per se, but rather reflects the general debility of the patients. Increased translocation from the gut of endogenous bacteria and endotoxins in critical illness is dependent on the presence of malnutrition and that impaired cell-mediated immunity may be an aggravating factor (Wilmore, D. W. et al., *Surgery* 104:917-923 (1988)). As cachectic cancer patients are malnourished and often exhibit suppression of cell-mediated immunity, translocation of endogenous organisms may account for higher levels of endotoxins.

Cancer patients' peripheral blood mononuclear cells often show enhanced "spontaneous" TNF release in vitro (Aderka, D. et al., *Lancet* i:1190–1192 (1985)). TNF production in response to macrophage-activating agents is reduced in patients with advanced metastatic disease but not in cancer patients with only localized disease. These observations supported the notion that TNF production is ongoing in cancer patients, either due to sustained stimulation of monocytes/macrophages by tumor cells or to direct TNF production by tumor cells. TNF was detected in the serum of 50% of 226 cancer patients with active diseased compared to 3% of healthy sera and 18% of sera from disease-free cancer patients (Balkwill, F. et al., *Lancet* ii: 1229–1232 (1987)).

TNF levels are also elevated in a variety of bacterial and viral illnesses, including AIDS (Lahdevirta, J. et al., *Amer. J. Med.* 85:289–291 (1988)) and meningococcal meningitis and septicemia (Waage, A. et al., (*Lancet* i:355–357 (1987)). In a rat burn/infection model, levels of hepatic TNF mRNA increased 100% in rats subjected to burn+infection compared to controls or rats subjected to burns but no infection (Marano, M. A. et al., *Arch. Surg.* 123:1383–1388 (1988)). The animals subjected to burn and infection also showed a greater metabolic response (cachexia). Michie, H. R. et al., *Br. J. Surg.* 76:670–671 (1989), reviewed evidence that TNF is the principal mediator associated with the changes of severe sepsis.

Therefore, the methods of the present invention which are capable of measuring the response of a subject to a cytokine such as TNF or IL-1, or to bacterial endotoxin are useful in predicting the susceptibility of that individual to the debilitating effects of cancer or infectious disease. Similarly, the compositions of the present invention are useful in the prevention or treatment of such diseases, due to their ability to disrupt events set into motion by the action of TNF.

As used herein, the term "prevention" of a condition, such as cancer, viral infections, an inflammatory response, or an infection, in a subject involves administration of the TSG-14 peptide derivative, or antibody (see above) prior to the clinical onset of the disease. "Treatment" involves administration of the protective composition after the clinical onset of the disease. For example, successful administration of a TSG-14 peptide derivative or anti-TSG-14 antibody according to the invention after development of an inflammatory condition, a malignant tumor or a bacterial or viral infection comprises "treatment" of the disease. See, e.g., Chabner et al, eds., *Cancer Chemotherapy: Principles and Practice*, Lippincott, (1990); De Vita et al., eds., *Principles and Practice of Oncology*, 2nd Edition, 1985; Salmon, In: *Current Medical Diagnosis and Treatment* 1991, Schroeder et al., eds., Appleton and Lange, (1991); Sartorelli et al., eds., *Molecular Actions and Targets for Cancer Chemotherapies*, Academic Press, (1981); Katsung, *Basic and Clinical Pharmacology*, Appleton and Lange, Norwalk, Conn., (1992), which references are herein incorporated entirely by reference.

Such viral infections include, but are not limited to the viral diseases listed in Table 12-1 of Berkow et al, eds., *The Merck Manual*, 15th edition, pp. 160–167, Merck and Co., Rahway, N.J., 1987; and Katsung, supra, pages 674–681 and references listed on pages 680–681, which references are entirely incorporated herein by reference.

According to the present inventions the animal subject is a bird or an mammals wherein the mammal is a rodent, a human, a primates ovine, bovines equine, felines or a dog.

The preferred animal subject of the present invention is a mammal. By the term "mammal" is meant an individual belonging to the class Mammalia. The invention is particularly useful in the treatment of human subjects, although it is intended for veterinary uses as well.

A therapeutic agent according to the present invention may comprise a TSG-14 polypeptide, protein, or antibodys and may further comprises at least one cancer chemotherapeutic compound selected from an antimetabolite, a bleomycin peptide antibiotic, a podophyllin alkaloid, a Vinca alkaloid, an alkylating agent, an antibiotic, cisplatin, or a nitrosourea, and or at least one viral chemotherapeutic compound selected from gamma globulin, amantadine, guanidine, hydroxybenzimidazole, interferon-$\alpha$, interferon-$\beta$, interferon-$\gamma$, thiosemicarbarzones, methisazone, rifampin, ribvirin, a pyrimidine analog, a purine analog, foscarnet, phosphonoacetic acid, acyclovir, dideoxynucleosides, ganciclovir. See, e.g., Katsung, *Basic and Clinical Pharmacology*, Appleton and Lange, Norwalk, Conn., (1992), and the references cited therein on pages 798–800 and 680–681, respectively, which references are herein entirely incorporated by reference.

Similarly, a therapeutic agent according to the present invention may comprises a TSG-14 polypeptide, protein, or antibody, and may further comprises at least one anti-inflammatory or anti-viral chemotherapeutic compound selected from a steroidal or non-steroidal anti-inflammatory. See, e.g., Berkow et al, eds., *The Merck Manual*, 15th edition, pp. 160–167, Merck and Co., Rahway, N.J., 1987; and Katsung, supra, pages 674–681 and references listed on pages 680–681, which references are entirely incorporated herein by reference.

The TSG-14 protein, peptides or antibody of the present invention may be administered by any means that achieve their intended purpose, for example, to treat rheumatoid arthritis or other inflammatory conditions, malignant tumors, viral or baterial infections and the like. See, e.g., Chabner et al, eds., *Cancer Chemotherapy: Principles and Practice*, Lippincott, (1990); De Vita et al., eds., *Principles and Practice of Oncology*, 2nd Edition, 1985; Salmon, In: *Current Medical Diagnosis and Treatment* 1991, Schroeder et al., eds,, Appleton and Lange, (1991); Sartorelli et al., eds., *Molecular Actions and Targets for Cancer Chemotherapies*, Academic Press, (1981); Katsung, *Basic and Clinical Pharmacology*, Appleton and Lange, Norwalk, Conn., (1992), which references are herein incorporated entirely by reference.

For example, administration may be by various parenteral routes such as subcutaneous, intravenous, intradermal, intramuscular, intraperitoneal, intranasal, transdermal, or buccal routes. Alternatively, or concurrently, administration may be by the topical route or the oral route. Parenteral administration can be by bolus injection or by gradual perfusion over time.

A typical regimen for preventing, suppressing, or treating a condition such chronic inflammation (as in rheumatoid arthritis) or a malignant tumor, comprises administration of an effective amount of the TSG-14 functional derivative, or an antibody thereto, administered over a period of one or several days, up to and including between one week and about six months.

It is understood that the dosage administered will be dependent upon the age, sex, health, and weight of the recipient, kind of concurrent treatment, if any, frequency of treatment, and the nature of the effect desired. The ranges of effective doses provided below are not intended to be limiting and represent preferred dose ranges. However, the most preferred dosage will be tailored to the individual subject, as is understood and determinable by one of skill in the art. See, e.g., Berkow et al, eds., *The Merck Manual*, 15th edition, Merck and Co., Rahway, N.J., 1987; Goodman et al., eds., *Goodman and Gilman's The Pharmacological Basis of Therapeutics*, 8th edition, Pergamon Press, Inc., Elmsford, N.Y., (1990); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985); Chabner et al., supra; De Vita et al., supra, Salmon, supra; Schroeder et al., supra; Sartorelli et al., supra; and Katsung, supra which references and references cited therein, are entirely incorporated herein by reference.

The total dose required for each treatment may be administered by multiple doses or in a single dose. The TSG-14 polypeptide, protein, functional derivative thereof or antibody may be administered alone or in conjunction with other therapeutics directed to the viral infection, or directed to other symptoms of the viral disease.

Effective amounts of the TSG-14 polypeptide, proteins functional derivative thereof, or antibody thereto, are from about 0.01 µg to about 100 mg/kg body weight, and preferably from about 10 µg to about 50 mg/kg body weight, such 0.05, 0.07, 0.09, 0.1, 0.5, 0.7, 0.9, 1, 2, 5, 10, 20, 25, 30, 40, 45, 50, 55, 60, 65, 70, 75, 80, 85, 90, 95 or 100 mg/kg.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods. See, e.g., Berker, supra; Goodman, supra; Avery, supra; and Ebadi, supra; Chabner et al., supra; De Vita et al., supra; Salmon, supra; Schroeder et al., supra; Sartorelli et al., supra; and Katsungs supra which are entirely incorporated herein by reference, including all references cited therein.

Pharmaceutical compositions comprising at least one TSG-14 protein, peptide or antibody, or fragment thereof, such as 1–10 or 1, 2, 3, 4, 5, 6, 7, 8, 9 or 10, of the invention include all compositions wherein the protein, peptide or antibody is contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically.

Pharmaceutical compositions include suitable solutions for administration by injection or orally, and contain from about 0.01 to 99 percent, preferably from about 20 to 75 percent of active component (i.e., the TSG-14 protein or antibody) together with the excipient. Pharmaceutical compositions for oral administration include tablets and capsules. Compositions which can be administered rectally include suppositories. See, e.g., Berker, supra; Goodman, supra; Avery, supra; Ebadi, supra, Chabner et al., supra; De Vita et al., supra; Salmon, supra, Schroeder et al., supra; Sartorelli et al., supra, and Katsung, supra which are entirely incorporated herein by reference, including all references cited therein.

The preferred animal subject of the present invention is a mammal. By the term "mammal" is meant an individual belonging to the class Mammalia. The invention is particularly useful in the treatment of human subjects, although it is intended for veterinary uses as well.

The present invention provides methods for evaluating the presence and the level of normal or mutant TSG-14 protein or mRNA in a subject. For example, over-expression of TSG-14 in response to stimulation with TNF, IL-1 or an exogenous stimulus such as a bacterial infection, may serve as an important predictor of the inflammatory or septic response. By providing a means to measure the quantity of TSG-14 mRNA in a hybridization assay or TSG-14 protein, as in an immunoassay, the present invention provides a means for detecting susceptibility in a subject to development of an inflammatory condition, such as rheumatoid arthritis, to infectious and septic conditions, and the like.

Oligonucleotide probes encoding various portions of the TSG-14 DNA sequence are used to test cells from a subject for the presence TSG-14 DNA or mRNA. A preferred probe would be one directed to the nucleic acid sequence encoding at least 12 and preferably at least 15 nucleotides of the TSG-14 sequence. Qualitative or quantitative assays can be performed using such probes. For example, Northern analysis (see Examples below) is used to measure expression of an TSG-14 mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al., (U.S. Pat. No. 4,237,224), Sambrooke et al., (supra), etc.

Recently, an in vitro enzymatic method has been described which is capable of increasing the concentration of such desired nucleic acid molecules. This method has been referred to as the "polymerase chain reaction" or "PCR" (Mullis, K. et al., *Cold Spring Harbor Symp. Quant. Biol.* 51:263-273 (1986); Erlich H. et al., EP 50,424; EP 84,796; EP 258,017; EP 237,362; Mullis, K., EP 201,184; Mullis K. et al., U.S. Pat. Nos. 4,683,202; Erlich, H., 4,582,788; and Saiki, R. et al., 4,683,194).

The polymerase chain reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

The precise nature of the two oligonucleotide probes of the PCR method is critical to the success of the method. As is well known, a molecule of DNA or RNA possesses directionality, which is conferred through the 5'-3' linkage of the phosphate groups of the molecule. Sequences of DNA or RNA are linked together through the formation of a phosphodiester bond between the terminal 5' phosphate group of one sequence and the terminal 3' hydroxyl group of a second sequence. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes of the PCR method are selected such that they contain sequences identical to, or complementary to, sequences which flank the particular nucleic acid sequence whose amplification is desired.

More specifically, the oligonucleotide sequences of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

In the PCR, the reaction conditions are cycled between those conducive to hybridization and nucleic acid polymerization, and those which result in the denaturation of duplex molecules. In the first step of the reaction, the nucleic acids of the sample are transiently heated, and then cooled, in order to denature any double-stranded molecules which may be present. The "first" and "second" probes are then added to the sample at a concentration which greatly exceeds that of the desired nucleic acid molecule. When the sample is incubated under conditions conducive to hybridization and polymerization, the "first" probe will hybridize to the nucleic acid molecule of the sample at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. Reviews of the PCR are provided by Mullis, K. B. (*Cold Sring Harbor Symp. Quant. Biol.* 51:263-273 (1986)); Saiki, R. K., et al. (*Bio/Technology* 3:1008-1012 (1985)); and Mullis, K. B., et al, (*Meth. Enzymol.* 155:335-350 (1987)) .

Having now generally described the invention, the same will be more readily understood through reference to the following examples which are provided by way of illustration, and are not intended to be limiting of the present invention, unless specified.

EXAMPLE I

Preparation of cDNA Library from TNF-Treated FS-4 Cells and Isolation of TNF-Inducible cDNA Materials

*E. coli*-derived recombinant human TNF (specific activity, $3 \times 10^7$ U/mg) was supplied by M. Tsujimoto of the Suntory Institute for Biomedical Research, Osaka, Japan. *E. coli*-derived recombinant human IL-1α (specific activity, $1 \times 10^9$ U/mg) was received from Alvin Stern and Peter Lomedico, Hoffmann-LaRoche, Inc., Nutley, N.J. *E. coli*-derived human gamma interferon (IFN-gamma) (specific activity, $2.1 \times 10^7$ U/mg) was provided by Biogen, Cambridge, Mass. *E. coli*-derived human IFN-β (Betaseron, specific activity, $2 \times 10^8$ U/mg) was obtained from Triton Biosciences, Alameda, Calif. Epidermal growth factor (EGF), platelet-derived growth factor (PDGF) and transforming growth factor-β (TGF-β) were purchased from Collaborative Research, INc., Bedford, Mass. Poly(I)-poly(C) was from P-L Biochemicals, Inc., Milwaukee, Wis. $N^6$-2'-O-dibutyl adenosine cyclic 3', 5'-monophosphate, cycloheximide, forskolin, 12-O-tetradecanoylphorbol 13-acetate (TPA), the calcium ionophore A23187, and isobutylmethylxanthine were purchased from Sigma Chemical Co., St. Louis, Mo. The pHe7 plasmid, used as a source of internal reference cDNA (Kaczmarek, L. et al., *J. Cell Biol.* 104:183-187 (1987), was supplied by P. B. Sehgal, Rockefeller University, New York, N.Y.

Cell Culture

The human diploid FS-4 foreskin fibroblast cell line (Vilcek, J. et al., *Proc. Natl. Acad. Sci. USA*

70:3909–3913 (1973)) was used at passage level 15 in all experiments. FS-4 cells were grown in Eagle minimal essential medium (E-MEM) supplemented with 6 mM HEPES, 3 mM Tricine, 50 μg/ml gentamicin, and 5% heat inactivated (56° C., 30 min) fetal bovine serum (FBS; GIBCO Laboratories, Grand Island, N.Y.). For experiments, $4 \times 10^6$ cells were seeded in 175 cm$^2$ Falcon flasks, incubated at 37° C., and allowed to grow to confluence over 6 days. The confluent monolayers were washed once with phosphate buffered saline and replenished with E-MEM containing 0.25% FBS. The cultures were incubated in this medium for another 72 h at 37° C. to let the cells become quiescent and then treated with the appropriate agents, as specified herein.

Preparation of cDNA and Construction of cDNA Library

Total cytoplasmic RNA was isolated from quiescent FS-4 cells treated for 3 h with TNF (10 ng/ml) as described previously (Lin, J.-X. et al., *J. Biol, Chem.* 262:11908–11911 (1987)). Poly(A)+ RNA was selected by one cycle of binding to oligo(dT)-cellulose (type 7; P-L Biochemicals). Double stranded cDNA was made from 10 μg of poly(A)+ by using the cDNA synthesis system of Bethesda Research Laboratories, Gaithersburg, Md. The double stranded cDNA was methylated with EcoRI methylase and made blunt-ended with T4 DNA polymerase. EcoRI linkers were ligated onto the cDNA, which was then restricted with EcoRI. The resulting cDNA greater than 600 base pairs in size was fractionated and separated from the linker fragments by Sepharose CL4B column chromatography and ligated into the EcoRI site of lambda gt10. The library was packed in vitro with Gigapack packaging extract (Stratagene).

Differential Screening of the cDNA Library

The lambda gt10 cDNA library was plated on *E. coli* LE392 at a density of 1000 PFU/dish (150 mm diameter). Nitrocellulose filters were used to prepare duplicate plaque lifts of each plats. Prehybridization and hybridization of filters with $^{32}$P-labeled single-stranded cDNA probe were performed as described (Leonard, D. G. B. et al., *Molec. Cell. Biol.* 7:3156–3167 (1987)). Probes were synthesized by using the Bethesda Research Laboratories cDNA synthesis system with 10 μg poly(A)+ RNA. The first strand synthesis reaction was adjusted to contain 0.5 mM each of dATP, dGTP, and dTTP, 0.1 mM dCTP, 100 μg/ml dactinomycin, and 200 μCi of [α-$^{32}$P]dCTP (3000 Ci/mmol; ICN Pharmaceuticals, Inc., Irvine, Calif.). After synthesis of the cDNA, the RNA was removed by incubation in 0.2M NaOH at 70° C. for 20 min. The reaction was neutralized with HCl and the cDNA was ethanol precipitated in the presence of 2M ammonium acetate. The pellet was suspended in 200 μl of TE (10 mM Tris HCl, pH 8.0, 1 mM EDTA) and added to the hybridization solution and filters. One of two probes was used to hybridize to each of the two replica filters; one was made from untreated FS-4 cells, and the other was made from FS-4 cells treated for 3h with TNF (10 ng/ml). After hybridization, the filters were washed in 2×SSC (1×SSC is 0.15M NaCl plus 0.015M sodium citrate) −0.1% sodium dodecyl sulfate (SDS) at 65° C. for 1 h with one or two changes. Filters ere exposed to Kodak XAR-5 film for 1–2 days with an intensifying screen at −70° C. Plaques that showed different intensities of the hybridization signal with the two probes were selected. These clones were subjected to one further round of differential screening, and the plaques were purified.

Subcloning Of the cDNA, Inserts, and Cross Hybridization Studies

*E. coli* LE392 cells in soft 0.7% agarose were poured into 150 mm plates. The lambda clones were then spotted on the plates in a grid array. Four nitrocellulose filters were lifter from each plate, processed, and stored until use. To prepare cDNA inserts from plaque-purified recombinant clones, 10 ml of liquid lysate was clarified and digested with 2 μg of DNase I per ml to remove contaminated chromosomal DNA. Then 2 ml of 2.5% SDS-0.5M Tris HCl (pH9.5)-0.25M EDTA was added, and plates were incubated at 65° C. for 15 min to lyse the phages. The solution was then cooled to room temperature before 2.0 m' of 10M ammonium acetate was added. The sample was chilled on ice for 20 min and centrifuged at 15,000× g at 4° C. for 10 min to obtain the DNA pellet. The pellet was suspended in 100 μl TE buffer containing 2 Mg RNase A (Boehringer) per ml, and cut with the restriction enzyme EcoRI. The cDNA insert was isolated and subcloned into the EcoRI site of an M13mp19 vector. The cDNA inserts to be used as probes for cross-hybridization and Northern (RNA) blot experiments were prepared from the recombinant M13 clones by restriction with EcoRI to minimize background. The probes were prepared earlier. The hybridization conditions ere essentially as described above for the differential screening experiments.

Northern Blot Analysis

Cytoplasmic RNA was fractionated on a 1% agarose gel containing formaldehyde and blotted onto Zetaprobe blotting membranes (Bio-Rad Laboratories, Richmond, Calif.). Cytoplasmic RNA was loaded at 10 μg/lane. Prehybridization and hybridization of Northern blots were performed as described (Lin. J.-X. et al., supra). Filters were probed with 32P-labeled cDNA insert from recombinant M13 clones and/or with 32P-labeled internal reference pHe7 insert. Northern blots were quantified with a laser densitometer.

Sequence Analysis

Single stranded DNA templates from recombinant M13 clones were prepared, and several hundred nucleotides from each end of the cDNA were determined by the dideoxynucleotide-chain termination method (Sanger, F. et al., *Proc. Natl. Acad. Sci. U.S.A.* 74:5463–5468 (1977)). The partial nucleotide sequences were compared with sequences entered in GenBank (release 60.0).

RESULTS

FS-4 cells were grown to confluence, then switched to medium with 0.25% fetal bovine serum (FBS) and incubated for 72 h at 37° C. The cells were then exposed to recombinant human TNF (10 ng/ml). Cytoplasmic RNA was isolated (Lin. J.-X. et al., *J, Biol. Chem.* 262:11908 (1987)) after a 3-h incubation with TNF. A 3 h incubation with TNF was chosen for the following reason. It is known that TNF induces an increase in the level of some mRNAs within 20–30 min in quiescent FS-4 cells, but some of these "early response" mRNAs are elevated only transiently, for 30–120 min (e.g., c-fos and c-myc mRNA; see Lin, J.-X. et. al., supra). Although such immediate early response gene products may be important for turning on other genes, the fact that they are induced only transiently suggested that they are not the actual effector molecules responsible for the phenotypic changes induced by TNF. Therefore, a search was initiated for cDNAs corresponding to messages that are more stably elevated after TNF treatment.

Poly(A)+ RNA was isolated from the cytoplasmic RNA by and double-stranded cDNA was synthesized. The resulting cDNA library from TNF-treated FS-4 cells, consisting of $2 \times 10^6$ recombinant clones, was screened for TNF-inducible gene sequences by differential hybridization with [$^{32}$p] cDNA probes prepared from poly(A)+ RNA from control and from TNF-treated FS-4 cells. Plaques which gave a strong signal when probed with cDNA from TNF-treated cells, but not when probed with control cell cDNA, were picked as presumptive TNF-inducible genes.

Approximately $3 \times 10^4$ plaques were screened, and 47 were scored as clearly inducible after two rounds of screening. They were designated TSG 1–47 (TSG="TNF-stimulated gene sequence"). To determine the number of different mRNAs represented among the TSG clones selected by differential screenings the inserts were tested for sequence homology by cross-hybridization. A total of 44 cloned cDNAs have been examined by cross-hybridization to each other. These experiments revealed a total of eight distinct, non-crossreacting cDNAs. As summarized in Table 2, below, some of the cDNAs were represented among the 44 clones with a high frequency (TSG-8 and TSG-14) while others were much less abundant (TSG-21, TSG-27 and TSG-37). The size of the corresponding mRNAs ranged from 0.8 to 4.5 kb.

TABLE 2

Abundance of Individual TSG cDNAs Among 44 TNF-specific cDNA Clones

| cDNA | Abundance[a] | Approximate size of corresponding mRNA (kb) |
|---|---|---|
| TSG-1 | 6 | 1.6 |
| TSG-6 | 6 | 1.5 |
| TSG-8 | 11 | 1.1 |
| TSG-12 | 3 | 4.5 |
| TSG-14 | 13 | 2.3 |
| TSG-21 | 1 | 2.4 |
| TSG-27 | 2 | 2.4 |
| TSG-37 | 2 | 0.8 |

[a]Each of the 44 cDNA inserts was isolated from the #gt10 vector and subcloned into the M13mp19 vector. Inserts from the M13 vector were [32p]-labeled by nick translation and hybridized with each of the 44 lambda cDNA clones. Cross-hybridization was taken as evidence that the cDNAs were derived from the same mRNA species.

EXAMPLE II

Kinetics of Induction of TNF-Induced mRNAs

To ascertain that the eight distinct TSG cDNAs isolated indeed correspond to mRNAs whose levels are up-regulated in FS-4 cells by TNF treatment, quiescent FS-4 cultures were treated with TNF (20 ng/ml) for different intervals ranging from 0.5 to 16 h, cytoplasmic RNA was isolated (Lin, J.-X. et al., supra) and mRNA levels corresponding to each of the eight cDNAs were quantitated by Northern blot analysis and densitometric scanning of the autoradiograms (FIGS. 1A–1H and 2A–2H). The increase in mRNA levels ranged from about 3-fold (TSG-21) to over 100-fold (TSG-6 and TSG-8).

Three different patterns of mRNA stimulation were noted. The first pattern was characterized by an increase to peak levels by 2–4 h, followed by a gradual decrease in mRNA levels (TSG-1 and TSG-6). The second pattern showed a rapid increase of mRNA levels to a maximum by 1.5 to 4 h, followed by a plateau until at least 16 h (TSG-8, TSG-12, TSG-6–14 and TSG-37). The third pattern was characterized by a possible initial decrease, followed by a slow gradual increase in mRNA levels throughout the 16-h observation period (TSG-21 and TSG-27).

EXAMPLE III

Partial Sequencing of TSG cDNAs

To determine whether the isolate, cDNAs were homologous to previously identified genes, all eight cDNAs were partially sequenced (300–400 bp) and the sequences determined were checked against sequences available in GenBank. Sequences of four cDNAs (TSG-1, TSG-8, TSG-21 and TSG-27) were found to be identical to earlier identified genes. Of these, TSG-1 corresponded to the gene for β-thromboglobulin-like protein 3°–10° C. (Schmid, J. et al., *J. Immunol.* 139:250 (1987)), also known as IL-8. TSG-8 was identical to the recently cloned gene for "monocyte chemotactic and activating factor" (MCAF) (Matsushima, K. et al., *Cytokine* 1:2 (1989)). TSG-21 and TSG-27 were found to be identical to the collagenase and stromelysin genes, respectively, and TSG-37 was found to encode metallothionein II. The other three partial cDNA sequences showed no significant homologies with known genes, indicating that they represented hitherto unidentified gene sequences.

Induction of IL-8 (=TSG-1) by TNF and by IL-1 was recently observed by others (Matsushima, K. et al., 1989, supra; *J. Exp. Med*, 167:1883 (1988)). In-8, a neutrophil chemotactic factor, is structurally related to several members of a family of inflammatory cytokines that include platelet factor-4 (PF-4), the IFN-gamma-inducible protein IP-10, the PDGF-inducible gene JE, proteins termed MIP-1 and MIP-2, and GRO (Matsushima, K. et al., supra; Larsen, C. G. et al., *Science* 243:1464 (1989)). Most of these proteins appear to be chemotactic.

MCAF (=TSG-8) induction in human fibroblasts by TNF and IL-1 has been recently described (Matsushima, K. et al., supra). Interestingly, MCAF shows significant amino acid sequence similarity (21%) with In-8, and they both have four cysteines at similar positions.

Collagenase (TSG-21) was also reported earlier to be TNF-inducible in synovial cells and fibroblasts (Dayer et al., supra). It is very likely that the ability of TNF to induce collagenase is related to TNF's role in tissue remodeling during inflammation. While the induction of stromelysin by TNF has not been reported, stromelysin mRNA was recently shown to be inducible by In-1 (Quinones, S. et al., *J. Biol. Chem.* 264:8339 (1989)). Like collagenase, stromelysin is a collagen-degrading metalloproteinase, and both can also degrade fibronectin, laminin and cartilage proteoglycans. Both collagenase and stromelysin are thought to be important in the increased extracellular matrix degradation occurring in rheumatoid arthritis.

Finally, metallothionein II (MT-II) has been shown to be inducible by various stresses, including heavy metal challenge, injection of lipopolysaccharide as well as by cytokines including interferons and IL-1) (Karin, M., *Cell* 41:9–10 (1985)). In addition to its ability to bind heavy metal ions, MT-II may also act as a scavenger of free radicals released by activated macrophages and neutrophils during an inflammatory response, MT-II induction would thus serve a protective role in the prevention of tissue injury (Thornalley, P. J., *Biochim. Biophys. Acta* 827:36–44 (1985)).

It is significant that all five TSG cDNAs identified by sequencing correspond to genes coding for proteins important in the inflammatory process. These results support the utility of the present approach of cloning TNF-inducible cDNAs from human fibroblasts in the identification of novel genes with important functions in immune responses and inflammation.

EXAMPLE IV

Patterns of TSG-14 mRNA Induction by Different Cytokines and Other Agents

Table 3 provides summarizes data of experiments which measured levels of TSG-14 mRNA in FS-4 cells exposed to various agents using Northern blot analysis. TSG-14 was inducible by the protein synthesis inhibitor, cycloheximide, as was the case for other TNF-induced mRNAs, TSG-8 and TSG-12. The addition of cycloheximide did not TSG-14 mRNA inducibility by TNF, suggesting that the increase in the mRNA levels was the result of a direct action of TNF, not requiring a protein intermediate. TSG-14 mRNA was not inducible by IFN-$\beta$ of IFN-gamma. TSG-14 mRNA was inducible by IL-1, by the double-stranded RNA poly-(I):poly(C), and by the phorbol ester 12 O-tetradecanoyl phorbol 13-acetate (TPA).

TABLE 3

INDUCTION OF TSG-14 mRNA

| Stimulus | Conc. | Relative Increase in TSG-14 mRNA |
|---|---|---|
| Tumor necrosis factor (TNF) | 20 ng/ml | +++ |
| Cycloheximide | 10 µg/ml | + |
| TNF + cycloheximide | | +++ |
| Interleukin-1 | 1 ng/ml | +++ |
| Interferon-$\beta$ | 500 U/ml | 0 |
| Interferon-gamma | 100 U/ml | 0 |
| TNF + IFN-$\beta$ | | +++ |
| TNF + IFN-gamma | | +++ |
| Epidermal growth factor | 25 ng/ml | + |
| Platelet derived growth factor | 5 ng/ml | + |
| Transforming growth factor-$\beta$ | 2 ng/ml | 0 |
| Poly (I):Poly (C) | 50 µg/ml | ++ |
| Phorbol ester (TPA) | 100 ng/ml | + |
| A23187 | 1 µM | 0 |
| Forskolin | 10 µM | 0 |
| dibutyryl cyclic AMP | 100 µM | 0 |
| Isobutyl methylxanthine | 100 µM | 0 |

The results shown are a summary of northern blot experiments in which total cellular RNAs were extracted from FS-4 cells treated for 2 hrs with the indicated concentration of agent or agents. Results reflect the relative increase in TSG-14 mRNA levels over control.

Epidermal growth factor (EGF) and platelet derived growth factor (PDGF) each stimulated a moderate induction of TSG-14 mRNA. Transforming growth factor-$\beta$ (TGF-$\beta$), the calcium ionophore, A23187, dibutyryl cyclic AMP and the phosphodiesterase inhibitor, isobutyl methylxanthine, were ineffective in inducing TSG-14 mRNA.

EXAMPLE V

Partial DNA Sequence of TSG-14

Figure 3A:
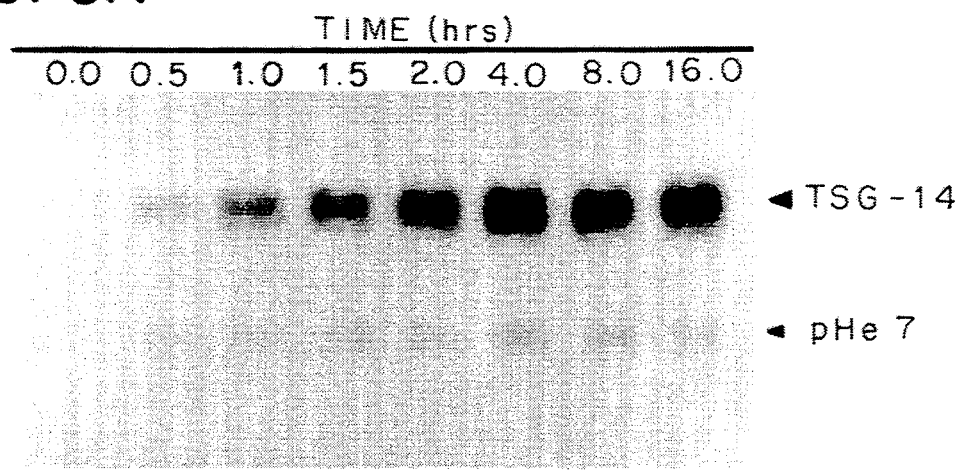
FIG. 3A is a northern blot and FIG. 3B is a graph (taken from the appropriate portion of FIGS. 1A–1H and 2A–2H) showing the induction of TSG-14 mRNA by TNF. Quiescent FS-4 cells were exposed to 20 ng/ml TNF at 0 hrs. Total cellular mRNA was removed at various time points and was fractionated on a formaldehyde/agarose gel, transferred to a Zeta-probe blotting membrane and hybridized with a $^{32}$p-labeled TSG-14 cDNA probe. The autoradiogram was then scanned by laser densitometry an plotted, normalizing the highest intensity band as 100% induction.
Figure 3B:
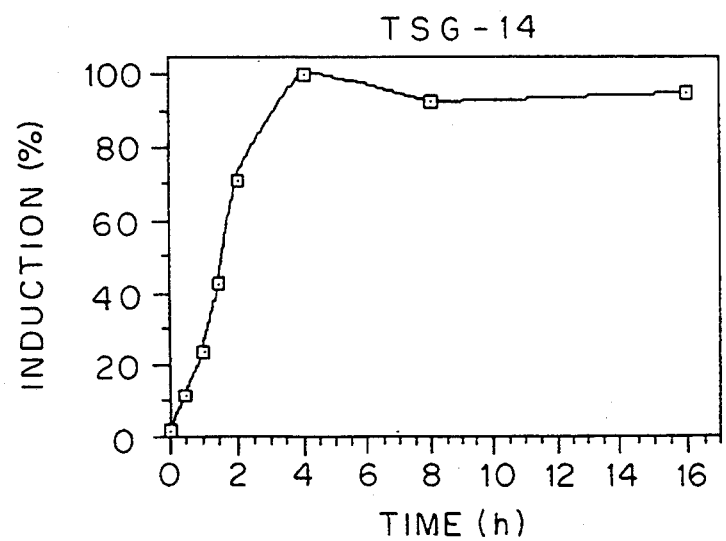

TSG-14 was cloned into M13mp18 and sequenced. The cDNA sequence of TSG-14 was found to consist of 1837 base pairs (SEQ ID NO:1; see FIG. 4). Complete sequence of the cDNA was derived by sequencing several shorter overlapping fragments. Analysis of the sequence revealed three open reading frames, but only one of these appears to be the correct reading frame, based on several considerations. First, this ORF contains a short 5' 73-bp untranslated region, which is consistent with the character of most mRNAs. Second, the initiation codon for this ORF is in the context of a consensus start region. Finally, the 5' coding region encodes a 17 amino acid-long highly hydrophobic region (FIGS. 3A–3B and 4), with characteristics of a cleavable signal peptide sequence.

The ORF of TSG-14 consists of 534 nucleotides, encoding a protein 178 amino acids long (SEQ ID NO:2; see FIG. 4). The transcript contains a very long 3' untranslated region, a feature not unusual among cytokines. Furthermore, 2 polyadenylation sites are present at the extreme 3' end of the sequence. Most interestingly, the 3' noncoding region of the TSG-14 sequence contains a region of greater than 70% homology with the 3' region of another cytokine, namely IL-1$\beta$, based on information derived from the Genbank database. Taken together, these features indicate that TSG-14 is a novel, biologically active cytokine.

EXAMPLE VI

TSG-14 Amino Acid Science and Protein Structure

The predicted sequence of the TSG-14 protein has several remarkable features. No potential N-glycosylation sites are present. Interestingly, while the mature protein only one lysine residue is found in the entire protein° Five cysteine residues are present in the mature proteins indicating inter- or intra-molecular disulfide bridges.

Figure 5:
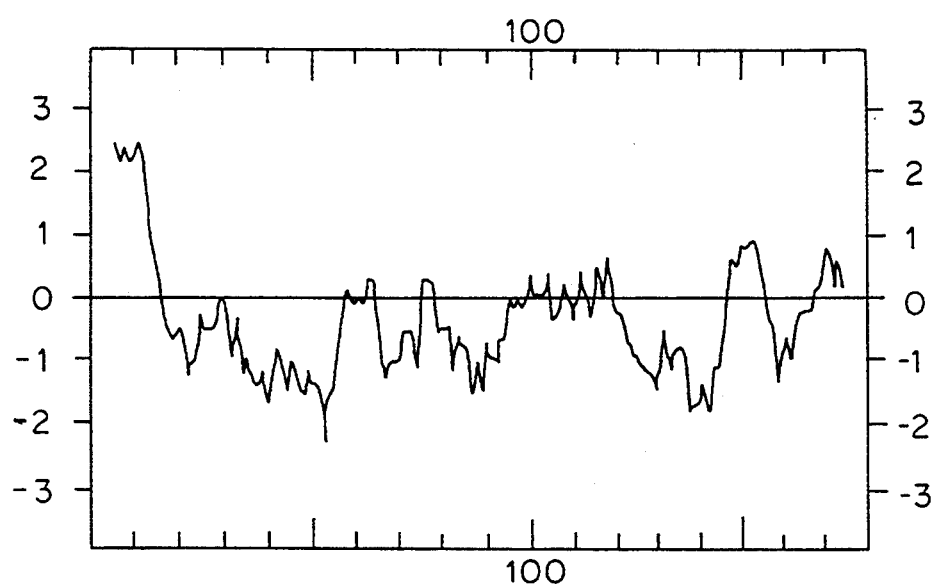
FIG. 5 is a hydrophobicity plot of the TSG-14 protein. The hydrophobicity was plotted using the DNA Strider program on a Macintosh SE computer, utilizing the algorithm of Kyte and Doolittle (*J. Mol. Biol,* 157:105 (1982)).

A hydrophobicity plots using the algorithm of Kyte and Doolitle (supra), predicts the presence of a highly hydrophobic sequence at the N-terminus (FIG. 5). Indeed, the first 17 amino acids are quite hydrophobic in character, suggesting that this stretch represents a cleavable signal sequence or membrane anchor.

Figure 6:
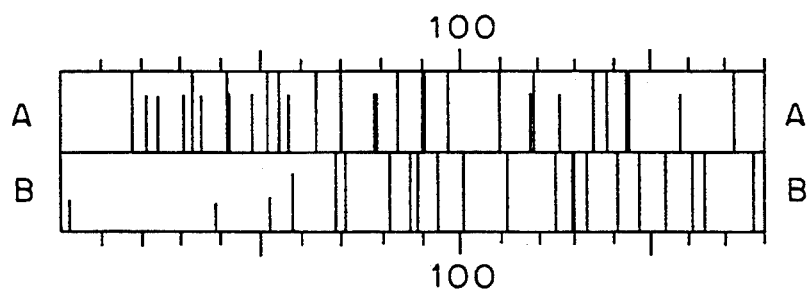
FIG. 6 is an acid/base plot of the TSG-14 protein. The isoelectric points of the amino acid residues comprising TSG-14 were calculated and plotted using the DNA Strider program on a Macintosh SE computer.

Plotting TSG-14 as a function of the isoelectric points of the individual amino acid (see FIG. 6) residues revealed that the N-terminal half of the protein is strongly acidic. Indeed, within a 50-amino acid region there are 15 acidic amino acids, whereas only 4 basic residues are found in the same stretch. The rest of the protein has a slight excess of basic over acidic amino acids. The net charge of this protein is acidic (calculated pI=4.51); the protein is therefore highly soluble.

Analysis of the TSG-14 protein secondary structure revealed that several regions are expected to be highly antigenic (based on the relative antigenicity of individual amino acids in the context of neighboring residues). This property is of benefit in the preparation of antibodies to TSG-14 (see below). A homology search based on the predicted amino acid sequence was conducted against other sequences in the NBRF protein database (release 18.0). No significant homology was found with any other protein, indicating that TSG-14 indeed represents a novel protein.

EXAMPLE VII

Preparation of Bacterial Fusion-Protein and Expression of Protein

To express a bacterial fusion protein of TSG-14, a TSG-14 insert containing a Sau3A site at its 5' end was used. A Sau3A site at the 3' end of the insert was generated when an EcoRI fragment of TSG-14 was inserted into the pTZ19 vector system, and subsequently cut with the Sau3A enzyme. This insert was then ligated into a unique BamHI site within the coding region of the trpE protein of the pATH2 vector, generating the pATH2-TSG-14 expression vector. (See FIG. 7 for depiction of vector.) Expression of the fusion protein was under the control of the Trp promoter.

Figure 8:
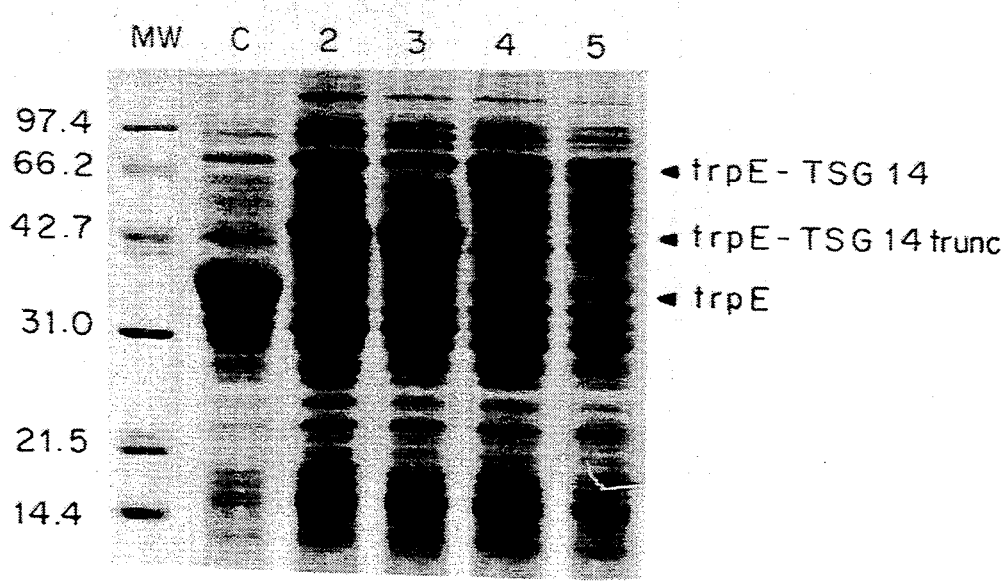
FIG. 8 is a gel pattern showing expression of the TrpE/TSG-14 fusion protein. E. coli JM101 cells were transformed with the pATH2-TSG-14 expression vector and induced with indole acrylic acid. Whole cell lysates were denatured by boiling in a buffer containing 2% SDS and S-mercaptoethanol. The denatured samples were electroeluted on a 10% acrylamide gel containing SDS and stained with Coomassie Blue. Lane 1: MW markers; lane 2: control (TrpE only); lanes 3 and 4; truncated trpE-TSG-14 fusion protein-the pATH2-TSG-14 vector was cut with PstI to generate a smaller expressed protein (MW=44 kDa); lanes 5 and 6; TrpE/TSG-14 fusion protein (MW is about 60 kDa).

Expression plasmid pATH2-TSG-14 was transferred into competent E. coli JM101 cells. Transformed cells in M9 medium containing 2% Casamino acids, 20 μg/ml of n-tryptophan, and 150 μg/ml of ampicillin were grown to a density of $A_{600}=0.5$ (absorbance at 600 nm). To induce synthesis of the fusion protein, cells were pelleted and resuspended in prewarmed L-tryptophan-free medium. After an additional 1-hour incubation, 20 μg/ml of 3-β-indoleacrylic acid was added and the incubation was continued for an additional 24 hours. FIG. 8 shows that protein of the expected size (approximately 60 kDa) was in fact induced following addition of 3-β-indoleacrylic acid. A truncated trpE-TSG-14 fusion protein resulting from cutting the pATH2-TSG-14 vector with PstI, having a molecular weight of about 44 kDa, is also shown.

EXAMPLE VIII

Purification of TSG-14 Fusion Protein

Purification of the fusion protein described above is performed essentially as described by Strebel et al. (J. Virol. 57:983-991 (1985)). Cells from a 1 L culture are pelleted and washed with TEN (10 mM Tris-HCL, pH 8.0, 1 mM EDTA, 0.5M NaCl), lysed with lysozyme (5 mg/ml) and finally broken by sonication. Insoluble material is recovered by centrifugation (30 min, 20,000×g) and extracted sequentially with 20 ml of 3M urea and 5 ml of 7M urea each for 30 min at 37° C. The 7M urea extract containing the fusion protein is further purified by preparative SDS-PAGE. After electrophoresis the fusion protein is excised from the gel, electroeluted and concentrated as needed. The purity of the electroeluted fusion protein is checked on analytical gels. After the second round of electroelution, highly purified fusion protein is obtained with no detectable E. coli protein bands on SDS-PAGE.

EXAMPLE IX

Expression of TSG-14 in various Cells

The biological functions of TSG-14 can be studied by expression of TSG-14 cDNA in a cell line which does not respond to TNF by the induction of TSG-14 mRNA. The inducibility of TSG-14 mRNA by TNF was thus examined in various cell lines by Northern blot analysis. Included in this study were a number of SV40-transformed cell lines and tumor cell lines. The results are shown in Table 4.

TABLE 4

| Induction of TSG-14 mRNA by TNF | | |
|---|---|---|
| Cell Line | Control | TNF (20 ng/ml, 4 hr) |
| Normal Cells | | |
| FS-4 | − | + |
| HUVEC | − | + |
| SV40-Transformed Cell Lines | | |
| FS-4 SV2 | +/− | ++ |
| FS-4 SV3 | +/− | ++ |
| FS-4 SV4 | +/− | ++ |
| WI-38 VA | +/− | +/− |
| GM637 | − | + |
| Tumors | | |
| A549 | − | − |
| A673 | − | − |
| Colo205 | − | − |
| HT29 | − | − |

TABLE 4-continued

| Induction of TSG-14 mRNA by TNF | | |
|---|---|---|
| Cell Line | Control | TNF (20 ng/ml, 4 hr) |
| SK-Mel-19 | − | − |
| U937 | − | − |

The data represent a summary of northern blots of TSG-14 mRNA in normal, SV40-transformed, and tumor cell lines. HUVEC: human umbilical vein endothelial cells; SV2, SV3 and SV4: FS-4 cells tranformed with SV40 large T antigen; WI-38: SV40-transformed lung fibroblasts; GM637: SV40-transformed skin fibroblasts; A549: lung carcinoma line; A637: rhabdomyosarcoma line; Colo205: colon adenocarcinoma line; HT29: colon adenocarcinoma line; SK-Mel-19: melanoma line; U937: promonocytic leukemia line.

Thus, TSG-14 mRNA is expressed in response to TNF in some cells only. No expression was observed in the six tumor lines analyzed, even in the presence of TNF. Interestingly, the levels of TSG-14 mRNA were higher in FS-4 cells transfected with the large T-antigen of SV40, which transforms these cells, compared to normal, nontransformed counterparts. This is in contrast to another TNF-induced protein, TSG-6, where TNF induction of TSG-6 mRNA was significantly decreased in FS-4 cells transfected with SV40 large T antigen. Thus, the degree of "oncogenic" transformation has a differential effect on the inducibility of TSG-14 versus TSG-6 mRNA.

EXAMPLE X

Transfection and Expression of TSG-14 cDNA in Cell Lines

Mammalian expression vectors of TSG-14 are constructed using pSV2 (Mulligan, R. C. et al., Science 209:1423 (1980)) as a constitutive expressor and pMAMneo (Sardet, C. et al., Cell 2.6:271 (1989)) as a dexamethasone-inducible expressor, respectively. These constructs are used to transfect cells in which TSG-14 is not inducible by TNF, namely, the A549 cell line, using CaPO$_4$ precipitation. In the case of stable transfection with a pSV2-TSG-14 vector, pRSVneo (Gorman, C. et al., Science. 221:551 (1983)), which confers resistance to the antibiotic G418, is cotransfected.

Stable transfectants are selected in a G418 containing medium, and tested for the expression of TSG-14 cDNA by northern blot analysis. Transfectants express TSG-14 mRNA in the absence of TNF. The major band in a northern blot is of the same size as the band corresponding to TSG-14 mRNA induced by TNF in FS-4 cells.

Preparation of Polyclonal Antiserum and Purification of Anti-TSG-6 Antibodies by Immunoaffinity Chromatography Rabbits are first immunized with about 200 μg of the TrpE/TSG-14 fusion protein suspended in Freund's complete adjuvant and are boosted at intervals of 2-3 weeks with the same amount of protein in Freund's incomplete adjuvant. All injections are performed subcutaneously, except for the final boost which is intravenous. Rabbits are bled about six days after immunizations. Sera are analyzed by immunoblotting according to Strebel et al. (J. Virol, 57:983-991 (1985)).

To obtain antibodies specific for TSG-14 domains of the fusion protein, the antiserum is subjected to purification on an immunoaffinity matrix to which a second TSG-14 fusion protein, for example, a MS2/TSG-14 fusion protein is coupled. Such a fusion protein is produced using the plasmid pEX34A, a derivative of pEX29 (Klinkert, M. et al., *Infec. Immun.* 49:329–335 (1985)), which permits the production of foreign proteins fused to the N-terminal part of the MS2 polymerase and controlled by the temperature-inducible lambda PL promoter.

The immunoaffinity chromatography matrix is prepared as follows. Five mg of purified MS2/TSG-14 fusion protein is dialyzed extensively against 0.5M NaCl. Three ml of EAH-Sepharose 4B (Pharmacia) is washed extensively with 0.5M NaCl and the purified MS2/TSG-6 fusion protein is added. The pH is adjusted to 4.5 and 40 mg 1-(3-dimethylaminopropyl)-3-ethylcarbodiimide hydrochloride (Aldrich Chemical Co.) dissolved in 1 ml distilled water is added dropwise while constantly stirring. Thereafter, the pH is readjusted to 4.5 and the coupling reaction is allowed to proceed overnight under constant stirring. Acetic acid (200 μl) is added for another 4 hr to block the remaining amino groups on the matrix. Finally, the matrix material is washed several times alternatively with 0.1M acetate buffer, pH 4.0, 0.5M NaCl, and 0.1M sodium bicarbonate buffer, pH 8.3, 0.5M NaCl, and suspended in Tris-buffered saline for storage.

For immunoaffinity chromatography, 0.5 ml of MS2/TSG-14 Sepharose is equilibrated with Tris-buffered saline (20 mM Tris, 0.5M NaCl, pH 7.5) containing 0.05% Tween-20 (TTBS). One ml of antiserum raised against the TrpE/TSG-14 fusion protein is mixed with 0.5 ml MS2/TSG-14 Sepharose and 0.5 ml TTBS, and the mixture incubated in a cryotube at 4° C. overnight under constant rotation. The suspended solid phase matrix material is transferred to a centrifuge tube and washed with 10 ml TTBS. Thereafter, the sediment is transferred to an Eppendorf tube, centrifuged (14,000 rpm, 2 min.) and the supernatant carefully removed. One ml 0.1M glycine-HCl buffer, pH 2.5, is added and the gel is shaken for 2 min. After further centrifugation, the supernatant is immediately neutralized with solid Tris. This results in the production of a specific antiserum for TSG-14.

EXAMPLE XII

Detection of Natural and Recombinant TGS-14 Protein from TNF-Treated FS-4 Cells and Cells Transfected with a TSG-14 Expression Vector Experiments are conducted to localize TSG-14 protein in the supernatants or extracts of either (a) FS-4 cells treated with TNF for 9 hours, or (b) cells transfected with TSG-14 cDNA.

After the cells (either normal FS-4 or TSG-14-transfected cells) are grown to confluence, the medium is removed and replenished with serum-free medium. The FS-4 cells are either stimulated with 20 ng/ml TNF or left untreated. After 7 to 24 hours, the medium is collected and concentrated up to 100-fold in an Amicon apparatus. Cell pellets are also collected and dissolved in SDS-PAGE sample buffer. Samples are subjected to Western blot analysis with the aid of immunopurified antiserum against TSG-14 protein.

The major band which was specifically recognized by the immunopurified antiserum is detected in the culture supernatants of both TNF-treated FS-4 cells and TSG-14 transfected cells, but not of control cells. This protein migrates at an apparent molecular weight of 40–42 kDa on SDS-PAGE.

EXAMPLE XIII

Complete DNA Sequence of TSG-14

MATERIALS AND METHODS

Material. *Escherichia coli*-derived recombinant human TNF-α (specific activity, $3 \times 10^7$ U/mg) and *E. coli*-derived recombinant murine TNF-α (specific activity, $6\xi10^6$ U/mg) were supplied by M. Tsujimoto of the Suntory Institute for Biomedical Research, Osaka, Japan. Human TNF-α was used in all experiments unless specified. *E. coli*-derived recombinant human IL-1α (specific activity, $1 \times 10^9$ U/mg) was a gift of Alvin Stern and Peter Lomedico, Hoffmann-LaRoche, Inc., Nutley, N.J. *E. coli*-derived recombinant human IL-6 (specific activity, $5 \times 10^6$ U/mg) was supplied by T. Kishimoto of the Institute for Molecular and Cellular Biology, Osaka University, Osaka, Japan, and is readily available from commercial sources. Dexamethasone sodium phosphate was purchased from LymphoMed, Rosemont, Ill. Cycloheximide was purchased from Sigma Chemical Co., St. Louis, Mo.

Cell cultures. Normal human diploid foreskin FS-4 fibroblasts and the immortalized FS-4SV7 fibroblast line (kindly provided by Jedd Wolchok, New York University Medical Center) and is commercially available (e.g., from the ATCC, Rockville, Md.) were maintained in MEM supplemented with 5% fetal bovine serum (FBS). The human umbilical vein endothelial cells (HUVEC) were kindly provided by Dr. Richard Levin (New York University Medical Center), are commercially available (e.g., from ATCC, Rockville, Maryland), and maintained in α-MEM supplemented in 20% FBS and basic fibroblast growth factor (10 ng/ml; a gift from Dr. D. Moscatelli, New York University Medical Center) and is commercially available (e.g., from the ATCC, Rockville, Md). The human hepatoma cells (HepG2) were maintained in MEM supplemented with 10% FBS. Human lung carcinoma (A549), human colon adenocarcinoma (Colo-205 and HT29), and the human rhabdomyosarcoma cell lines (A673) were maintained in DMEM containing 10% FBS. The human cutaneous malignant melanoma cell line SK-MEL-19 (kindly provided by Dr. Alan Houghton, Memorial Sloan-Kettering Cancer Center, New York) and is commercially available (e.g., from the ATCC, Rockville, Md.) was grown in MEM supplemented with 10% FBS. Mouse embryo fibroblasts were isolated from normal embryos by treatment with trypsin and cultured in MEM supplemented with 10% FBS.

Sequence Analysis. Four overlapping k clones that cross-hybridized with the TSG-14 cDNA (Lee et al., 1990, *Mol. Cell. Biol.*, 10:1982.) were chosen for full-length sequencing. The inserts were subcloned into the EcoRI site of M13mp18 bacteriophage. Single-stranded DNA templates from recombinant M13 clones were prepared, and overlapping sequences from each end of the cDNA were determined by the dideoxynucleotide chain termination method, utilizing the Sequenase kit from United States Biochemical Corp. (Cleveland, Ohio). Analysis of the sequence was performed on a Macintosh IIci computer using DNA Strider (version 1.0) and the Genetics Computer Group Sequence Analysis Software Package, version 7.1 (Marck, 1988, *Nucl. Acid Res*, 16:1829.; Bilofsky et al., 1986, *Nucl. Acid. Res.* 14:1). The cDNA and predicted amino acid sequences were compared with sequences entered in GenBank (release 72.0), EMBL (31.0), SwissProt (22.0), and the translated GenBank (72.0) using the FASTA algorithm (Devereux, et al., 1984, *Nucl. Acid Res.*, 12:387.).

In vitro transcription and translation. The TSG-14 cDNA was cloned into the vector pGEM7zf(+) (Promega Corp., Madison, Wis.). For deletion analysis, the recombinant vector was linearized at the SacII, NdeI, or BamHI sites. For translation experiments in the presence of microsomes, the recombinant vector was linearized at the BamHI site only. The linearized vectors were transcribed and capped in vitro from the T7 promoter using a kit available from Stratagene (La Jolla, Calif.). The newly synthesized transcripts were then translated in vitro with a rabbit reticulocyte lysate system (Promega, Madison, Wis.) in the presence of [$^{35}$S] L-methionine (sp. act.$\geq$1000 Ci/mmol; final concentration =0.8 mCi/ml) (ICN Biochemicals, Inc. Costa Mesa, Calif.). To analyze processing of the products of in vitro translation, transcripts were incubated in the presence of canine pancreatic microsomes (Promega, Madison, Wis.). The translation products were incubated for 5 min with 1 mM tetracaine HCl (Sigma Chemical Co., St. Louis, Mo.) at room temperature and were then treated with proteinase K to a final concentration of 0.1 mg/ml (Stratagene, La Jolla, Calif.), in the presence or absence of 1% Triton X-100. To an aliquot of the newly translated product was added 1 U of N-glycosidase F (Boehringer-Mannheim Corp., Indianapolis, Ind.) and 2× 'endo-F' buffer (80 mM sodium phosphate, pH 7.2, 50 mM EDTA, 4% Triton X-100, 0.3% SDS and 2% 2-mercaptoethanol), and the mixture was incubated for 1 h at 37° C. Translation products were run on a 10% SDS-polyacrylamide gel at a constant current of 40 mA, and exposed to X-ray film at room temperature.

Northern bolt analysis. Cell pellets were prepared, and in most cases total RNA was isolated by the acid guanidium-thiocyanate-phenol-chloroform extraction method (Chomczynski, and Saachi, 1987, *Anal. Biochem.*, 162:156.), except for the FS-4 fibroblasts, from which RNA was isolated by a method described elsewhere (Lin and Vilcek, 1987, *J. Biol. Chem.*, 262:11908). Ten mg of total RNA was fractionated on a 1% agarose gel containing formaldehyde and transferred onto nylon membranes (Nytran, Schleicher & Schuell, Keene, N.H.). Filters were hybridized with a $^{32}$P-labeled 0.9 kb TSG-14 cDNA insert from recombinant M13 clones, and with 32P-labeled internal reference pHe7 cDNA (provided by P. B. Sehgal, Rockefeller University, New York, N.Y.). Except where noted, the hybridized filters were washed twice in 0.1×SSC, 0.1% SDS at room temperature and twice in 0.1×SSC, 0.1% SDS at 65° C. The blots were exposed to Kodak XAR or Fuji RX X-ray film at −70° C.

Nuclear run-on analysis was performed essentially as described by Larner et al., 1984, *Proc. Natl. Acad. Sci. USA* 81:6733, Oliveira, et al., 1992, *Proc. Natl. Acad. Sci. USA*, (in press)). Briefly, FS-4 cells were treated with 20 ng/ml TNF and/or 10 mg/ml cycloheximide for 30 min. The cells were then rinsed and scraped off dishes in ice-cold PBS. The nuclei were collected by centrifugation after disrupting the cells with a "b" pestle glass Dounce homogenizer and washed once in reaction buffer (20 mM Tris 7.5, 10 mM MgCl2, 140 mM KCl, 20% glycerol and 0.5 mM dithiothreitol). The nuclei were then resuspended in the same buffer containing 0.5 mM each of ATP, CTP, GTP, 5 mM of UTP and 0.2–0.3 mCi of [$\alpha^{32}$p] UTP (3000 Ci/mM) (ICN Biochemical, Inc., Costa Mesa, Calif.). The elongation reaction was allowed to proceed for 15 min at 30° C., and the templates were then digested with 200 U of RNase-free DNase I (Boehringer Mannheim, Indianapolis, Ind.). The labeled RNA was extracted with phenol and phenol-chloroform, and TCA-precipitated. TSG-14 cDNA or a cDNA corresponding to the internal reference gene glyceraldehyde 3-phosphate dehydrogenase (GAPDH; kindly provided by C. Basilico, New York University Medical Center) were cloned into the vector pGEM7zf(+); the vector without a cloned insert was used as a negative control. Plasmids containing the sequences of interest were alkali-denatured and immobilized on nylon membranes (Schleicher & Schuell, Keene, N.H.). After pre-hybridization for 2–3 h in TESS2D (10 mM TES (N-Tris [hydroxymethyl] methyl-2-aminoethanesulfonic acid) pH 7.4, 2×x Denhardt's solution, 400 mM NaCl, 4 mM EDTA, 0.1% SDS, 200 mg/ml *E. coli* tRNA) the filters were hybridized overnight to the labeled nuclear probe. The hybridized filters were exposed to X-ray film at −70° C.

RESULTS

TSG-14 cDNA and Predicted Protein Sequences. Partially overlapping Aλ clones of TSG-14 cDNA obtained from the FS-4 cell cDNA library (Lee et al., 1990, *Mol. Cell. Biol.*, 10:1982.) were cloned into an M13mp18 or M13mp19 vector. Both strands were sequenced by the dideoxy chain termination method. The full-length cDNA clone was found to comprise 1839 base pairs. An untranslated 5' region of 73 nucleotides and an untranslated 3' region of 623 nucleotides flank an open reading frame that spans 1143 nucleotides (FIG. 9A) SEQ ID NO:4. A potential polyadenylation signal (AATAAA) is located in the 3' untranslated region.

The open reading frame of TSG-14 encodes a putative protein of 381 amino acids (Fig. 9A) SEQ ID NO:4. Analysis of the amino acid sequence predicts a protein of a molecular mass ca. 42 kDa and a pI value of ca. 5.42. A cleavable signal peptide sequence is predicted by a stretch of 17 hydrophobic amino acid residues at the N-terminus (FIG. 9B), suggesting that TSG-14 is a secreted protein. The predicted molecular size of the mature unglycosylated TSG-14 protein is ca. 40 kDa. A single N-glycosylation consensus sequence is present at residues 220–223 of SEQ ID NO:4. A consensus leucine zipper motif appears in the N-terminal half (residues 74–95) of SEQ ID NO:4.

Comparison of the deduced amino acid sequence of TSG-14 with other sequences in the SwissProt and EMBL protein databases revealed that TSG-14 (residues 180–381 of SEQ ID NO:4) shares some degree of homology with both C-reactive protein (CRP) (residues 25–225 of SEQ ID NO:3) and serum amyloid P-component (SAP) (residues 24–224 of SEQ ID NO:5) (Woo et al., 1985, *J. Biol. Chem.*, 260:13384; Oliveira et al., 1977, *Proc. Natl. Acad. Sci. USA*, 74:3148; Mantzouranis et al., 1985, *J. Biol. Chem.* 260:7752.), as well as other members of the pentaxin family of acute phase proteins (FIG. 10 (SEQ ID NOS:3 and 5 and residues 180–381 of SEQ ID NO:4)). The homology extends from amino acid residue 180 to the C-terminal end of TSG-14 protein. Sequence identity with human CRP is 26.5%, with an even higher degree of homology with the rabbit and mouse species of CRP. A similar degree of sequence homology exists between TSG-14 and human SAP (23.7%). In addition, a search using the MOTIFS program available from the Genetics Computer Group Sequence Analysis Software Package (Bilofsky et al., 1986, *Nucl. Acid. Res.* 14:1) indicated that a sequence motif common among the pentaxin proteins is found within the TSG-14 sequence at residues 269–276 SEQ ID NO:4. It is significant that the putative TSG-14 protein is almost twice the size of CRP and SAP, and the N-terminal half of TSG-14(SEQ ID NO:4) shows no sequence homology to other known proteins.

Figure 11B:
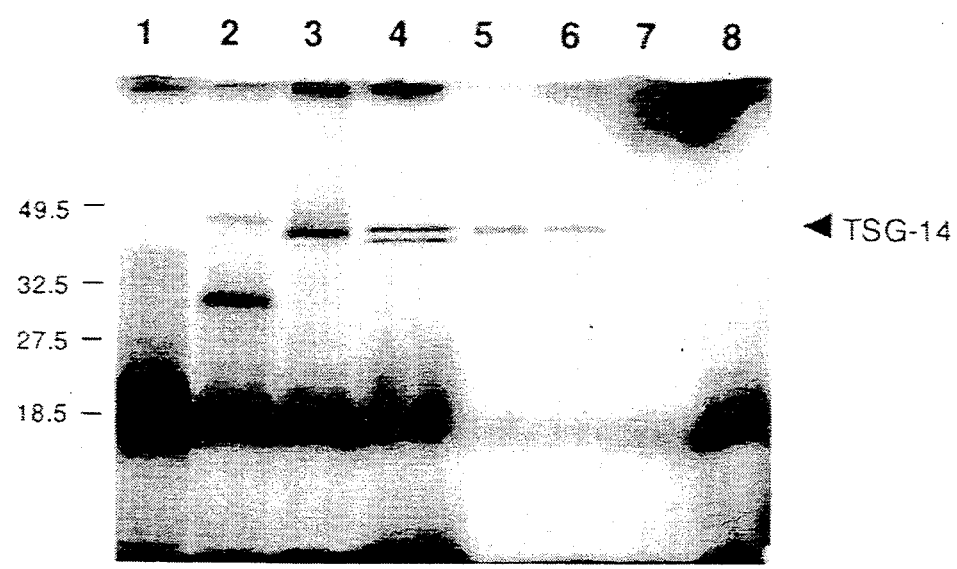
FIGS. 11A and 11B. In vitro analysis of TSG-14 protein.
Figure 11A:
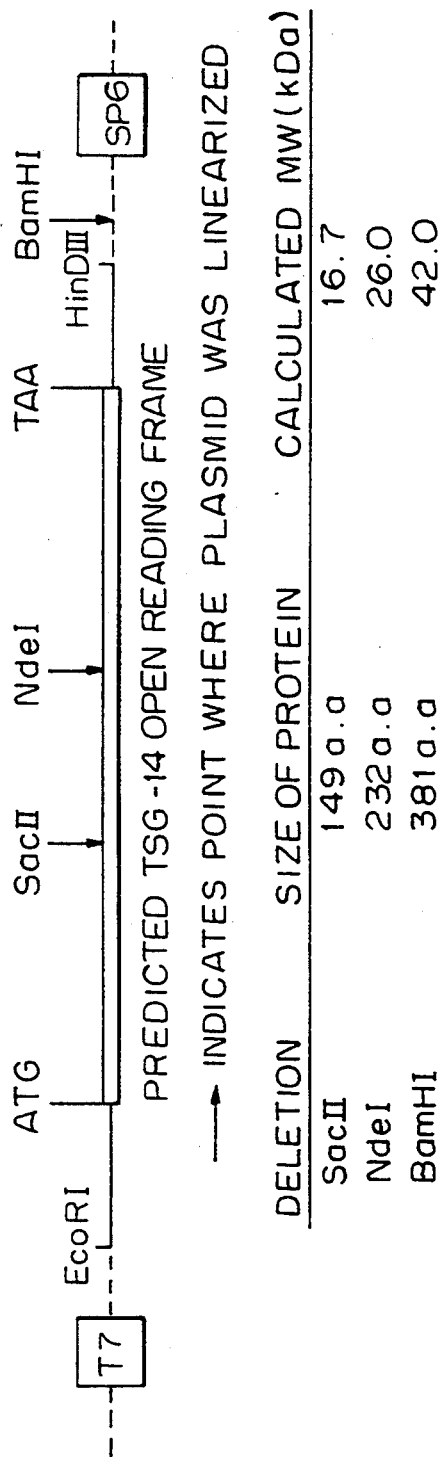

In Vitro Transcription/Translation. A cDNA insert that contained the entire open reading frame of TSG-14 was cloned into the vector pGEM7zf(+). To confirm that the size of the in vitro translated product correlated with the predicted size of TSG-14 protein, the recombinant plasmid was linearized with restriction enzymes at different points along the insert, as shown in FIG. 11a. The resulting linearized plasmids were transcribed in vitro from the SP6 promoter. The transcripts were then translated in vitro by a rabbit reticulocyte lysate system. As shown in FIG. 11B, the translation products of the SacII and NdeI transcripts (lanes 1–2) have a lower molecular weight (ca. 19 and 30 kDa, respectively) than the translation product of the BamHI transcript (lane 3), which encompasses the entire predicted open reading frame of TSG-14, SEQ ID NO:4. The apparent molecular weight of the BamHI translation product is ca. 44.5 kDa, which is close to the value of the predicted molecular weight of ca. 42 kDa for the unglycosylated TSG-14 protein with its signal peptide.

To confirm the predictions that TSG-14 is a secretory protein and that it is N-glycosylated, the BamHI transcript was translated in vitro in the presence of canine pancreatic microsomes (lanes 4–7). The major translation product migrated with a molecular weight of 45.5 kDa, apparently representing the glycosylated TSG-14 protein devoid of the signal peptide sequence (lanes 5 and 6). A faster migrating faint band (ca. 43 kDa) seen in lanes 5 and 6 probably represents the unglycosylated TSG-14 protein because treatment with N-glycosidase F (lane 4) led to an increase in the intensity of a band with identical migration characteristics. Treatment with proteinase K in the absence of Triton X-100 had no effect on the appearance of the 45.5 and 43 kDa bands (lane 6), indicating that the protein was able to translocate into the microsome and that, therefore, the protein possesses a signal peptide. Upon solubilization of the microsomal membrane with Triton X-100, the protein became accessible to the action of the protease and was degraded (lane 7).

Figure 12A:
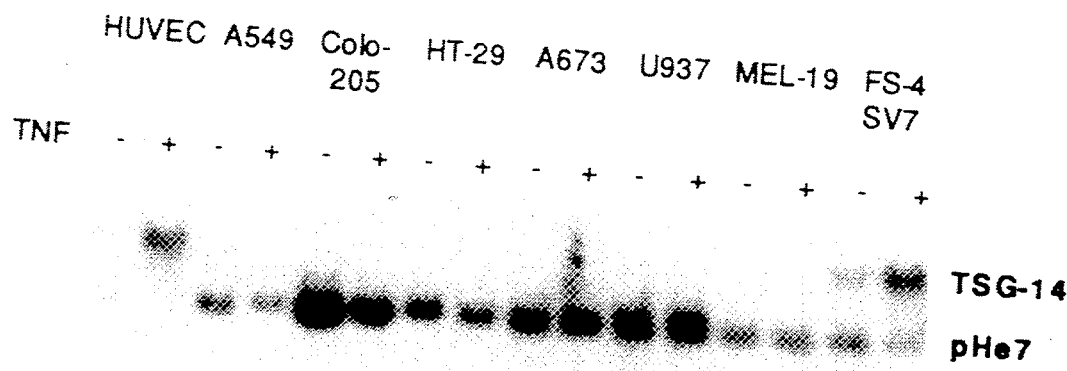
FIGS. 12A–12C. Northern blot analysis of TSG-14 mRNA expression in different cell types. RNA was fractionated on an agarose gels blotted onto nylon membrane and hybridized with TSG-14 and pHe7 cDNAs. 12A: Cultures were incubated in control medium or medium with TNF (20 ng/ml) for 4 h. HUVEC, human umbilical vein endothelial cells; A549, human lung carcinoma; Colo-205, human colon adenocarcinoma, HT-29, human colon adenocarcinoma; A673, human rhabdomyosarcoma; U937, human macrophage-like histiocytic lymphoma cell line; SK-MEL19, human cutaneous malignant melanoma. 12B: HepG2 human hepatoma cells were incubated for 4 h in control medium (CTRL) or medium containing IL-6 (500 ng/ml), TNF (20 ng/ml), In-1 (1 ng/ml), dexamethasone (DEX) (4 mg/ml), or cycloheximide (CHX) (10 mg/ml). The two right-hand lanes show TSG-14 mRNA expression in control and IL-1 treated (1 ng/ml; 8 h) FS-4 cells, respectively. 12C: Murine embryo fibroblasts were incubated for 4 h in control medium or medium containing cycloheximide (10 mg/ml), human TNF (20 ng/ml), murine TNF (20 or 40 ng/ml), human IL-1 (1 ng/ml) or combinations of these treatments. Right-hand lane shows TSG-14 mRNA expression in FS-4 cells treated with human TNF (20 ng/ml) for 4 h.
Figure 12B:
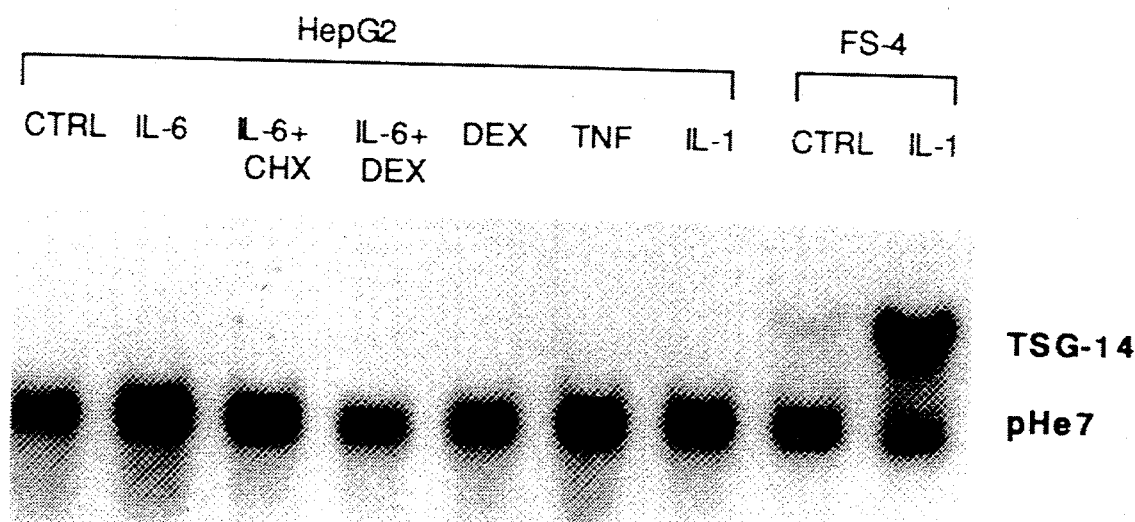
Figure 12C:
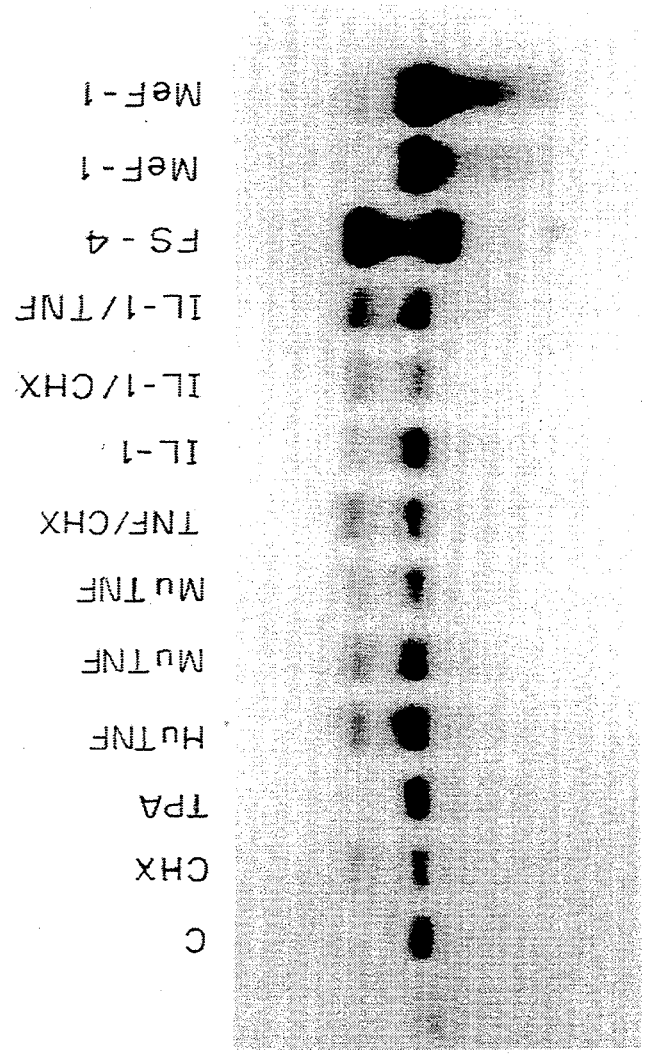

Patterns of Induction of TSG-14 mRNA. The mRNA of TSG-14 was previously shown to be rapidly induced to a high level by TNF in FS-4 cells, with a plateau reached by 4 h (Lee et al., 1990, Mol. Cell. Biol., 10:1982.). Other cell lines were examined for their ability to express TSG-14 mRNA in response to treatment with TNF. Normal human umbilical vein endothelial cells (HUVEC), expressed TSG-14 in response to TNF, as did FS-4 cells immortalized by transfection with the large T antigen of SV-40 virus (FS-4SV7 cells) (FIG. 12A). However, several transformed cell lines of tumor origin failed to express detectable levels of TSG-14 mRNA in response to TNF. Interestingly, the human hepatoma cell line HepG2, which had previously been shown to express high levels of acute phase products in response to IL-1, IL-6 and dexamethasone (Baumann et al., 1989, Ann. N.Y. Acad. Sci., 557:280), also did not express TSG-14 mRNA in response to a 4 h treatment by a variety of stimuli (FIG. 12B). To determine whether mouse cells can produce TSG-14 mRNA, RNA was extracted from normal mouse embryo fibroblasts treated with murine or human TNF or with human IL-1 and was probed with the same human cDNA fragment as used in the previous Northern blots. The hybridized filters were washed at low stringency (2 washes with 2×SSC, 0.2% SDS, 65° C./1 h). A mouse homolog of TSG-14 mRNA, of a size similar to human TSG-14 mRNA, was induced by both TNF and IL-1, and also by cycloheximide (FIG. 12C).

Figure 13:
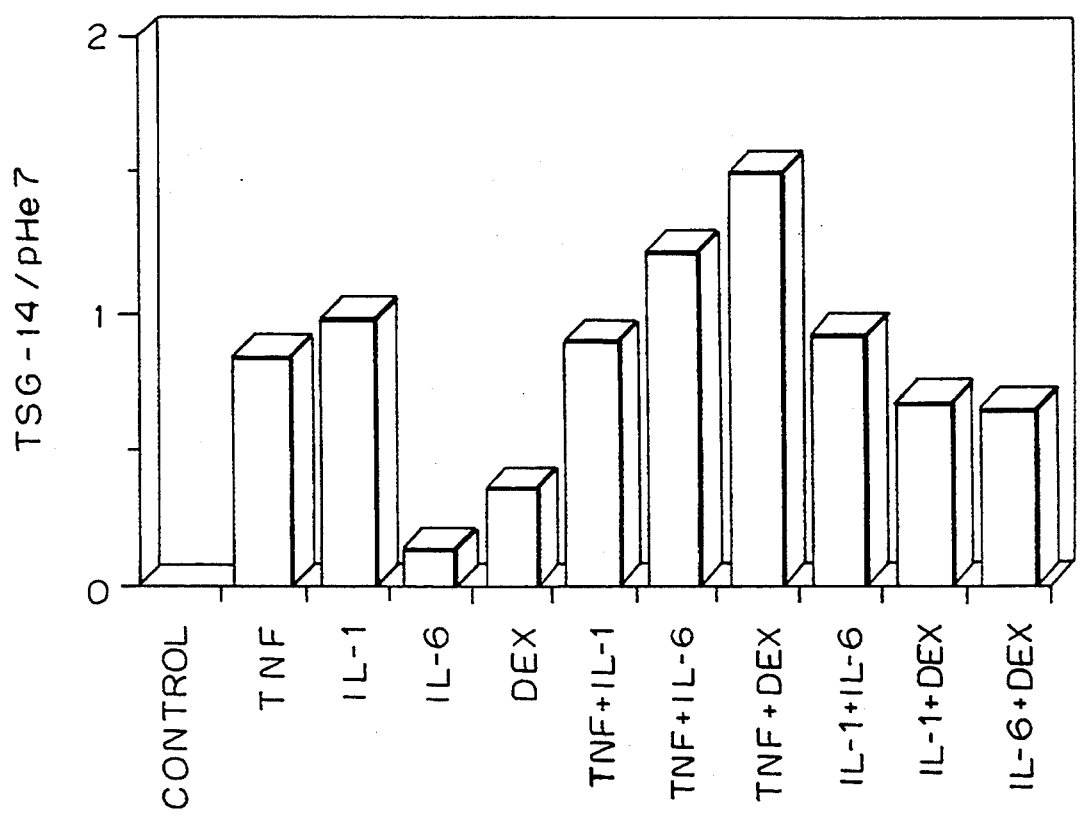
FIG. 13. Patterns of TSG-14 mRNA induction in FS-4 cells. Growth arrested FS-4 cells were incubated for 4 h with control medium or medium containing TNF (20 ng/ml), In-1 (1 ng/ml), IL-6 (500 ng/ml) or dexamethasone (4 mg/ml), or combinations of these agents. TSG-14 and pHe7 mRNAs were analyzed by Northern blotting. To quantitate levels of TSG-14 mRNA, bands on X-ray film were scanned with the aid of the Ambis optical imaging system (San Diego, Calif.). To normalize for the amount of RNA loaded, the values on the y-axis represent the ratio between the TSG-14 and pHe7 signals.

IL-1, IL-6 and dexamethasone, which are known to modulate the acute phase response (Baumann et al., 1989, Ann. N.Y. Acad. Sci., 557:280; Baumann et al,. 1990, J. Biol. Chem., 265:22275; Crowl et al., 1991, J. Biol. Chem., 266:2647; Ganapathi et al., 1991, J. Immunol., 147:1261.), were also able to induce TSG-14 mRNA in FS-4 cells (FIG. 13). When examined after 4 h of treatment, IL-6 and dexamethasone were less effective than TNF or IL-1 in increasing steady-state levels of TSG-14 mRNA. However, the latter agents may be inducing TSG-14 mRNA with faster kinetics. Other experiments showed that longer periods of treatment with dexamethasone resulted in much higher mRNA levels (data not shown), whereas on TNF treatment TSG-14 mRNAs plateaued after 4 h (Lee et al., 1990, Mol. Cell. Biol., 10:1982.). It is interesting that combinations of TNF with IL-6, TNF with dexamethasone and IL-6 with dexamethasone resulted in at least additive stimulations of TSG-14 mRNA, while less than additive effects, and possibly even some antagonisms, were seen with combinations of IL-1 with TNF, IL-6 or dexamethasone (FIG. 13).

Nuclear Run-on Analysis. FS-4 nuclei were labeled with $^{32}$P-dUTP and the rate of synthesis of nascent transcripts was determined by a nuclear run-on assay. Treatment of FS-4 cells with TNF strongly activated the transcription of the TSG-14 gene (FIG. 13). Co-treatment of the cells with the protein synthesis inhibitor cycloheximide and TNF showed a similar degree of transcriptional activation as TNF alone, suggesting that de novo protein synthesis is not necessary for the transcriptional activation of the TSG-14 gene.

Figure 9B:
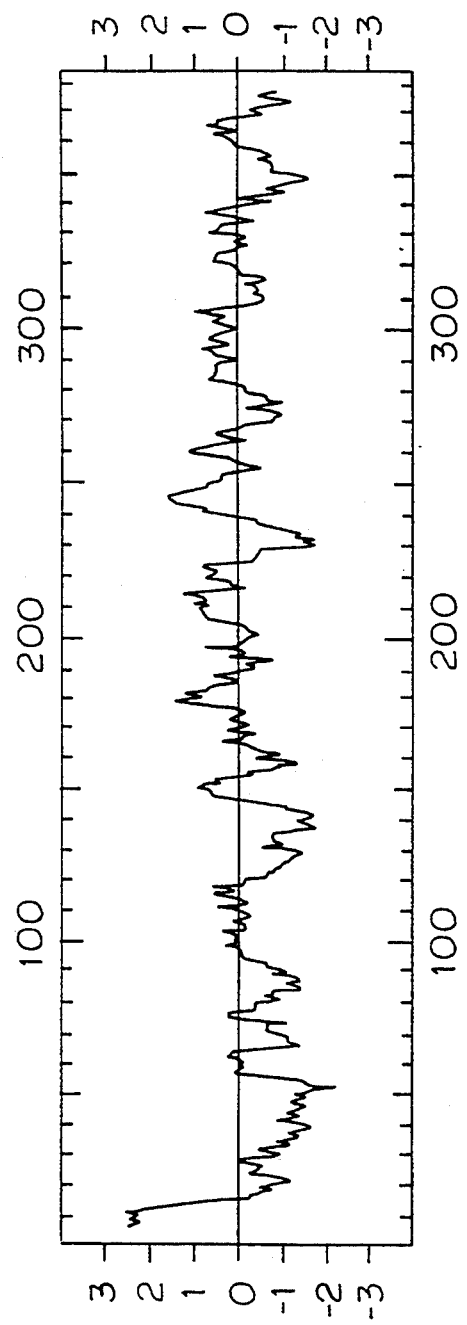

According to the present invention, TSG-14 cDNA, originally isolated from a cDNA library derived from TNF-treated normal human FS-4 fibroblasts (Lee et al., 1990. Mol. Cell. Biol., 10:1982.), encodes a novel member of the pentaxin family of acute phase proteins, structurally related to C-reactive protein and serum amyloid P-component (Woo et al., 1985, J. Biol. Chem., 260:13384, Oliveira et al., 1977, Proc. Natl. Acad. Sci. USA, 74:3148; Mantzouranis et al., 1985, J. Biol. Chem. 260:7752). Full-length TSG-14 cDNA consists of 1839 base pairs (FIG. 9A(SEQ ID NO:4). An open reading frame encoding a putative protein of 381 amino acids is flanked by a short 5'-untranslated region and a longer 3'-untranslated region. A polyadenylation signal is present in the 3'-untranslated region. Analysis of the amino acid sequence revealed several key features. The protein contains an apparent signal sequence at its amino terminus, as determined by a hydrophobicity plot of the protein (FIG. 9B). When translated in vitro in the presence of microsomes, the protein translocates across the membrane (FIG. 11B), indicating that it is indeed secreted. A change in the migration pattern after treatment of the in vitro translated protein with endoglycosidase F confirmed the prediction that the protein contains an N-glycosylation site (FIG. 11B).

Most significant, however, was the finding that the predicted TSG-14 protein (residues 180–381 of SEQ ID NO:4) shares a high degree of sequence homology with two acute phase proteins, C-reactive protein (CRP)

(SEQ ID NO:3) and serum amyloid P-component (SAP) (SEQ ID NO:5) (FIG. 10). In addition, a sequence motif which is common among the pentaxin family of proteins is also present in the TSG-14 sequence (FIG. 9A(SEQ ID NO:4)). A characteristic of the pentaxin proteins is that they have a discoid arrangement of 5 noncovalently bound subunits (Gordon and Koj, 1985, The acute-phase response to injury and infection. Elsevier Science Publishers B.V., The Netherlands.). The homology extends from residue 180 to the C-terminal end (residue 381 (SEQ ID NO:4)) of TSG-14, or roughly over half of the protein. This region corresponds to the entire CRP and SAP protein sequences. Although human CRP in not glycosylated, most of the other members of the pentaxin family of proteins are, including SAP (Woo et al., 1985, *J. Biol. Chem.*, 260:13384.). The N-terminal half of TSG-14 protein (n-terminus of SEQ ID NO:4) shares no significant homology with sequences available in the various databases. Interestingly, the N-terminal region of the protein contains a preponderance of acidic amino acid residues; the calculated pI value of the protein is 542. Furthermore, a consensus leucine zipper motif has been identified in the N-terminal half of TSG-14 protein (residues 74–95 of SEQ ID NO:32). This domain is involved in the dimerization of protein subunits (Landschulz et al., 1988, *Science*, 240:1759); as far as we know, no leucine zipper motifs have been identified in other acute phase proteins. In spite of the unique characteristics of the N-terminal half of the protein, the overall sequence homology strongly suggests that TSG-14 is a novel member of the pentaxin family of proteins.

In the intact organism, acute phase proteins are produced mainly by the liver, in response to a variety of stimuli, including infection, tissue injury, and certain malignancies, with serum levels of many acute phase proteins rising dramatically (Gordon and Koj, 1985, The acute-phase response to injury and infection. Elsevier Science Publishers B.V., The Netherlands.). Collectively, acute phase proteins are thought to play the role of a non-specific, first-line defense against systemic insult. Our failure to detect TSG-14 mRNA in the HepG2 cell line of hepatoma cells in response to a variety of inducing agents (FIG. 12B) does not indicate a lack of expression of the TSG-14 gene in hepatocytes of the normal liver. Rather, lack of expression in HepG2 cells is likely to reflect the fact that most virus-transformed or malignant tumor-derived cell lines in general appear to have lost the ability to express TSG-14 mRNA (FIG. 12A and data not shown). A lack of expression in transformed cells was also noted with TSG-6, a TNF- and IL-1-inducible hyaluronate-binding protein identified from the same cDNA library as TSG-14 (Lee et al., 1992, *J. Cell. Biol.*, 116:545.).

Figure 14:
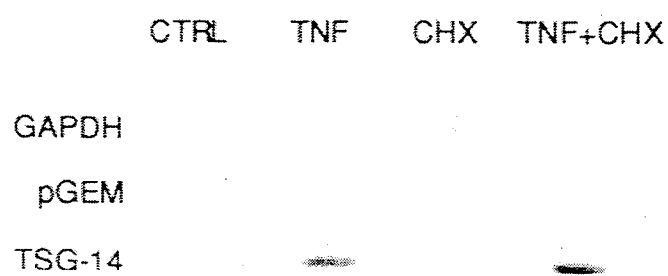
FIG. 14. Nuclear run-on analysis. Autoradiograms of hybridized filters represent newly synthesized TSG-14 and GAPDH (internal control) transcripts from FS-4 cells treated with TNF (20 ng/ml) or cycloheximide (10 mg/ml) for 30 min. The vector pGEM7zf(+) was used as a negative control.

TSG-14 is expected to be a novel acute phase protein, based on the pattern of TSG-14 mRNA expression seen in the FS-4 fibroblasts after treatments with TNF, IL-1, IL-6 and dexamethasone (FIG. 14). Based on their patterns of gene regulation, two major classes of acute phase genes have been described (Baumann et al., 1990, *J. Biol. Chem.;* 265:22275; Hocke et al., 1992, *Mol. Cell. Biol.* 12:2282; Stadnyk et al., 1991, *Immunol. Today*, 12:A7.). Class 1 genes are regulated mainly by IL-1, TNF, combinations of IL-1/TNF and IL-6, and combinations of these cytokines with glucocorticoids. Among genes of this class are those encoding the human C-reactive protein, serum amyloid A, complement C3, haptoglobin, and $\alpha_1$-acid glycoprotein. Class 2 genes are regulated mainly by IL-6 and combinations of IL-6 and glucorticoids, and include the genes for thiostatin, fibrinogen, $\alpha_1$-antitrypsin, and $\alpha_1$-antichymotrypsin. TSG-14 mRNA is highly inducible by IL-1 and TNF, and to a lesser extent by the glucocorticoid dexamethasone (FIGS. 12A–12C and 13). The cytokine IL-6, while by itself not a strong inducer of TSG-14 message, appears to potentiate the induction by TNF and dexamethasone (FIG. 13). Hence, the overall pattern of induction of the TSG-14 gene is rather characteristic for the class 1 acute phase genes. It should be noted that the low level of TSG-14 mRNA induction by IL-6 could be due to the relatively low numbers of cell surface IL-6 receptors on FS-4 cells (Snyers et al., 1989, *Ann. N.Y. Acad. Sci.*, 557:388). Dexamethasone has been shown to upregulate high-affinity IL-6 receptors on human epithelial cells (Snyers et al., 1990, *Proc. Natl. Acad. Sci. USA*, 87:2838); a similar mechanism in FS-4 cells may be responsible for the combined actions of IL-6 and dexamethasone on the induction of TSG-14 mRNA. Little or no induction of TSG-14 message was seen by growth factors not normally associated with the acute phase response, such as EGF, TGF-Z$\beta$, or PDGF (Lee et al., 1990, *Mol. Cell. Biol.*, 10:1982.).

It was also found TSG-14 mRNA to be inducible by TNF and IL-1 in normal murine fibroblasts (FIG. 12C). Both CRP and SAP are highly conserved in different species, perhaps reflecting the role these proteins play in more primitive immune systems (Gordon and Koj, 1985, The acute-phase response to injury and infection. Elsevier Science Publishers B.V., The Netherlands.).

As a member of the pentaxin family of acute-phase proteins, TSG-14 may have functions similar to CRP and SAP. CRP was first described for its ability to bind pneumococcal C-polysaccharide (Kaplan and Volonakis, 1974, *J. Immunol.* 112:2135.; Marck, 1988, *Nucl. Acid Res.* 16:1829.). Both CRP and SAP have been shown to bind phosphatidylcholine in a calcium-dependent manner (Marck, 1988, *Nucl. Acid Res.* 16:1829; Volonakis et al., 1981, *J. Immunol.* 126:1820). Functions previously ascribed to these proteins include activation of complement (Kaplan and Volonakis, 1974, *J. Immunol.* 112:2135.; Jiang, et al., 1991, *J. Immunol.* 146:2324.), aid in the opsonization of particles for ingestion by neutrophils and macrophages (Marck, 1988, *Nucl. Acid Res.* 16:1829; Kilpatrick and Volonakis, 1985, *J. Immunol.*, 134:3364; Mortensen et al., 1976, *J. Immunol.*, 117: 774), and initiation of tumoricidal activity in macrophages (Zahedi and Mortensen, 1986, *Cancer Res.* 46:5077; Barna et al., 1987, *Cancer Res.* 47:3959). On the other hand, the structural differences between TSG-14 and the other pentaxin proteins, particularly the presence of a distinct N-terminal half in TSG-14, suggest that TSG-14 may have functions that are different from those of CRP and SAP.

Significantly, the expression of TSG-14 mRNA appears to be limited to normal cells; transformed lines of fibroblasts, as well as several malignant tumor-derived cell lines apparently have lost the ability to express TSG-14 in response to TNF. Loss of TSG-14 expression in transformed cells, along with the loss of expression of other cytokine-inducible proteins (Lee et al., 1992, *J. Cell. Biol.*, 116:545.), may be related to the change from the normal to malignant phenotype. The lack of expression of some of these proteins might contribute to the ability of malignant cells to escape immune surveillance.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references.

Additionally, the entire contents of the references cited within the references cited herein are also entirely incorporated by reference. Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

---

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1836 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 73..606

( x i ) SEQUENCE DESCRIPTION: SEQ ID NO:1:

```
AATTCGCGCT  CAACTCAGCT  CACTGAGAGT  CTCTCCCGCC  AGCTGTGGAA  AGAACT                    60

GTCTCTCCAG CA ATG CAT CTC CTT GCG ATT CTG TTT TGT GCT CTC TGG                        108
              Met His Leu Leu Ala Ile Leu Phe Cys Ala Leu Trp
                1           5                   10

TCT GCA GTG TTG GCC GAG AAC TCG GAT GAT TAT GAT CTC ATG TAT GTG                      156
Ser Ala Val Leu Ala Glu Asn Ser Asp Asp Tyr Asp Leu Met Tyr Val
            15                  20                  25

AAT TTG GAC AAC GAA ATA GAC AAT GGA CTC CAT CCC ACT GAG GAC CCC                      204
Asn Leu Asp Asn Glu Ile Asp Asn Gly Leu His Pro Thr Glu Asp Pro
        30                  35                  40

ACG CCG TGC GAC TGC GGT CAG GAG CAC TCG GAA TGG GAC AAG CTC TTC                      252
Thr Pro Cys Asp Cys Gly Gln Glu His Ser Glu Trp Asp Lys Leu Phe
 45                  50                  55                  60

ATC ATG CTG GAG AAC TCG CAG ATG AGA GAG CGC ATG CTG CTG CAA GCC                      300
Ile Met Leu Glu Asn Ser Gln Met Arg Glu Arg Met Leu Leu Gln Ala
                    65                  70                  75

ACG GAC GAC GTC CTG CGG GGC GAG CTG CAG AGG CTG CGG GAG GAG CTG                      348
Thr Asp Asp Val Leu Arg Gly Glu Leu Gln Arg Leu Arg Glu Glu Leu
                80                  85                  90

GGC CGG CTC GCG GAA AGC CTG GCG AGG CCG TGC GCG CCG GGG GCT CCC                      396
Gly Arg Leu Ala Glu Ser Leu Ala Arg Pro Cys Ala Pro Gly Ala Pro
```

|   |   |   |   |   |   |   |   |   |   |   |   |   |   |   |   |   |
|---|---|---|---|---|---|---|---|---|---|---|---|---|---|---|---|---|
| GCA | GAG | GCC | AGG | CTG | ACC | AGT | GCT | CTG | GAC | GAG | CTG | CTG | CAG | GCG | ACC | 444 |
| Ala | Glu 110 | Ala | Arg | Leu | Thr | Ser 115 | Ala | Leu | Asp | Glu | Leu 120 | Leu | Gln | Ala | Thr |  |
| CGC | GAC | GCG | GGC | CGC | AGG | CTG | GCG | CGT | ATG | GAG | GGC | GCG | GAG | GCG | CAG | 492 |
| Arg 125 | Asp | Ala | Gly | Arg | Arg 130 | Leu | Ala | Arg | Met | Glu 135 | Gly | Ala | Glu | Ala | Gln 140 |  |
| CGC | CCA | GAG | GAG | GCG | GGG | CGC | GCC | CTG | GCC | GCG | GTG | CTG | AGG | AGC | TGC | 540 |
| Arg | Pro | Glu | Glu 145 | Ala | Gly | Arg | Ala | Leu 150 | Ala | Ala | Val | Leu | Arg 155 | Ser | Cys |  |
| GGC | GAC | GCG | AGC | CGA | CCT | GCA | CGC | GGT | GCA | GGG | CTG | GGC | TGC | CCG | GAG | 588 |
| Gly | Asp | Ala | Ser 160 | Arg | Pro | Ala | Arg | Gly 165 | Ala | Gly | Leu | Gly | Cys 170 | Pro | Glu |  |
| CTG | GCT | GCC | GGC | AGG | TTG | TGAAACAGCT | ATTTTATTCC | CAATGCGTTC | 636 |
| Leu | Ala | Ala | Gly | Arg | Leu 175 |  |  |  |  |

```
CAAGAAGATT TTTGGAAGCG TGCATCCAGT GAGACCTTTG AGGCTTGAGT CTTTTAGTGC     696
CTGCATTTGG GTCAAAGCCA CAGATGTATT AAACAAAACC ATCCTGTTTT CCTATGGCAC     756
AAAGAGGAAT CCATATGAAA TCCAGCTGTA TCTCAGCTAC CAATCCATAG TGTTTGTGGT     816
GGGTGGAGAG GAGAACAAAC TGGTTGCTGA AGCCATGGTT TCCCTGGGAA GGTGGACCCA     876
CCTGTGCGGC ACCTGGAATT CAGAGGAAGG GCTCACATCC TTGTGGGTAA ATGGTGAACT     936
GGCGGCTACC ACTGTTGAGA TGGCCACAGG TCACATTGTT CCTGAGGGAG GAATCCTGCA     996
GATTGGCCAA GAAAAGAATG GCTGCTGTGT GGGTGGTGGC TTTGATGAAA CATTAGCCTT    1056
CTCTGGGAGA CTCACAGGCT TCAATATCTG GATAGTGTT  CTTAGCAATG AAGAGATAAG    1116
AGAGACCGGA GGAGCAGAGT CTTGTCACAT CCGGGGGAAT ATTGTTGGGT GGGGAGTCAC    1176
AGAGATCCAG CCACATGGAG GAGCTCAGTA TGTTTCATAA ATGTTGTGAA ACTCCACTTG    1236
AAGCCAAAGA AAGAAACTCA CACTTAAAAC ACATGCCAGT TGGGAAGGTC TGAAAACTCA    1296
GTGCATAATA GGAACACTTG AGACTAATGA AAGAGAGAGT TGAGACCAAT CTTTATTTGT    1356
ACTGGCCAAA TACTGAATAA ACAGTTGAAG GAAAGACATT GGAAAAAGCT TTTGAGGATA    1416
ATGTTACTAG ACTTTATGCC ATGGTGCTTT CAGTTTAATG CTGTGTCTCT GTCAGATAAA    1476
CTCTCAAATA ATTAAAAAGG ACTGTATTGT TGAACAGAGG GACAATTGTT TTACTTTTCT    1536
TTGGTTAATT TTGTTTTGGC CAGAGATGAA TTTTACATTG GAAGAATAAC AAAATAAGAT    1596
TTGTTGTCCA TTGTTCATTG TTATTGGTAT GTACCTTATT ACAAAAAAA  TGATGAAAAC    1656
ATATTTATAC TACAAGGTGA CTTAACAACT ATAAATGTAG TTTATGTGTT ATAATCGAAT    1716
GTCACGTTTT TGAGAAGATA GTCATATAAG TTATATTGCA AAAGGGATTT GTATTAATTT    1776
AAGACTATTT TTGTAAAGCT CTACTGTAAA TAAAATATTT TATAAAACTA AACGGAATTC    1836
```

( 2 ) INFORMATION FOR SEQ ID NO:2:

( i ) SEQUENCE CHARACTERISTICS:
        ( A ) LENGTH: 178 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
        Met His Leu Leu Ala Ile Leu Phe Cys Ala Leu Trp Ser Ala Val Leu
         1               5                  10                  15

Ala Glu Asn Ser Asp Asp Tyr Asp Leu Met Tyr Val Asn Leu Asp Asn
                     20                  25                  30

Glu Ile Asp Asn Gly Leu His Pro Thr Glu Asp Pro Thr Pro Cys Asp
                 35                  40                  45
```

```
        Cys Gly Gln Glu His Ser Glu Trp Asp Lys Leu Phe Ile Met Leu Glu
            50                  55                  60

Asn Ser Gln Met Arg Glu Arg Met Leu Leu Gln Ala Thr Asp Asp Val
        65                  70                  75                  80

Leu Arg Gly Glu Leu Gln Arg Leu Arg Glu Glu Leu Gly Arg Leu Ala
                        85                  90                  95

Glu Ser Leu Ala Arg Pro Cys Ala Pro Gly Ala Pro Ala Glu Ala Arg
                        100                 105                 110

Leu Thr Ser Ala Leu Asp Glu Leu Leu Gln Ala Thr Arg Asp Ala Gly
                    115                 120                 125

Arg Arg Leu Ala Arg Met Glu Gly Ala Glu Ala Gln Arg Pro Glu Glu
            130                 135                 140

Ala Gly Arg Ala Leu Ala Ala Val Leu Arg Ser Cys Gly Asp Ala Ser
        145                 150                 155                 160

Arg Pro Ala Arg Gly Ala Gly Leu Gly Cys Pro Glu Leu Ala Ala Gly
                        165                 170                 175

Arg Leu
```

(2) INFORMATION FOR SEQ ID NO:3:

(i) SEQUENCE CHARACTERISTICS:
(A) LENGTH: 201 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:3:

```
        Arg Lys Ala Phe Val Phe Pro Lys Glu Ser Asp Thr Ser Tyr Val Ser
        1               5                   10                  15

Leu Lys Ala Pro Leu Thr Lys Pro Leu Lys Ala Phe Thr Val Cys Leu
                        20                  25                  30

His Phe Tyr Thr Glu Leu Ser Ser Thr Arg Gly Tyr Ser Ile Phe Ser
                    35                  40                  45

Tyr Ala Thr Lys Arg Gln Asp Asn Glu Ile Leu Ile Phe Trp Ser Lys
        50                  55                  60

Asp Ile Gly Tyr Ser Phe Thr Val Gly Gly Ser Glu Ile Leu Phe Glu
        65                  70                  75                  80

Val Pro Glu Val Thr Val Ala Pro Val His Ile Cys Thr Ser Trp Glu
                        85                  90                  95

Ser Ala Ser Gly Ile Val Glu Phe Trp Val Asp Gly Lys Pro Arg Val
                        100                 105                 110

Arg Lys Ser Leu Lys Lys Gly Tyr Thr Val Gly Ala Glu Ala Ser Ile
                    115                 120                 125

Ile Leu Gly Gln Glu Gln Asp Ser Phe Gly Gly Asn Phe Glu Gly Ser
            130                 135                 140

Gln Ser Leu Val Gly Asp Ile Gly Asn Val Asn Met Trp Asp Phe Val
        145                 150                 155                 160

Leu Ser Pro Asp Glu Ile Asn Thr Ile Tyr Leu Gly Gly Pro Phe Ser
                        165                 170                 175

Pro Asn Val Leu Asn Trp Arg Ala Leu Lys Tyr Glu Val Gln Gly Glu
                        180                 185                 190

Val Phe Thr Lys Pro Gln Leu Trp Pro
                    195                 200
```

(2) INFORMATION FOR SEQ ID NO:4:

5,426,181

59 60

-continued ( i ) SEQUENCE CHARACTERISTICS:
    ( A ) LENGTH: 1839 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 74..1216

( x i ) SEQUENCE DESCRIPTION: SEQ ID NO:4:

```
GAATTCGCGC TCAACTCAGC TCACTGAGAG TCTCTCCCGC CAGCTGTGGA AAGAACTTTG          60

CGTCTCTCCA GCA ATG CAT CTC CTT GCG ATT CTG TTT TGT GCT CTC TGG           109
           Met His Leu Leu Ala Ile Leu Phe Cys Ala Leu Trp
             1               5                        10

TCT GCA GTG TTG GCC GAG AAC TCG GAT GAT TAT GAT CTC ATG TAT GTG          157
Ser Ala Val Leu Ala Glu Asn Ser Asp Asp Tyr Asp Leu Met Tyr Val
             15                  20                  25

AAT TTG GAC AAC GAA ATA GAC AAT GGA CTC CAT CCC ACT GAG GAC CCC          205
Asn Leu Asp Asn Glu Ile Asp Asn Gly Leu His Pro Thr Glu Asp Pro
         30                  35                  40

ACG CCG TGC GAC TGC GGT CAG GAG CAC TCG GAA TGG GAC AAG CTC TTC          253
Thr Pro Cys Asp Cys Gly Gln Glu His Ser Glu Trp Asp Lys Leu Phe
 45                  50                  55                  60

ATC ATG CTG GAG AAC TCG CAG ATG AGA GAG CGC ATG CTG CTG CAA GCC          301
Ile Met Leu Glu Asn Ser Gln Met Arg Glu Arg Met Leu Leu Gln Ala
                 65                  70                  75

ACG GAC GAC GTC CTG CGG GGC GAG CTG CAG AGG CTG CGG GAG GAG CTG          349
Thr Asp Asp Val Leu Arg Gly Glu Leu Gln Arg Leu Arg Glu Glu Leu
             80                  85                  90

GGC CGG CTC GCG GAA AGC CTG GCG AGG CCG TGC GCG CCG GGG GCT CCC          397
Gly Arg Leu Ala Glu Ser Leu Ala Arg Pro Cys Ala Pro Gly Ala Pro
         95                 100                 105

GCA GAG GCC AGG CTG ACC AGT GCT CTG GAC GAG CTG CTG CAG GCG ACC          445
Ala Glu Ala Arg Leu Thr Ser Ala Leu Asp Glu Leu Leu Gln Ala Thr
 110                 115                 120

CGC GAC GCG GGC CGC AGG CTG GCG CGT ATG GAG GGC GCG GAG GCG CAG          493
Arg Asp Ala Gly Arg Arg Leu Ala Arg Met Glu Gly Ala Glu Ala Gln
125                 130                 135                 140

CGC CCA GAG GAG GCG GGG CGC GCC CTG GCC GCG GTG CTA GAG GAG CTG          541
Arg Pro Glu Glu Ala Gly Arg Ala Leu Ala Ala Val Leu Glu Glu Leu
                145                 150                 155

CGG CAG ACG CGA GCC GAC CTG CAC GCG GTG CAG GGC TGG GCT GCC CGG          589
Arg Gln Thr Arg Ala Asp Leu His Ala Val Gln Gly Trp Ala Ala Arg
            160                 165                 170

AGC TGG CTG CCG GCA GGT TGT GAA ACA GCT ATT TTA TTC CCA ATG CGT          637
Ser Trp Leu Pro Ala Gly Cys Glu Thr Ala Ile Leu Phe Pro Met Arg
        175                 180                 185

TCC AAG AAG ATT TTT GGA AGC GTG CAT CCA GTG AGA CCT TTG AGG CTT          685
Ser Lys Lys Ile Phe Gly Ser Val His Pro Val Arg Pro Leu Arg Leu
    190                 195                 200

GAG TCT TTT AGT GCC TGC ATT TGG GTC AAA GCC ACA GAT GTA TTA ACC          733
Glu Ser Phe Ser Ala Cys Ile Trp Val Lys Ala Thr Asp Val Leu Asn
205                 210                 215                 220

AAA ACC ATC CTG TTT TCC TAT GGC ACA AAG AGG AAT CCA TAT GAA ATC          781
Lys Thr Ile Leu Phe Ser Tyr Gly Thr Lys Arg Asn Pro Tyr Glu Ile
                225                 230                 235

CAG CTG TAT CTC AGC TAC CAA TCC ATA GTG TTT GTG GTG GGT GAG          829
Gln Leu Tyr Leu Ser Tyr Gln Ser Ile Val Phe Val Val Gly Glu
            240                 245                 250

GAG AAC AAA CTG GTT GCT GAA GCC ATG GTT TCC CTG GGA AGG TGG ACC          877
Glu Asn Lys Leu Val Ala Glu Ala Met Val Ser Leu Gly Arg Trp Thr
```

-continued

|  |  |  |  |  |  |  | 255 |  |  |  |  | 260 |  |  |  |  | 265 |  |  |  |
|---|---|---|---|---|---|---|---|---|---|---|---|---|---|---|---|---|---|---|---|---|

```
CAC CTG TGC GGC ACC TGG AAT TCA GAG GAA GGG CTC ACA TCC TTG TGG        925
His Leu Cys Gly Thr Trp Asn Ser Glu Glu Gly Leu Thr Ser Leu Trp
    270                 275                 280

GTA AAT GGT GAA CTG GCG GCT ACC ACT GTT GAG ATG GCC ACA GGT CAC        973
Val Asn Gly Glu Leu Ala Ala Thr Thr Val Glu Met Ala Thr Gly His
285                 290                 295                 300

ATT GTT CCT GAG GGA GGA ATC CTG CAG ATT GGC CAA GAA AAG AAT GGC       1021
Ile Val Pro Glu Gly Gly Ile Leu Gln Ile Gly Gln Glu Lys Asn Gly
                305                 310                 315

TGC TGT GTG GGT GGT GGC TTT GAT GAA ACA TTA GCC TTC TCT GGG AGA       1069
Cys Cys Val Gly Gly Gly Phe Asp Glu Thr Leu Ala Phe Ser Gly Arg
            320                 325                 330

CTC ACA GGC TTC AAT ATC TGG GAT AGT GTT CTT AGC AAT GAA GAG ATA       1117
Leu Thr Gly Phe Asn Ile Trp Asp Ser Val Leu Ser Asn Glu Glu Ile
        335                 340                 345

AGA GAG ACC GGA GGA GCA GAG TCT TGT CAC ATC CGG GGG AAT ATT GTT       1165
Arg Glu Thr Gly Gly Ala Glu Ser Cys His Ile Arg Gly Asn Ile Val
    350                 355                 360

GGG TGG GGA GTC ACA GAG ATC CAG CCA CAT GGA GGA GCT CAG TAT GTT       1213
Gly Trp Gly Val Thr Glu Ile Gln Pro His Gly Gly Ala Gln Tyr Val
365                 370                 375                 380

TCA TAAATGTTGT GAAACTCCAC TTGAAGCCAA AGAAAGAAAC TCACACTTAA            1266
Ser

AACACATGCC AGTTGGGAAG GTCTGAAAAC TCAGTGCATA ATAGGAACAC TTGAGACTAA     1326

TGAAAGAGAG AGTTGAGACC AATCTTTATT TGTACTGGCC AAATACTGAA TAAACAGTTG     1386

AAGGAAAGAC ATTGGAAAAA GCTTTTGAGG ATAATGTTAC TAGACTTTAT GCCATGGTGC     1446

TTTCAGTTTA ATGCTGTGTC TCTGTCAGAT AAACTCTCAA ATAATTAAAA AGGACTGTAT     1506

TGTTGAACAG AGGGACAATT GTTTTACTTT TCTTTGGTTA ATTTGTTTT GGCCAGAGAT      1566

GAATTTTACA TTGGAAGAAT AACAAATAA GATTGTTGT CCATTGTTCA TTGTTATTGG       1626

TATGTACCTT ATTACAAAAA AAATGATGAA AACATATTTA TACTACAAGG TGACTTAACA     1686

ACTATAAATG TAGTTTATGT GTTATAATCG AATGTCACGT TTTTGAGAAG ATAGTCATAT     1746

AAGTTATATT GCAAAAGGGA TTTGTATTAA TTTAAGACTA TTTTTGTAAA GCTCTACTGT     1806

AAATAAAATA TTTTATAAAA CTAAACGGAA TTC                                  1839
```

( 2 ) INFORMATION FOR SEQ ID NO:5:

( i ) SEQUENCE CHARACTERISTICS:
( A ) LENGTH: 201 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

```
Leu Ser Gly Lys Val Phe Val Phe Pro Arg Glu Ser Val Thr Asp His
1               5                   10                  15

Val Asn Leu Ile Thr Pro Leu Glu Lys Pro Leu Gln Asn Phe Thr Leu
                20                  25                  30

Cys Phe Arg Ala Tyr Ser Asp Leu Ser Arg Ala Tyr Ser Leu Phe Ser
                35                  40                  45

Tyr Asn Thr Gln Gly Arg Asp Asn Glu Leu Leu Val Tyr Lys Glu Arg
            50                  55                  60

Val Gly Glu Tyr Ser Leu Tyr Ile Gly Arg His Lys Val Thr Pro Lys
65                  70                  75                  80

Val Ile Glu Lys Phe Pro Ala Pro Val His Ile Cys Val Ser Trp Glu
```

|  |  |  |  |  | 85 |  |  | 90 |  |  |  | 95 |  |
|---|---|---|---|---|---|---|---|---|---|---|---|---|---|
| Ser | Ser | Ser | Gly<br>100 | Ile | Ala | Glu | Phe | Trp<br>105 | Ile | Asn | Gly | Thr<br>110 | Pro | Leu | Val |
| Lys | Lys | Gly<br>115 | Leu | Arg | Gly | Gly | Tyr<br>120 | Phe | Val | Glu | Ala | Gln<br>125 | Pro | Lys | Ile |
| Val | Leu<br>130 | Gly | Gln | Glu | Gln | Asp<br>135 | Ser | Tyr | Gly | Gly | Lys<br>140 | Phe | Asp | Arg | Ser |
| Gln<br>145 | Ser | Phe | Val | Gly | Glu<br>150 | Ile | Gly | Asp | Leu | Tyr<br>155 | Met | Trp | Asp | Ser | Val<br>160 |
| Leu | Pro | Pro | Glu | Asn<br>165 | Ile | Leu | Ser | Ala | Tyr<br>170 | Gln | Gly | Thr | Pro | Leu<br>175 | Pro |
| Ala | Asn | Ile | Leu<br>180 | Asp | Trp | Gln | Ala | Leu<br>185 | Asn | Tyr | Glu | Ile | Arg<br>190 | Gly | Tyr |
| Val | Ile | Ile<br>195 | Lys | Pro | Leu | Val | Trp<br>200 | Val |

What is claimed is:

1. An isolated DNA molecule encoding a tumor-necrosis factor-stimulated gene-14 (TSG-14) polypeptide, comprising a DNA encoding the amino acid sequence of FIG. 9A (SEQ ID NO:4).

2. An isolated DNA molecule according to claim 1, wherein said DNA is derived from the group consisting of cDNA and genomic DNA.

3. An isolated DNA molecule according to claim 1, further comprising an expression vehicle.

4. An isolated DNA molecule according to claim 3, wherein said vehicle further comprises a plasmid.

5. A prokaryotic host cell transformed with an isolated DNA molecule according to claim 1.

6. A host according to claim 5, wherein said host is a bacterium.

7. A eukaryotic host cell transformed with an isolated DNA molecule according to claim 1.

8. A host according to claim 7, wherein said host is selected from a yeast cell and a mammalian cell.

* * * * *